(12) United States Patent
Fukuoka et al.

(10) Patent No.: US 11,091,773 B2
(45) Date of Patent: Aug. 17, 2021

(54) PARTHENOCARPY REGULATION GENE AND USE THEREOF

(71) Applicants: NATIONAL RESEARCH AND DEVELOPMENT AGENCY NATIONAL AGRICULTURE AND FOOD RESEARCH ORGANIZATION, Ibaraki (JP); TAKII & CO., LTD., Kyoto (JP)

(72) Inventors: Hiroyuki Fukuoka, Tsu (JP); Satoshi Matsuo, Tsu (JP); Koji Miyatake, Tsu (JP); Satoshi Shimakoshi, Konan (JP); Souichi Urashimo, Konan (JP); Makoto Endo, Konan (JP)

(73) Assignees: NATIONAL RESEARCH AND DEVELOPMENT AGENCY NATIONAL AGRICULTURE AND FOOD RESEARCH ORGANIZATION, Tsukuba (JP); TAKII & CO., LTD., Kyoto (JP)

( * ) Notice: Subject to any disclaimer, the term of this patent is extended or adjusted under 35 U.S.C. 154(b) by 177 days.

(21) Appl. No.: 15/039,768

(22) PCT Filed: Jan. 19, 2015

(86) PCT No.: PCT/JP2015/051239
§ 371 (c)(1),
(2) Date: May 26, 2016

(87) PCT Pub. No.: WO2015/108185
PCT Pub. Date: Jul. 23, 2015

(65) Prior Publication Data
US 2017/0002376 A1    Jan. 5, 2017

(30) Foreign Application Priority Data

Jan. 17, 2014 (JP) .............................. JP2014-007309

(51) Int. Cl.
| | | |
|---|---|---|
| *C12N 15/82* | (2006.01) | |
| *C07K 14/415* | (2006.01) | |
| *G01N 33/569* | (2006.01) | |
| *C12N 9/10* | (2006.01) | |
| *C12Q 1/6895* | (2018.01) | |

(52) U.S. Cl.
CPC ........ *C12N 15/8287* (2013.01); *C07K 14/415* (2013.01); *C12N 9/1096* (2013.01); *C12N 15/8218* (2013.01); *C12Q 1/6895* (2013.01); *C12Y 206/01* (2013.01); *G01N 33/56961* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 5,336,766 A | 8/1994 | Koga et al. |
| 6,060,648 A | 5/2000 | Heath et al. |
| 8,859,863 B2 | 10/2014 | Petrus Van Dun et al. |
| 8,957,286 B2 | 2/2015 | Shirai et al. |
| 9,253,953 B2 | 2/2016 | Eggink et al. |
| 2010/0333228 A1 | 12/2010 | Shirai et al. |
| 2012/0164303 A1 | 6/2012 | Van Dun et al. |
| 2013/0189419 A1 | 7/2013 | Van Dun et al. |
| 2013/0239258 A1 | 9/2013 | Eggink et al. |
| 2015/0167014 A1 | 6/2015 | Noel et al. |
| 2016/0057960 A1 | 3/2016 | Eggink et al. |

FOREIGN PATENT DOCUMENTS

| | | |
|---|---|---|
| EP | 2883955 | 6/2015 |
| JP | 3-251181 | 11/1991 |
| JP | 2001-520863 | 11/2001 |
| WO | 2009/005343 | 1/2009 |
| WO | 2009/098983 A1 | 8/2009 |
| WO | 2010/101274 A1 | 9/2010 |
| WO | 2010/149628 | 12/2010 |
| WO | 2012/087140 | 6/2012 |
| WO | 2014/021398 | 2/2014 |

OTHER PUBLICATIONS

Merriam Webster Online Dictionary. 2008, www.m-w.com/home.html.*
Bowie et al, Science 247:1306-1310, 1990.*
McConnell et al, Nature 411 (6838):709-713, 2001.*
Jong et al (2009, The Plant Journal 57:160-170).*
Kano-Murakami et al (1993, FEBS 334:365-368).*
Li et al (1994, "Variation for Thermal Properties of Starch In Tropical Maize Germ Plasm", Cereal Chem. 71(1):87-90).*
Bryant (1989, "Antisense RNA Makes Good Sense", Trends in Biotechnology 7(2):20-21).*
Kano-Murakami et al (1993, "A Rice Homeotic Gene, OSH1, Causes Unusual Phenotypes in Transgenic Tobacco", FEBS 334 (3):365-368).*

(Continued)

*Primary Examiner* — Stuart F Baum
(74) *Attorney, Agent, or Firm* — Casimir Jones, S.C.; Robert A. Goetz

(57) ABSTRACT

In order to identify a novel gene responsible for parthenocarpy and to provide use of the gene, the parthenocarpy regulatory gene of the present invention includes a polynucleotide (1) that encodes an amino acid sequence represented by SEQ ID NO: 1, (2) that encodes an amino acid sequence (i) having a sequence identity of 75% or higher relative to the amino acid sequence represented by SEQ ID NO: 1, (3) that encodes an amino acid sequence in which 1 to 98 amino acids are substituted, etc. in the amino acid sequence represented by SEQ ID NO: 1, or (4) that is hybridized with a polynucleotide, which has a sequence complementary to the polynucleotide for encoding the amino acid sequence represented by SEQ ID NO: 1 under a stringent condition.

15 Claims, 31 Drawing Sheets

Specification includes a Sequence Listing.

(56) References Cited

OTHER PUBLICATIONS

Martienssen (1998, "Functional Genomics: Probing Plant Gene Function and Expression with Transposons", PNAS 95(5):2021-2026).*

Jong et al (2009, "The Solanum lycopersicum Auxin Response Factor 7 (SlARF7) Regulates Auxin Signaling during Tomato Fruit Set and Development", The Plant Journal 57:160-170).*

Search Report, EP Patent Application No. 15737177.4, dated Jul. 26, 2017.

Database UniProt [Online] Nov. 28, 2012 (Nov. 28, 2012),"SubName: Full=Uncharacterized protein {ECO:0000313|EnsemblPlants:Solyc03g120450.2.1};", XP002771945.

Database EMBL [Online] Sep. 3, 2012 (Sep. 3, 2012), "TSA: Capsicum annuum MGMT_Contig2960, mRNA sequence.", XP002771946.

Zheng Zuyu et al: "Coordination of auxin and ethylene biosynthesis . . . )", Nature Chemical Biology, vol. 9, No. 4, Apr. 2013 (Apr. 2013), pp. 244-246+2PP, XP002771947.

Miyatake, K. et al. "Development of selective markers linked to a major QTL for parthenocarpy in eggplant (*Solanum melongena* L.)" Theor. Appl. Genet., 2012, vol. 124. pp. 1403-1413.

Mezzetti, B. et al. "The defH9-iaaM auxin—synthesizing gene increases plant fecundity and fruit production in strawberry and raspberry." BMC Biotechnology 2004, 4:4, pp. 1-17.

Acciarri, N. et al. "Genetically modified parthenocarpic eggplants: improved fruit productivity under both greenhouse, and open field cultivation." BMC Biotechnology 2002, 2:4, pp. 1-14.

Zheng, Z. et al. "Coordination of auxin and ethylene biosynthesis by the aminotransferase VAS1." Nature Chemical Biology 9, 244-246 (2013).

Ficcadenti, N. et al. "Genetic engineering of parthenocarpic fruit development in tomato" Molecular Breeding, Oct. 1999, vol. 5, Issue 5, pp. 463-470.

International Search Report, International Patent Application No. PCT/JP2015/051239, dated Apr. 14, 2015.

Miyatake, Koji et al. "Analysis of genetic factors for controlling fruit enlargement in eggplant" Horticultural Research (Japan), Sep. 27, 2014, vol. 13 (separate vol. 2), p. 393.

Kikuchi, Kaori et al. "An analysis of plant hormone content at fruit setting and enlarging in parthenocarpic eggplant", Horticultural Research (Japan), 2008, vol. 7 (separate vol. 2), p. 250.

M1P3Z7_PRUPE, UniProtKB/TrEMBL, AC:M1P3Z7, entry version 4, Oct. 16, 2013, entire text.

Chan, A.P. et al., Draft genome sequence of the oilseed species *Ricinus communis*, Nature Biotechnology, Sep. 2010, vol. 28, No. 9, pp. 951-956, entire text, particularly, summary.

B9RUW7_RICCO, UniProtKB/TrEMBL, AC:B9RUW7, entry version 24, Oct. 16, 2013, entire text.

Wang, Y. et al., "Characteristics of the tomato nuclear genome as determined by sequencing undermethylated EcoRI digested fragments" Theor. Appl. Genet., 2005, vol. 112, pp. 72-84, entire text, particularly summary.

Budiman, M.A., et al., A Deep-Coverage Tomato BAC Library and Prospects Toward Development of an STC Framework for Genome Sequencing, Genome Res., 2000, vol. 10, pp. 129-136, entire text, particularly summary.

K4BMJ4_SOLLC, UniProtKB/TrEMBL, AC:K4BMJ4, entry version 7, Oct. 16, 2013, entire text.

Rotino et al., (1997), "Genetic engineering of parthenocarpic plants" Nature Biotechnology 15: 1398-1401.

Zheng, Z. et al. "Coordination of auxin and ethylene biosynthesis by the aminotransferase VAS 1" Nature Chem. Biol. (2013) 9: 244-246.

Nothmann et al. "Effects of growth regulators on fruit and seed development in eggplant (*Solanum melongena* L.)" J. Hort. Sci. (1975) 50, 23-27.

English translation of International Preliminary Report on Patentability of PCT/JP2015/051239, dated Jul. 28, 2016.

* cited by examiner

FIG. 1
(a)
(b)
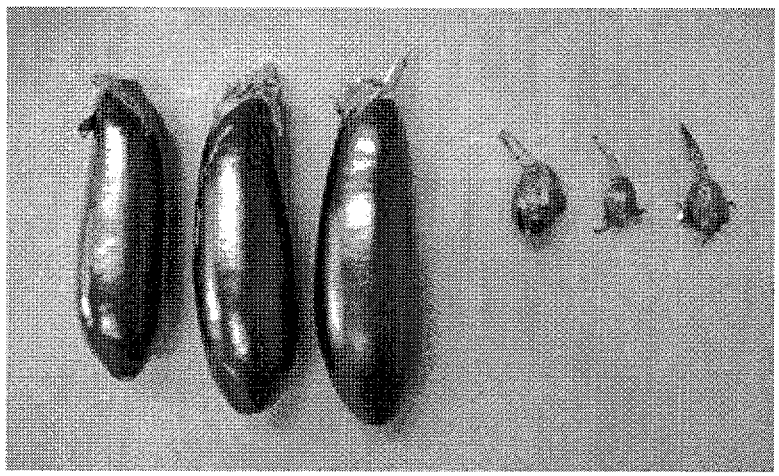
LINE PCSS    CULTIVAR "SENRYO-NIGO"

| | | DNA MARKER | | | | | | | PARTHENOCARPY |
|---|---|---|---|---|---|---|---|---|---|
| | | est_sep 07e19 | SOL 8545 | SOL 8586 | est_sm fl28j21 | SOL 7214 | eme0 7D02 | SOL 8369 | |
| LOCATION ON THIRD CHROMOSOME (cM) | | 65 | 69 | 70 | 86 | 88 | 110 | 111 | |
| INDIVIDUAL NUMBER OF F2 GENERATION | 34 | A | A | H | H | H | H | H | NONE |
| | 25 | A | A | A | H | H | B | B | NONE |
| | 24 | A | A | A | A | H | B | B | NONE |
| | 30 | A | A | A | A | A | H | H | EXIST |
| | 45 | H | H | H | A | A | A | A | EXIST |
| | 44 | H | H | H | H | A | A | A | NONE |
| | 86 | B | B | B | H | H | H | A | NONE |

A indicates parthenocarpic line PCSS, B indicates non-parthenocarpic line TN-43, H indicates heterotype (b)

| | | DNA MARKER | | | | | | | | | | | PARTHENOCARPY |
|---|---|---|---|---|---|---|---|---|---|---|---|---|---|
| | | est_sm fl28j21 | ec31 43A | ec31 13A | ec31 10A | ec30 98A | SSR 03 | ec30 77F | ec30 65A | ec30 57B | ec30 48A | ec30 04E | SOL 8369 | |
| INDIVIDUAL NUMBER OF F3 GENERATION | P43F3_007 | A | A | A | A | A | A | A | B | B | B | B | B | EXIST |
| | P43F3_430 | A | A | A | A | A | A | B | B | B | B | B | B | EXIST |
| | P43F3_051 | A | A | A | A | H | H | H | H | H | H | B | B | NONE |
| | P43F3_316 | A | A | H | H | H | H | B | B | B | B | B | B | NONE |
| | P43F3_236 | B | B | B | B | B | B | A | A | A | A | A | A | NONE |
| | P43F3_429 | B | B | B | B | A | A | A | A | A | A | A | A | EXIST |

| | | ec31 10A | ec30 98A | SSR 03 | ec30 88B | ec30 87X | ec30 77F | PARTHENOCARPY |
|---|---|---|---|---|---|---|---|---|
| INDIVIDUAL NUMBER OF F5 GENERATION | P43F3_051_46_164 | A | H | H | H | A | A | NONE |
| | P43F3_316_42_1 | A | A | A | H | H | B | NONE |
| | P43F3_316_23_158 | H | H | H | A | A | B | EXIST |

| | | ec30 98A | SSR 03 | PaSeq 123 | PaSeq 128 | ec30 88B | ec30 87X | PARTHENOCARPY |
|---|---|---|---|---|---|---|---|---|
| INDIVIDUAL NUMBER OF F8 GENERATION | P43F3_316_7_31_F_E10_10 | B | B | A | B | B | B | EXIST |
| | P43F3_316_7_31_F_E10_04 | B | B | B | B | B | B | NONE |

◄——► DEDUCED LOCATION REGION OF PARTHENOCARPY RESPONSIBLE GENE

Ovaries and anthers were taken from flowers before petal coloring (St3), at petal coloring (St4), and at anthesis (St6). NP: Non-parthenocarpic line, PCSS: PCSS line An extract from the ovary at anthesis was analyzed.
Values indicate relative quantitative values when the non-parthenocarpic line (NP) is 1.
Arrows indicate deduced IAA metabolic pathways. Solid line arrows indicate pathways on which an enzyme gene is confirmed in *Arabidopsis*, and dotted line arrows indicate pathways on which an enzyme gene is not confirmed.

*There is a significant difference (5%) between different characters in Tukey's multiple test.

*There is a significant difference (5%) between different characters in Tukey's multiple test.

*There is a significant difference (1%) between different characters in Tukey's multiple test.

SEQUENCE LISTING

<160> NUMBER OF SEQ ID NOS: 78

<210> SEQ ID NO 1
<211> LENGTH: 394
<212> TYPE: PRT
<213> ORGANISM: Solanum melongena

<400> SEQUENCE: 1

```
Met Gly Ser Phe Gly Met Leu Ala Arg Arg Ala Val Leu Thr Asp Thr
1               5                   10                  15

Pro Val Met Val Gln Ile Gln Glu Leu Ile Arg Gly Asn Lys Asp Cys
            20                  25                  30

Ile Ser Leu Ala Gln Gly Val Val Tyr Trp Gln Pro Ala Gln Ala
        35                  40                  45

Leu Glu Lys Val Lys Glu Ile Ile Trp Glu Pro Ser Val Ser Arg Tyr
    50                  55                  60

Gly Ala Asp Glu Gly Leu Pro Glu Leu Arg Glu Ala Leu Met Gln Lys
65                  70                  75                  80

Leu Gly His Glu Asn Asn Leu His Lys Ser Ser Val Met Val Thr Ala
                85                  90                  95

Gly Ala Asn Gln Ala Phe Val Asn Val Val Leu Thr Leu Cys Asp Ala
            100                 105                 110

Gly Asp Ser Val Val Met Phe Ala Pro Tyr Tyr Phe Asn Ala His Met
        115                 120                 125

Ser Phe Gln Met Thr Gly Val Thr Asp Ile Leu Val Gly Pro Gly Asp
    130                 135                 140

Pro Lys Thr Leu His Pro Asp Ala Asp Trp Leu Glu Ser Thr Leu Lys
145                 150                 155                 160

Asn Thr Val Pro Thr Pro Lys Leu Val Thr Val Asn Pro Gly Asn
                165                 170                 175

Pro Ser Gly Thr Tyr Ile Pro Glu Ser Leu Leu Lys Arg Ile Ser Asp
            180                 185                 190

Ile Cys Lys Lys Ala Gly Cys Trp Leu Val Ile Asp Asn Thr Tyr Glu
        195                 200                 205

Tyr Phe Met Tyr Asp Asn Arg Lys His Val Cys Ile Glu Ala Asn His
    210                 215                 220

Ile Val Asn Ile Phe Ser Phe Ser Lys Ala Tyr Gly Met Met Gly Trp
225                 230                 235                 240

Arg Val Gly Tyr Ile Ala Tyr Pro Ser Glu Val Glu Gly Leu Ala Ala
                245                 250                 255

Gln Leu Leu Lys Val Gln Asp Asn Ile Pro Ile Cys Ala Ser Ile Ile
            260                 265                 270

Ser Gln Arg Leu Ala Leu Tyr Ser Met Glu Met Gly Pro Glu Trp Val
        275                 280                 285

Thr Asn Gln Val Lys Asp Leu Val Lys Asn Arg Glu Val Leu Leu Glu
    290                 295                 300

Ala Leu Ser Pro Leu Gly Lys Gly Ala Val Lys Gly Glu Gly Ala
305                 310                 315                 320

Ile Tyr Leu Trp Ala Lys Leu Pro Asp Lys Tyr Met Asp Asp Phe Lys
                325                 330                 335

Val Val His Trp Leu Ala Lys Arg His Gly Val Val Leu Ile Pro Gly
            340                 345                 350

Ser Ser Ser Gly Cys Pro Gly Tyr Val Arg Val Ser Phe Gly Gly Leu
        355                 360                 365
```

```
Ile Glu Lys Asp Cys Arg Ala Ala Ala Glu Arg Leu Arg Lys Gly Leu
    370                 375                 380

Glu Glu Leu Val Asn Ser Gly Met Ala Ser
385                 390

<210> SEQ ID NO 2
<211> LENGTH: 1625
<212> TYPE: DNA
<213> ORGANISM: Solanum melongena

<400> SEQUENCE: 2
gtccgtagca gtcaaattta ttcatattta acaaaaagat ccaatttta tattttttac      60 aatccctta tataggttcc aagcttttg taagattttc agaaagggaa aggccttttt     120
tgctctgtgg gtaggtggat aagaactctt tccttgaagg tagtgtttat tttattgttt     180
ttactgagaa agaggaaatg ggttctttcg gaatgctcgc tagaagagct gttcttaccg     240
atacaccagt tatggttcag atacaagaac tgattcgagg taataaagat tgtatttctc     300
tagctcaggg agtagtgtac tggcaaccac ctgcacaagc acttgaaaag gtgaaagaaa     360
ttatctggga accttcagtt agtcgctatg tgctgatga gggccttcct gagcttaggg     420
aggcgttgat gcaaaagttg ggtcatgaaa ataacctcca taaatcctcg gtgatggtta     480
ctgctggtgc taatcaggct ttcgtaaatg tcgttctcac cctgtgtgat gctggtgatt     540
cagttgttat gtttgcacca tactatttca atgcacacat gtcattccag atgacaggtg     600
ttactgatat tctggtgggt cctggtgatc caagacact ccatcctgat gcagactggt     660
tggagagtac tttaaagaat actgtaccaa caccaaagct cgtcactgtt gttaatcctg     720
gcaatccatc aggaacatat atccccgagt ctcttcttaa gaggatatct gatatttgta     780
agaaggcagg atgttggctc gtaattgata acacatatga gtatttcatg tatgataatc     840
ggaaacatgt ttgcatagaa gcaaaccaca ttgtcaacat cttttccttc tctaaagcat     900
atgggatgat gggatggaga gttggatata tagcataccc atcggaagtg aagggcttg      960 cagctcaact ccttaaagtt caggacaaca taccaatctg tgcttcaata atctcacaac    1020
gactggctct ttactcaatg gaaatgggac agaatgggt aactaatcaa gtaaaagacc    1080
ttgtcaagaa cagagaggtg cttctagaag ccttatctcc tttgggaaag ggagctgtta    1140
aaggggagaa aggtgccatt tacctgtggg caaagctgcc agataaatac atggacgact    1200
tcaaagtagt tcactggcta gctaagaggc atggagtagt cctgatccct ggaagttcca    1260
gcggttgtcc aggttatgtt agggtctcct ttggaggatt gatcgagaag gactgtcgag    1320
cagctgcaga aaggctcaga aaaggtttgg aagagctggt aaatagtgga atggcgtcat    1380
gattctctct gactaaaatt tagtgtcagc tggttctcct ggacatcagt catcaacaat    1440
acaatgacag acactttcta tccttaataa ttgaagggtt ttaagctttg caacttgatc    1500
attggacatg caagttaaaa cttgccattc tgtatagttt gaaatgaagt attcatagat    1560
acctactttt cttaaatgga tgatggaagt gtctcattta tctcagagca tatctcattg    1620
aatca                                                               1625

<210> SEQ ID NO 3
<211> LENGTH: 1305
<212> TYPE: DNA
<213> ORGANISM: Solanum melongena

<400> SEQUENCE: 3
tttttgctct gtgggtaggt ggataagaac tcttttcttg aaggtagtgt ttattttatt      60
```

```
gtttttactg agaaagagga aatgggttct tcggaatgc tcgctagaag agctgttctt      120
accgatacac cagttatggt tcagatacaa gaactgattc gaggtaataa agattgtatt      180
tctctagctc agggagtagt gtactggcaa ccacctgcac aagcacttga aaaggtgaaa      240
gaaattatct gggaaccttc agttagtcgc tatggtgctg atgagggcct tcctgagctt      300
agggaggcgt tgatgcaaaa gttgggtcat gaaaataacc tccataaatc ctcggtgatg      360
gttactgctg gtgctaatca ggctttcgta aatgtcgttc tcaccctgtg tgatgctggt      420
gattcagttg ttatgtttgc accatactat ttcaatgcac acatgtcatt ccagatgaca      480
ggtgttactg atattctggt gggtcctggt gatcccaaga cactccatcc tgatgcagac      540
tggttggaga gtactttaaa gaatactgta ccaacaccaa agctcgtcac tgttgttaat      600
cctggcaatc catcaggaac atatatcccc gagtctcttc ttaagaggat atctgatatt      660
tgtaagaagg caggatgttg gctcgtaatt gataacacat atgagtattt catgtatgat      720
aatcggaaac atgtttgcat agaagcaaac cacattgtca acatcttttc cttctctaaa      780
gcatatggga tgatgggatg gagagttgga tatatagcat acccatcgga agtggaaggg      840
cttgcagctc aactccttaa agttcaggac aacataccaa tctgtgcttc aataatctca      900
caacgactgg ctctttactc aatggaaatg ggaccagaat gggtaactaa tcaagtaaaa      960
gaccttgtca agaacagaga ggtgcttcta gaagccttat ctcctttggg aaagggagct     1020 gttaagggg gagaaggtgc catttacctg tgggcaaagc tgccagataa atacatggac     1080
gacttcaaag tagttcactg gctagctaag aggcatggag tagtcctgat ccctggaagt     1140
tccagcggtt gtccaggtta tgttagggtc tcctttggag gattgatcga aaggactgt     1200 cgagcagctg cagaaaggct cagaaaaggt ttggaagagc tggtaaatag tggaatggcg     1260
tcatgattct ctctgactaa aatttagtgt cagctggttc tcctg                    1305

<210> SEQ ID NO 4
<211> LENGTH: 6528
<212> TYPE: DNA
<213> ORGANISM: Solanum melongena

<400> SEQUENCE: 4
gtccgtagca gtcaaattta ttcatattta acaaaaagat ccaattttta tatttttac       60 aatccctta tataggttcc aagcttttta taagatttc agaaagggaa aggccttttt      120
tgctctgtgg gtaggtggat aagaactctt ttcttgaagg tagtgtttat tttattgttt      180
ttactgagaa agaggaaatg ggttctttcg gaatgctcgc tagaagagct gttcttaccg      240
atacaccagt tatggttcag gtaaattaca agatcctaga ttggatttct tgctcttttg      300
tttggtttaa ggttctgtgc tttaatggga tatgttgttg ttgtgttttg caatcgatag      360
atacaagaac tgattcgagg taataaagat tgtatttctc tagctcaggt ttgtttactt      420
tctccaatgt ttgtttcatt ttgttttact atatcttagt tttattattc tactttttcat      480 tgaatggttc aaaaagttga gaactttgat aaaattcatc tgttgttgtg atgtctttga      540
agcctacata tcatcttatt gtgccttttcg aaatcttgat tagattgact tacattaaaa      600
attggctaat tcattcttga agttatcaat ttcaattttt ttttcagtt gaaatatgaa      660 ttgcttaata tttaagctag taattgggga aaaaaaatca aactggactt ccctcccatg      720
taaagaatgt atttgcagat ggttttgaat gtgaaaatg gagattatga gtgtccactg      780
agctgggtgg gtataagggc ttgggtaggt gggtttcggg cctagagcac atgtgaagga      840
```

```
ggtctactgg tacaagattg acattttctc tttccttaag ttcctctggt gattgcaaat    900
aacataaatt gcctgagctt cttgttttgc gaagaaatct tctgaggttt ctcccatgat    960
ctctggagtt acaaaattat tttgctagta tgttccatgc tcggttgtcc ttttcctgtg   1020
caaaaagagt tataatactg ttcttttgat ctgtttttat ttgggttaac caagtatgat   1080
gtgatacaga agaatatctg ccgccctacc atgtgctgtg agtagtgatc cctttgtgtt   1140
atcctcctat tattggactg ttttacgaat gactggttct attatgatct ctgaggactg   1200
atctgttgac aagcaagttt tatcaacctc catctgaaaa aaagaaagt ttaatcaacc    1260
taaacctacc aatggaagtt ttagaagttg tatagtttgc tggggttggg gcctggggaa   1320
tgagtgtgta cttatttgct tctttatgta ccttccagag agagtaaaca aaggaataga   1380
gttatctgtt gttggtggat cttttctgttg aagtgtgtag ttatattggt tttgcctgaa   1440
tatggttgtc catgttttcc atccatgtat cttggtacca tcttattttt ttctccgtct   1500
tacagggagt agtgtactgg caaccacctg cacaagcact tgaaaaggtg aaagaaatta   1560
tctgggaacc ttcagttagt cgctatggtg ctgatgaggg ccttcctgag cttagggagg   1620
cgttgatgca aaaggtatgg tctatcagct ggattactct aatactctgg ttttcatcgt   1680
atgggctggg tagtggaaca acattggag tggtgtaggg tgcttttgcc aggtgaaacg    1740
gtagttactg tcatgtatga agttggattc atttcatgtt ttcaaactat atcattcact   1800
tgttgagttt tggttttac gttgtttggt ctaatacttt ctttgtgctc ttctccagtt    1860
gggtcatgaa ataaccctcc ataaatcctc ggtgatggtt actgctggtg ctaatcaggt   1920
aaaatgttac tttttacta ttcagtcatc tgaggatata gggtcagtca cttcacctct    1980
ttttcttacc tgccctgaat agtagtaggc taccttcttt tctcgccttt cttccatctt   2040
tttccagata aaggttggat gttttagaat gaaactgcgt tttggagatt tgtttgcttg   2100
agttagagtg ggttgagatt gattctacct tcatacaaga ttcatttgct ttgacagagg   2160
accagtattt gggtgcatgt ttacttcacc ttcctaagct attcttcagt tccccttttc   2220
ccttcattaa tgttcaaagt tgtctagttc atactagaaa cacggcaggg ctcctcttaa   2280
aaaaagaaag tgcaattttc tacttttgc attgtcacaa tactaagaga tttcatctcc    2340
aaaaccagga agtgatgctt gtgagggaac gttttcccttt tcttttttacc cctctctcta   2400
tctctctctt aaatgaagat ttcttagagt ttatgtggtc aagaaaccgt acagtacttt   2460
tcctgataaa tggtatggat acttctgaaa gaaaaataga actgcctcac tgataaatgg   2520
tgtgggattc cactaggtat gttgttgttg ttgttgtttt ctctatcatg atgcatacag   2580
tatgcagtgt atggaaaggt tggtgtgatt ttgagatttg gattttattt tcttctgctt   2640
ctacccatct aaagattatt cttttttctcg tgtgtatttt tcttgataaa aaagatcatt   2700
cttctgttgt gggcttattc agctccatgt tctaacttga tcaaaaaagt caaatgtgct   2760
ctcttttct tgtcttttcc gtttttttgta ataagacctc ttttagtttt tgcatgttat    2820
cactgtactt ttgtatgtta ccattttcat gagatgacaa tcttgcaatg gaacatatg    2880
cagcacaaaa ctctccattt agtatcatct gtcagaaaca tatagggaaa gaatctactg   2940
acatatctag catgctcaag cacttggccc tcacaatttt gtctgcaaaa tggaacttag   3000
ggattacttc gactactaat ttgagaatta attgcctaga ttttcaatga ctgagtaaat   3060
gatggtccaa ggggctcaga aagtatgagt acagacacat cattacgtac ctgtccatta   3120
cagagcagta ttctcttttt gaacaggaga attgtgtcct caatagtcct ccaaattaaa   3180
atcacaattt attgcaataa acaaattcgg atgaaacctt aagctgaatg aagatagtag   3240
```

-continued

```
agctatgtta atgagccatt tgtagagcaa tagagttgct acatgtatgg gtaaattaat      3300
tagtgtattg tctatattct tgttagtga ctaatggact agctgtatcc ctatcactta       3360
gaaatcacta atggagtctc actgaattga ttccaggctt tcgtaaatgt cgttctcacc      3420
ctgtgtgatg ctggtgattc agttgttatg tttgcaccat actatttcaa tgcacacatg     3480
tcattccaga tgacaggtgt tactgatatt ctggtgggtc ctggtgatcc caagacactc     3540
catcctgatg caggtttgta agttcagatg atgttcattt tgtgataccc tccccattat     3600
taagactgct attcctttag tttccttaag actgattaca ctagatgttg tcatatacat     3660
ctctgttgtg tagcatgcat gttcaagttt gagggaacat ccttttatc tttgtcatct      3720 cagcactttg aatatatat cataatcact aatcacatat gtactatgag ttactttttt      3780
cctctttgct tgaaatttat caaaaaactc catcttctct gaatctaaca ctacttgtgc     3840
agaaatcaac ttaagaagag gttgctgcag aagtagtgtt cagctttgta ttgcaagttg     3900
tgtaaatcat tcataatggt ctattagtct tgatttgtag aatgttgtct ggaaagcaat     3960
cattctgtgt tttttctcgt attggatgtc ctcaccccat ccccaccaga aagaaaccaa     4020
aaaaaataat gaatttagta aacttatagt ttgacacttt gaagcataat gttaacctaa     4080
atattgcttc tattttgcat aatggacttg agagtttcaa aacattatct gccttcgtta     4140
tttgattgtt tatggattga tatattccat gatttctcaa ttttcagact ggttggagag     4200
tactttaaag aatactgtac caacaccaaa gctcgtcact gttgttaatc ctggcaatcc     4260
atcaggaaca tatatccccg agtctcttct taaggtctct atctcatctt tatagatatg     4320
aatgtattgg ttgaagtcat cagttattca aagtgcatta ctattctcat ctgatttta     4380 ctttattgaa acatcaacaa gttgcatttt gttcatgtag aggatatctg atatttgtaa     4440
gaaggcagga tgttggctcg taattgataa cacatatgag taagttactt tttctgttgc     4500
atacgaatct tttagtttct cattttaaat tgtgtactgg ttgttaataa ctggtgccga     4560
tatgttttct catccatgga tgaaagatga cattcttaga actaaagatg atgagggttg     4620
ttgaatggac taatcctgga atactttggg ttagaccagc aagagattat tgaataaacc     4680
aaggaaacag gtcgtttgca ttgcattgtg aggaaatctt tttgctttgt gaacctaaac     4740
ttgaactaaa tttgataggc aagaaaattt atggtatcct gggatctgtt gccatatttt     4800
gattgctgag aaggggagaa aggaaatagc taaggtgaaa gaatgatcag tctttgaatt     4860
catccaaatt ggcccacttg ttgctgtttg ttctcaatct ctagatggaa aataagccta     4920
gaaagttggc ttctcaacga gttagatagt taggacacat tactattgag tctttcctcc     4980
tccatgaatg tgaacatctt gttctgtcaa acatcatctc tgttccttct ttttcttgca     5040 acttttgct ttacactctg cttgtcgttt tctatattcc tgaatgatat gttcttatat      5100
atatgttgta agttatttgc aggtatttca tgtatgataa tcggaaacat gtttgcatag     5160
aagcaaacca cattgtcaac atcttttcct tctctaaagc atatgggatg atgggatgga    5220
gagttggata tgtaagtgat gcttgttcta acttatatct agcaatgtaa taatattggg     5280
cagacaagtg attattattc tgctgggtga gcctcaacac aaccagaaaa tatacctggt     5340
taaaagatga ttttttctat gttttccgca actgcatctt cttgcctcat aaactccctc    5400
gtctttacct ttaaaccaaa aaccaaaaaa aatttaaaaa aattaaactg ttgtctttac     5460
ttatacctct ttttaaaacc agcatgtatg acacctttaa tcagtctctc tatccttgtc    5520
catcattaac ttttataacg aataatgttg cgtcctgtca tttgtgcctg gttgagtgat     5580
```

```
ctgctggaat tggatataaa attggcctca ataacaacca aaatacaagt gttcttttgc      5640
aacaaaaagg agttgttcca acagctaaga cttatggcat atgagacatg attgctttac      5700
cagatgtttt tgctgcaatg taaattttgc agcaaaattc ctcagcaaac ttttgtactg      5760
aagatttact cctgaatgga gaaggttgtt tcatcttgtg agtgagctaa actcatgtct      5820
taatcgatgc agatagcata cccatcggaa gtggaagggc ttgcagctca actccttaaa      5880
gttcaggaca acataccaat ctgtgcttca ataatctcac aacgactggc tctttactca      5940
atggaaatgg gaccagaatg ggtaactaat caagtaaaag accttgtcaa gaacagagag      6000
gtgcttctag aagccttatc tcctttggga aaggagctg ttaaaggggg agaaggtgcc        6060
atttacctgt gggcaaagct gccagataaa tacatggacg acttcaaagt agttcactgg      6120
ctagctaaga ggcatggagt agtcctgatc cctggaagtt ccagcggttg tccaggttat      6180
gttagggtct cctttggagg attgatcgag aaggactgtc gagcagctgc agaaaggctc      6240
agaaaaggtt tggaagagct ggtaaatagt ggaatggcgt catgattctc tctgactaaa      6300
atttagtgtc agctggttct cctggacatc agtcatcaac aatacaatga cagacacttt      6360
ctatccttaa taattgaagg gttttaagct ttgcaacttg atcattggac atgcaagtta      6420
aaacttgcca ttctgtatag tttgaaatga agtattcata gatacctact tttcttaaat      6480
ggatgatgga agtgtctcat ttatctcaga gcatatctca ttgaatca                   6528

<210> SEQ ID NO 5
<211> LENGTH: 260
<212> TYPE: DNA
<213> ORGANISM: Solanum melongena

<400> SEQUENCE: 5
gtccgtagca gtcaaattta ttcatattta acaaaaagat ccaattttta tattttttac        60
aatcccttta tataggttcc aagcttttg taagattttc agaaagggaa aggccttttt        120
tgctctgtgg gtaggtggat aagaactctt ttcttgaagg tagtgtttat tttattgttt       180
ttactgagaa agaggaaatg ggttctttcg gaatgctcgc tagaagagct gttcttaccg       240
atacaccagt tatggttcag                                                  260

<210> SEQ ID NO 6
<211> LENGTH: 100
<212> TYPE: DNA
<213> ORGANISM: Solanum melongena

<400> SEQUENCE: 6
gtaaattaca agatcctaga ttggatttct tgctcttttg tttggtttaa ggttctgtgc        60
tttaatggga tatgttgttg ttgtgttttg caatcgatag                             100

<210> SEQ ID NO 7
<211> LENGTH: 48
<212> TYPE: DNA
<213> ORGANISM: Solanum melongena

<400> SEQUENCE: 7
atacaagaac tgattcgagg taataaagat tgtatttctc tagctcag                     48

<210> SEQ ID NO 8
<211> LENGTH: 1097
<212> TYPE: DNA
<213> ORGANISM: Solanum melongena

<400> SEQUENCE: 8
```

```
gtttgtttac tttctccaat gtttgtttca ttttgttttta ctatatctta gttttattat    60 tctactttc attgaatggt tcaaaaagtt gagaactttg ataaaattca tctgttgttg      120
tgatgtcttt gaagcctaca tatcatctta ttgtgccttt cgaaatcttg attagattga    180
cttacattaa aaattggcta attcattctt gaagttatca atttcaattt tttttttcag    240
ttgaaatatg aattgcttaa tatttaagct agtaattggg gaaaaaaaat caaactggac    300
ttccctccca tgtaaagaat gtatttgcag atggttttga atgtgaaaaa tggagattat    360
gagtgtccac tgagctgggt gggtataagg gcttgggtag gtgggtttcg ggcctagagc    420
acatgtgaag gaggtctact ggtacaagat tgacattttc tctttcctta agttcctctg    480
gtgattgcaa ataacataaa ttgcctgagc ttcttgtttt gcgaagaaat cttctgaggt    540
ttctcccatg atctctggag ttacaaaatt attttgctag tatgttccat gctcggttgt    600
ccttttcctg tgcaaaaaga gttataatac tgttcttttg atctgttttt atttgggtta    660
accaagtatg atgtgataca gaagaatatc tgccgcccta ccatgtgctg tgagtagtga    720
tccctttgtg ttatcctcct attattggac tgttttacga atgactggtt ctattatgat    780
ctctgaggac tgatctgttg acaagcaagt tttatcaacc tccatctgaa aaaaagaaa     840 gtttaatcaa cctaaaccta ccaatggaag ttttagaagt tgtatagttt gctggggttg    900
gggcctgggg aatgagtgtg tactatttg cttcttatg taccttccag agagagtaaa     960
caaaggaata gagttatctg ttgttggtgg atctttctgt tgaagtgtgt agttatattg   1020
gttttgcctg aatatggttg tccatgtttt ccatccatgt atcttggtac catcttattt   1080
ttttctccgt cttacag                                                  1097

<210> SEQ ID NO 9
<211> LENGTH: 129
<212> TYPE: DNA
<213> ORGANISM: Solanum melongena

<400> SEQUENCE: 9
ggagtagtgt actggcaacc acctgcacaa gcacttgaaa aggtgaaaga aattatctgg     60
gaaccttcag ttagtcgcta tggtgctgat gagggccttc ctgagcttag ggaggcgttg    120
atgcaaaag                                                           129

<210> SEQ ID NO 10
<211> LENGTH: 224
<212> TYPE: DNA
<213> ORGANISM: Solanum melongena

<400> SEQUENCE: 10
gtatggtcta tcagctggat tactctaata ctctggtttt catcgtatgg gctgggtagt     60
ggaacaaaca ttggagtggt gtagggtgct tttgccaggt gaaacggtag ttactgtcat    120
gtatgaagtt ggattcattt catgttttca aactatatca ttcacttgtt gagttttggt    180
ttttacgttg tttggtctaa tactttcttt gtgctcttct ccag                    224

<210> SEQ ID NO 11
<211> LENGTH: 60
<212> TYPE: DNA
<213> ORGANISM: Solanum melongena

<400> SEQUENCE: 11
ttgggtcatg aaaataacct ccataaatcc tcggtgatgg ttactgctgg tgctaatcag     60
```

<210> SEQ ID NO 12
<211> LENGTH: 1478
<212> TYPE: DNA
<213> ORGANISM: Solanum melongena

<400> SEQUENCE: 12

| | | | | | |
|---|---|---|---|---|---|
| gtaaaatgtt | acttttttac | tattcagtca | tctgaggata | tagggtcagt | cacttcacct | 60 |
| cttttttctta | cctgccctga | atagtagtag | gctaccttc | ttctcgcct | ttcttccatc | 120 |
| tttttccaga | taaaggttgg | atgttttaga | atgaaactgc | gttttggaga | tttgtttgct | 180 |
| tgagttagag | tggggttgaga | ttgattctac | cttcatacaa | gattcatttg | ctttgacaga | 240 |
| ggaccagtat | ttgggtgcat | gtttacttca | ccttcctaag | ctattcttca | gttcccttt | 300 |
| tcccttcatt | aatgttcaaa | gttgtctagt | tcatactaga | aacacggcag | ggctcctctt | 360 |
| aaaaaagaa | agtgcaattt | tctactttt | gcattgtcac | aatactaaga | gatttcatct | 420 |
| ccaaaaccag | gaagtgatgc | ttgtgaggga | acgttttccc | tttctttta | ccctctctc | 480 |
| tatctctctc | ttaaatgaag | atttcttaga | gtttatgtgg | tcaagaaacc | gtacagtact | 540 |
| tttcctgata | aatggtatgg | atacttctga | aagaaaaata | gaactgcctc | actgataaat | 600 |
| ggtgtgggat | tccactaggt | atgttgttgt | tgttgttgtt | ttctctatca | tgatgcatac | 660 |
| agtatgcagt | gtatggaaag | gttggtgtga | ttttgagatt | tggatttat | tttcttctgc | 720 |
| ttctacccat | ctaaagatta | ttctttttct | cgtgtgtatt | tttcttgata | aaaaagatca | 780 |
| ttcttctgtt | gtgggcttat | tcagctccat | gttctaactt | gatcaaaaaa | gtcaaatgtg | 840 |
| ctctcttttt | cttgtctttt | ccgttttttg | taataagacc | tcttttagtt | tttgcatgtt | 900 |
| atcactgtac | ttttgtatgt | taccattttc | atgagatgac | aatcttgcaa | tgggaacata | 960 |
| tgcagcacaa | aactctccat | ttagtatcat | ctgtcagaaa | catataggga | aagaatctac | 1020 |
| tgacatatct | agcatgctca | agcacttggc | cctcacaatt | ttgtctgcaa | aatggaactt | 1080 |
| agggattact | tcgactacta | atttgagaat | taattgccta | gattttcaat | gactgagtaa | 1140 |
| atgatggtcc | aaggggctca | gaaagtatga | gtacagacac | atcattacgt | acctgtccat | 1200 |
| tacagagcag | tattctcttt | ttgaacagga | gaattgtgtc | ctcaatagtc | ctccaaatta | 1260 |
| aaatcacaat | ttattgcaat | aaacaaattc | ggatgaaacc | ttaagctgaa | tgaagatagt | 1320 |
| agagctatgt | taatgagcca | tttgtagagc | aatagagttg | ctacatgtat | gggtaaatta | 1380 |
| attagtgtat | tgtctatatt | ctttgttagt | gactaatgga | ctagctgtat | ccctatcact | 1440 |
| tagaaatcac | taatggagtc | tcactgaatt | gattccag | | | 1478 |

<210> SEQ ID NO 13
<211> LENGTH: 157
<212> TYPE: DNA
<213> ORGANISM: Solanum melongena

<400> SEQUENCE: 13

| | | | | | |
|---|---|---|---|---|---|
| gctttcgtaa | atgtcgttct | caccctgtgt | gatgctggtg | attcagttgt | tatgtttgca | 60 |
| ccatactatt | tcaatgcaca | catgtcattc | cagatgacag | gtgttactga | tattctggtg | 120 |
| ggtcctggtg | atcccaagac | actccatcct | gatgcag | | | 157 |

<210> SEQ ID NO 14
<211> LENGTH: 634
<212> TYPE: DNA
<213> ORGANISM: Solanum melongena

<400> SEQUENCE: 14

```
gtttgtaagt tcagatgatg ttcattttgt gataccctcc ccattattaa gactgctatt      60
cctttagttt ccttaagact gattacacta gatgttgtca tatacatctc tgttgtgtag     120
catgcatgtt caagtttgag ggaacatcct ttttatcttt gtcatctcag cactttggaa     180
tatatatcat aatcactaat cacatatgta ctatgagtta cttttttcct ctttgcttga     240
aatttatcaa aaaactccat cttctctgaa tctaacacta cttgtgcaga aatcaactta     300
agaagaggtt gctgcagaag tagtgttcag ctttgtattg caagttgtgt aaatcattca     360
taatggtcta ttagtcttga tttgtagaat gttgtctgga aagcaatcat tctgtgtttt     420
ttctcgtatt ggatgtcctc accccatccc caccagaaag aaaccaaaaa aataatgaa      480 tttagtaaac ttatagtttg acactttgaa gcataatgtt aacctaaata ttgcttctat     540
tttgcataat ggacttgaga gtttcaaaac attatctgcc ttcgttattt gattgtttat     600
ggattgatat attccatgat ttctcaattt tcag                                 634

<210> SEQ ID NO 15
<211> LENGTH: 107
<212> TYPE: DNA
<213> ORGANISM: Solanum melongena

<400> SEQUENCE: 15
actggttgga gagtacttta aagaatactg taccaacacc aaagctcgtc actgttgtta      60
atcctggcaa tccatcagga acatatatcc ccgagtctct tcttaag                   107

<210> SEQ ID NO 16
<211> LENGTH: 126
<212> TYPE: DNA
<213> ORGANISM: Solanum melongena

<400> SEQUENCE: 16
gtctctatct catctttata gatatgaatg tattggttga agtcatcagt tattcaaagt      60
gcattactat tctcatctga tttttacttt attgaaacat caacaagttg cattttgttc     120
atgtag                                                                126

<210> SEQ ID NO 17
<211> LENGTH: 59
<212> TYPE: DNA
<213> ORGANISM: Solanum melongena

<400> SEQUENCE: 17
aggatatctg atatttgtaa gaaggcagga tgttggctcg taattgataa cacatatga      59

<210> SEQ ID NO 18
<211> LENGTH: 643
<212> TYPE: DNA
<213> ORGANISM: Solanum melongena

<400> SEQUENCE: 18
gtaagttact ttttctgttg catacgaatc ttttagtttc tcattttaaa ttgtgtactg      60
gttgttaata actggtgccg atatgttttc tcatccatgg atgaaagatg acattcttag     120
aactaaagat gatgagggtt gttgaatgga ctaatcctgg aatactttg gttagaccag      180 caagagatta ttgaataaac caaggaaaca ggtcgtttgc attgcattgt gaggaaatct     240
ttttgctttg tgaacctaaa cttgaactaa atttgatagg caagaaaatt tatggtatcc     300
tgggatctgt tgccatattt tgattgctga gaaggggaga aaggaaatag ctaaggtgaa     360
```

```
agaatgatca gtctttgaat tcatccaaat tggcccactt gttgctgttt gttctcaatc    420
tctagatgga aaataagcct agaaagttgg cttctcaacg agttagatag ttaggacaca    480
ttactattga gtcttttcctc ctccatgaat gtgaacatct tgttctgtca acatcatct    540 ctgttccttc tttttcttgc aactttttgc tttacactct gcttgtcgtt ttctatattc    600
ctgaatgata tgttcttata tatatgttgt aagttatttg cag                      643

<210> SEQ ID NO 19
<211> LENGTH: 109
<212> TYPE: DNA
<213> ORGANISM: Solanum melongena

<400> SEQUENCE: 19
gtatttcatg tatgataatc ggaaacatgt ttgcatagaa gcaaaccaca ttgtcaacat     60
cttttccttc tctaaagcat atgggatgat gggatggaga gttggatat                109

<210> SEQ ID NO 20
<211> LENGTH: 601
<212> TYPE: DNA
<213> ORGANISM: Solanum melongena

<400> SEQUENCE: 20
gtaagtgatg cttgttctaa cttatatcta gcaatgtaat aatattgggc agacaagtga     60
ttattattct gctgggtgag cctcaacaca accagaaaat atacctggtt aaaagatgat    120
tttttctatg ttttccgcaa ctgcatcttc ttgcctcata aactccctcg tctttacctt    180
taaaccaaaa accaaaaaaa atttaaaaaa attaaactgt tgtctttact tatacctctt    240
tttaaaacca gcatgtatga caccttaat cagtctctct atccttgtcc atcattaact    300
tttataacga ataatgttgc gtcctgtcat ttgtgcctgg ttgagtgatc tgctggaatt    360
ggatataaaa ttggcctcaa taacaaccaa aatacaagtg ttcttttgca acaaaaagga    420
gttgttccaa cagctaagac ttatggcata tgagacatga ttgctttacc agatgttttt    480
gctgcaatgt aaattttgca gcaaaattcc tcagcaaact tttgtactga agatttactc    540
ctgaatggag aaggttgttt catcttgtga gtgagctaaa ctcatgtctt aatcgatgca    600
g                                                                    601

<210> SEQ ID NO 21
<211> LENGTH: 696
<212> TYPE: DNA
<213> ORGANISM: Solanum melongena

<400> SEQUENCE: 21
atagcatacc catcggaagt ggaagggctt gcagctcaac tccttaaagt tcaggacaac     60
ataccaatct gtgcttcaat aatctcacaa cgactggctc tttactcaat ggaaatggga    120
ccagaatggg taactaatca agtaaaagac cttgtcaaga acagagaggt gcttctagaa    180
gccttatctc ctttgggaaa gggagctgtt aaaggggag aaggtgccat ttacctgtgg    240
gcaaagctgc cagataaata catggacgac ttcaaagtag ttcactggct agctaagagg    300
catggagtag tcctgatccc tggaagttcc agcggttgtc caggttatgt tagggtctcc    360
tttggaggat tgatcgagaa ggactgtcga gcagctgcag aaaggctcag aaaaggtttg    420
gaagagctgg taaatagtgg aatggcgtca tgattctctc tgactaaaat ttagtgtcag    480
ctggttctcc tggacatcag tcatcaacaa tacaatgaca gacactttct atccttaata    540
attgaagggt tttaagcttt gcaacttgat cattggacat gcaagttaaa acttgccatt    600
```

```
ctgtatagtt tgaaatgaag tattcataga tacctacttt tcttaaatgg atgatggaag    660
tgtctcattt atctcagagc atatctcatt gaatca                              696
```

<210> SEQ ID NO 22
<211> LENGTH: 2000
<212> TYPE: DNA
<213> ORGANISM: Solanum melongena

<400> SEQUENCE: 22

```
gaaaataaaa ataatgcga cgtgcctcga agtttcgcaa ttcaagaatc cccgaaactt    60
catttgtttc ccaataacg ataaataaat aaataaatat cctctccatc caattgatca   120
ttacttgttt attactctct ctgtctcatt ttaattaaac ttgtgagatt aatatataca   180
tattaaaaaa aatattcgaa gacaaaattt atatcatact tttcactatt gcccttcgta   240
aaatcataaa tatatagtgt aacttatctc ttagaaaata taaagtttta ataaataaaa   300
gggcaaaaat aaaaaaaatc tcaaacattc atcctgaact tgaacaatt caattatttt   360 gaaccttgaa aaaagttttt aaaactttgt aaatatatat tactacttat agattgatta   420
ataatatatg tttagcctag aaaattaata aattattttt ttgttgtttg tatctattct   480
atttttatta ttatataata ctattcaata tttcatatat tttctaccac atttgtatta   540
aatatattca aaggataata ttatctttac tattatttat tgtttaaata aagtgtgtcc   600
aaattaaggt gaataactgt tgttagacgt agaaattaaa taccccacaa ggtatccata   660
ctgatatcac ttttttttta attagatatc tattatttga atgaatatga caagaatctt   720
ctcctttaaa atcaaattta aattaattga gattttgata tatagtgaat taaatatgaa   780
attaaaaaat aaaagtcaat acgagcccct agatcgaaga agtactaggg ggaggtgatt   840
agacatgata tgccgaaatt taatctcatt gaggacatga ccctagatag gtagacgtag   900
aggtcgcgaa ttagaatagt aggataattg gttggtaggg ttaggtggtt acctagtcag   960
ggggcctaac agggttgagt agtaatatt ttttttctag catgagttgt cattatttgt  1020
tgcttatatg ttaattgtat tatatttttg tattatcatg tgctttcttt tacttttgtc  1080
atatctagtc ctttctgagt atggatttta aaatgagggt tcccagaaac agtctctcta  1140
cttaggcagt gataaggtct gcatacattc taccctccct agactccact tatgagattt  1200
tactgattat attgttgttg ttgttgatat aatttttattt attctattca tgtaccaaaa  1260
gattcctgaa gagatcattt tataagaaat aacaataata atgaaataac tttataaata  1320
tgagataatt ttatctttttt ccaaccaaac aacccataaa tttagggaaa catttactcc  1380
ggaaatataa taattactcc atcaatttta atttatttat catatatttt tttaaaaact  1440 attttatat attttttttca tttcatttta tgtgacacac acatatttaa aaaaaacttt  1500
taaaatttta tggtttaaaa tcgctcttaa atatttgtat tgctgaaaat tatttcatta  1560
aaaataaaat ataaaaataa actatttcta atttttaataa gataatattt ttctaagaca  1620
atgaataaaa atttagaaag ccttcattat tttcttaaat cctattaaaa taggataaca  1680
gaaactgagg ttgtagaaca ttttaggggt tgaatttgat gaattggaca gtaggtgggg  1740
gatagggcaa gaaggcagca aaagggtga gaaaaacaga aagaaagaaa ggcatacaga  1800
gaatttcccc ctttttttc tcttaccaaa attaatggac aattcaactt ctaacagtca  1860
aacaaattcc taacatatgc agctataacg tggataaagc agaaaatac aaaaaaaagg  1920 tttccatctt tttggcattt gcctttgcca gctattacta tattattaat tcccagttgc  1980
```
agttagcagt ttcaagggtt 2000

<210> SEQ ID NO 23
<211> LENGTH: 1000
<212> TYPE: DNA
<213> ORGANISM: Solanum melongena

<400> SEQUENCE: 23

```
ttatacatat gtgtccattg gctgatgtat agctaagcta agaagatgcc ttccagttaa      60
gtggatatgc tatggtatat aacagaaata ttaggtctga atccagttac aacacttagc     120
tagttgctga tgaattaatc gagatatgca taagttattc accaaactcc tatagaaaaa     180
atttatgata gaaatatgcc attagagtca ctttagtagg atatgtgaaa gattttttc      240
tcaataaatt tctcttttcat tgttagctag ctattgttaa ccctcttggg actatagttg    300
atacaatgag ctacttagtc tttagattta tcaagagggg ctcaaactta tattgtggca    360
tatctaggtg tattttcgag tccacgtgaa cctacactag gctctcgaga ttatatatag    420
tagttttcac ttttttaaaaa tacttatata taaatgtgtg aatctacgct caaaatatta    480
tataatatga tgatgattag atgtaacttt tcgcaatagt gcactatttt ttcaaaaatt    540
ttaatatgcc tgaccaagta taaacctagt agatatgaat gattgataat tttcacttca    600
tgttttatg caaaatggat tcataaatac aagcgtactc tattaatagt aacaaataag     660
gaccaaatgt gtatcacttt ccaaagtaag gggtgaaatt caggaataaa acagccagct    720
aggatggagt tggattttac attttaagga ctttgttacc ttataataac caaaaacatt    780
ataaattaca ataataattt gttctataaa accgttttag tcaaaccagt caaaacttca    840
tctgtttttt ttttccttct tttgtcagag gccattactg ccaacccatg ataaagaaat    900
accgactttc ttttctcatt tttaaccttc tttcattttc ttgaattttg aactttgaac    960
tccatcatcc cgcctctctc acatttctat ctccattttc                         1000
```

<210> SEQ ID NO 24
<211> LENGTH: 9528
<212> TYPE: DNA
<213> ORGANISM: Solanum melongena

<400> SEQUENCE: 24

```
gaaaataaaa ataatgcga cgtgcctcga agtttcgcaa ttcaagaatc cccgaaactt      60
catttgtttc ccaaataacg ataaataaat aaataaatat cctctccatc caattgatca    120
ttacttgttt attactctct ctgtctcatt ttaattaaac ttgtgagatt aatatataca    180
tattaaaaaa aatattcgaa gacaaaattt atatcatact tttcactatt gcccttcgta    240
aaatcataaa tatatagtgt aacttatctc ttagaaaata taaagtttta ataaataaaa    300
gggcaaaaat aaaaaaaatc tcaaacattc atcctgaact ttgaacaatt caattatttt    360
gaaccttgaa aaaagttttt aaacttttgt aaatatatat tactacttat agattgatta    420
ataatatatg tttagcctag aaaattaata aattatttat ttgttgtttg tatctattct    480
atttttatta ttatataata ctattcaata tttcatatat tttctaccac atttgtatta    540
aatatattca aaggataata ttatctttac tattatttat tgtttaaata aagtgtgtcc    600
aaattaaggt gaataactgt tgttagacgt agaaattaaa tacccacaa ggtatcata     660
ctgatatcac ttttttttta attagatatc tattatttga atgaatatga caagaatctt    720
ctcctttaaa atcaaattta aattaattga gattttgata tatagtgaat taaatatgaa    780
attaaaaaat aaaagtcaat acgagcccctt agatcgaaga agtactaggg ggaggtgatt    840
```

```
agacatgata tgccgaaatt taatctcatt gaggacatga ccctagatag gtagacgtag    900
aggtcgcgaa ttagaatagt aggataattg gttggtaggg ttaggtggtt acctagtcag    960
ggggcctaac agggttgagt agtaatattt ttttttctag catgagttgt cattatttgt   1020
tgcttatatg ttaattgtat tatattttg tattatcatg tgctttcttt tacttttgtc    1080
atatctagtc ctttctgagt atggatttta aaatgagggt tcccagaaac agtctctcta   1140
cttaggcagt gataaggtct gcatacattc taccctccct agactccact tatgagattt   1200
tactgattat attgttgttg ttgttgatat aattttattt attctattca tgtaccaaaa   1260
gattcctgaa gagatcattt tataagaaat aacaataata atgaaataac tttataaata   1320
tgagataatt ttatctttt ccaaccaaac aacccataaa tttagggaaa catttactcc    1380
ggaaatataa taattactcc atcaatttta atttatttat catatatttt tttaaaaact   1440
attttatat atttttttca tttcatttta tgtgacacac acatatttaa aaaaaacttt    1500
taaaatttta tggtttaaaa tcgctcttaa atatttgtat tgctgaaaat tatttcatta   1560
aaaataaaat ataaaaataa actatttcta atttttaataa gataatattt ttctaagaca   1620
atgaataaaa atttagaaag ccttcattat tttcttaaat cctattaaaa taggataaca   1680
gaaactgagg ttgtagaaca tttagggt tgaatttgat gaattggaca gtaggtgggg    1740
gatagggcaa gaaggcagca aaagggtga gaaaaacaga aagaaagaaa ggcatacaga    1800
gaatttcccc ctttttttc tcttaccaaa attaatggac aattcaactt ctaacagtca    1860
aacaaattcc taacatatgc agctataacg tggataaagc agaaaatac aaaaaaagg     1920
tttccatctt tttggcattt gcctttgcca gctattacta tattattaat tcccagttgc   1980
agttagcagt ttcaagggtt gtccgtagca gtcaaattta ttcatattta acaaaaagat   2040
ccaattttta tattttttac aatcccttta tataggttcc aagcttttg taagattttc    2100
agaaagggaa aggccttttt tgctctgtgg gtaggtggat aagaactctt ttcttgaagg   2160
tagtgtttat tttattgttt ttactgagaa agaggaaatg ggttctttcg gaatgctcgc   2220
tagaagagct gttcttaccg atacaccagt tatggttcag gtaaattaca agatcctaga   2280
ttggatttct tgctcttttg tttggtttaa ggttctgtgc tttaatggga tatgttgttg   2340
ttgtgttttg caatcgatag atacaagaac tgattcgagg taataaagat tgtatttctc   2400
tagctcaggt ttgtttactt tctccaatgt ttgtttcatt ttgttttact atatcttagt   2460
tttattattc tacttttcat tgaatggttc aaaaagttga gaactttgat aaaattcatc   2520
tgttgttgtg atgtctttga agcctacata tcatcttatt gtgcctttcg aaatcttgat   2580
tagattgact tacattaaaa attggctaat tcattcttga agttatcaat ttcaatttt    2640
ttttcagtt gaaatatgaa ttgcttaata tttaagctag taattgggga aaaaaaatca    2700
aactggactt ccctcccatg taaagaatgt atttgcagat ggttttgaat gtgaaaaatg   2760
gagattatga gtgtccactg agctgggtgg gtataagggc ttgggtaggt gggtttcggg   2820
cctagagcac atgtgaagga ggtctactgg tacaagattg acattttctc tttccttaag   2880
ttcctctggt gattgcaaat aacataaatt gcctgagctt cttgttttgc gaagaaatct   2940
tctgaggttt ctcccatgat ctctggagtt acaaaattat tttgctagta tgttccatgc   3000
tcggttgtcc ttttcctgtg caaaagagt tataatactg ttcttttgat ctgttttttat   3060
ttgggttaac caagtatgat gtgatacaga agaaatctg ccgccctacc atgtgctgtg    3120
agtagtgatc cctttgtgtt atcctcctat tattggactg ttttacgaat gactggttct   3180
```

```
attatgatct ctgaggactg atctgttgac aagcaagttt tatcaacctc catctgaaaa    3240
aaaagaaagt ttaatcaacc taaacctacc aatggaagtt ttagaagttg tatagtttgc    3300
tggggttggg gcctggggaa tgagtgtgta cttatttgct tctttatgta ccttccagag    3360
agagtaaaca aaggaataga gttatctgtt gttggtggat cttttctgttg aagtgtgtag    3420 ttatattggt tttgcctgaa tatggttgtc catgttttcc atccatgtat cttggtacca    3480
tcttattttt ttctccgtct tacagggagt agtgtactgg caaccacctg cacaagcact    3540
tgaaaaggtg aaagaaatta tctgggaacc ttcagttagt cgctatggtg ctgatgaggg    3600
ccttcctgag cttagggagg cgttgatgca aaaggtatgg tctatcagct ggattactct    3660
aatactctgg ttttcatcgt atgggctggg tagtggaaca acattggag tggtgtaggg     3720 tgcttttgcc aggtgaaacg gtagttactg tcatgtatga agttggattc atttcatgtt    3780
ttcaaactat atcattcact tgttgagttt tggttttttac gttgtttggt ctaatacttt    3840
ctttgtgctc ttctccagtt gggtcatgaa ataacctcc ataaatcctc ggtgatggtt     3900
actgctggtg ctaatcaggt aaaatgttac ttttttacta ttcagtcatc tgaggatata    3960
gggtcagtca cttcacctct ttttcttacc tgccctgaat agtagtaggc tacctttctt    4020
tctcgccttt cttccatctt tttccagata aaggttggat gttttagaat gaaactgcgt    4080
tttggagatt tgtttgcttg agttagagtg ggttgagatt gattctacct tcatacaaga    4140
ttcatttgct ttgacagagg accagtattt gggtgcatgt ttacttcacc ttcctaagct    4200
attcttcagt tccccttttc ccttcattaa tgttcaaagt tgtctagttc atactagaaa    4260
cacggcaggg ctcctcttaa aaaagaaag tgcaatttc tacttttgc attgtcacaa       4320 tactaagaga tttcatctcc aaaaccagga agtgatgctt gtgagggaac gttttcctt     4380 tcttttacc cctctctcta tctctctctt aaatgaagat tcttagagt ttatgtggtc      4440 aagaaaccgt acagtacttt tcctgataaa tggtatggat acttctgaaa gaaaaataga   4500
actgcctcac tgataaatgg tgtgggattc cactaggtat gttgttgttg ttgttgtttt    4560
ctctatcatg atgcatacag tatgcagtgt atggaaaggt tggtgtgatt ttgagatttg    4620 gatttttattt tcttctgctt ctacccatct aaagattatt cttttctcg tgtgtatttt    4680 tcttgataaa aaagatcatt cttctgttgt gggcttattc agctccatgt tctaacttga    4740
tcaaaaaagt caaatgtgct ctcttttct tgtcttttcc gttttttgta ataagacctc     4800
ttttagtttt tgcatgttat cactgtactt ttgtatgtta ccattttcat gagatgacaa    4860
tcttgcaatg ggaacatatg cagcacaaaa ctctccattt agtatcatct gtcagaaaca    4920
tatagggaaa gaatctactg acatatctag catgctcaag cacttggccc tcacaatttt    4980
gtctgcaaaa tggaacttag ggattacttc gactactaat ttgagaatta attgcctaga    5040
ttttcaatga ctgagtaaat gatggtccaa ggggctcaga aagtatgagt acagacacat    5100
cattacgtac ctgtccatta cagagcagta ttctcttttt gaacaggaga attgtgtcct    5160
caatagtcct ccaaattaaa atcacaattt attgcaataa acaaattcgg atgaaacctt    5220
aagctgaatg aagatagtag agctatgtta atgagccatt tgtagagcaa tagagttgct    5280
acatgtatgg gtaaattaat tagtgtattg tctatattct ttgttagtga ctaatggact    5340
agctgtatcc ctatcactta gaaatcacta atggagtctc actgaattga ttccaggctt    5400
tcgtaaatgt cgttctcacc ctgtgtgatg ctggtgattc agttgttatg tttgcaccat    5460
actatttcaa tgcacacatg tcattccaga tgacaggtgt tactgatatt ctggtgggtc    5520
ctggtgatcc caagacactc catcctgatg caggtttgta agttcagatg atgttcattt    5580
```

```
tgtgataccc tcccattat taagactgct attcctttag tttccttaag actgattaca    5640
ctagatgttg tcatatacat ctctgttgtg tagcatgcat gttcaagttt gagggaacat    5700 ccttttatc tttgtcatct cagcactttg gaatatatat cataatcact aatcacatat    5760
gtactatgag ttactttttt cctctttgct tgaaatttat caaaaaactc catcttctct    5820
gaatctaaca ctacttgtgc agaaatcaac ttaagaagag gttgctgcag aagtagtgtt    5880
cagctttgta ttgcaagttg tgtaaatcat tcataatggt ctattagtct tgatttgtag    5940
aatgttgtct ggaaagcaat cattctgtgt ttttctcgt attggatgtc ctcaccccat     6000
ccccaccaga aagaaaccaa aaaaataat gaatttagta aacttatagt ttgacacttt     6060
gaagcataat gttaacctaa atattgcttc tattttgcat aatggacttg agagtttcaa    6120
aacattatct gccttcgtta tttgattgtt tatggattga tatattccat gatttctcaa    6180
ttttcagact ggttggagag tactttaaag aatactgtac caacaccaaa gctcgtcact    6240
gttgttaatc ctggcaatcc atcaggaaca tatatccccg agtctcttct taaggtctct    6300
atctcatctt tatagatatg aatgtattgg ttgaagtcat cagttattca aagtgcatta    6360
ctattctcat ctgattttta ctttattgaa acatcaacaa gttgcatttt gttcatgtag    6420
aggatatctg atatttgtaa gaaggcagga tgttggctcg taattgataa cacatatgag    6480
taagttactt tttctgttgc atacgaatct tttagtttct cattttaaat tgtgtactgg    6540
ttgttaataa ctggtgccga tatgttttct catccatgga tgaaagatga cattcttaga    6600
actaaagatg atgagggttg ttgaatggac taatcctgga atactttggg ttagaccagc    6660
aagagattat tgaataaacc aaggaaacag gtcgtttgca ttgcattgtg aggaaatctt    6720
tttgctttgt gaacctaaac ttgaactaaa tttgataggc aagaaaattt atggtatcct    6780
gggatctgtt gccatatttt gattgctgag aaggggagaa aggaaatagc taaggtgaaa    6840
gaatgatcag tctttgaatt catccaaatt ggcccacttg ttgctgtttg ttctcaatct    6900
ctagatggaa aataagccta gaaagttggc ttctcaacga gttagatagt taggacacat    6960
tactattgag tctttcctcc tccatgaatg tgaacatctt gttctgtcaa acatcatctc    7020
tgttccttct ttttcttgca acttttttgct ttacactctg cttgtcgttt tctatattcc    7080
tgaatgatat gttcttatat atatgttgta agttatttgc aggtatttca tgtatgataa    7140
tcggaaacat gtttgcatag aagcaaacca cattgtcaac atcttttcct tctctaaagc    7200
atatgggatg atgggatgga gagttggata tgtaagtgat gcttgttcta acttatatct    7260
agcaatgtaa taatattggg cagacaagtg attattattc tgctgggtga gcctcaacac    7320
aaccagaaaa tatacctggt taaagatga tttttctat gttttccgca actgcatctt      7380
cttgcctcat aaactccctc gtctttacct ttaaaccaaa aaccaaaaaa aatttaaaaa    7440
aattaaactg ttgtctttac ttatacctct ttttaaaacc agcatgtatg acacctttaa    7500
tcagtctctc tatccttgtc catcattaac ttttataacg aataatgttg cgtcctgtca    7560
tttgtgcctg gttgagtgat ctgctggaat tggatataaa attggcctca ataacaacca    7620
aaatacaagt gttctttttgc aacaaaaagg agttgttcca acagctaaga cttatggcat    7680
atgagacatg attgctttac cagatgtttt tgctgcaatg taaattttgc agcaaaattc    7740
ctcagcaaac ttttgtactg aagatttact cctgaatgga gaaggttgtt tcatcttgtg    7800
agtgagctaa actcatgtct taatcgatgc agatagcata cccatcggaa gtggaagggc    7860
ttgcagctca actccttaaa gttcaggaca acataccaat ctgtgcttca ataatctcac    7920
```

```
aacgactggc tctttactca atggaaatgg gaccagaatg ggtaactaat caagtaaaag    7980
accttgtcaa gaacagagag gtgcttctag aagccttatc tcctttggga aagggagctg    8040
ttaaaggggg agaaggtgcc atttacctgt gggcaaagct gccagataaa tacatggacg    8100
acttcaaagt agttcactgg ctagctaaga ggcatggagt agtcctgatc cctggaagtt    8160
ccagcggttg tccaggttat gttagggtct cctttggagg attgatcgag aaggactgtc    8220
gagcagctgc agaaaggctc agaaaaggtt tggaagagct ggtaaatagt ggaatggcgt    8280
catgattctc tctgactaaa atttagtgtc agctggttct cctggacatc agtcatcaac    8340
aatacaatga cagacacttt ctatccttaa taattgaagg ttttaagct ttgcaacttg     8400
atcattggac atgcaagtta aaacttgcca ttctgtatag tttgaaatga agtattcata    8460
gatacctact tttcttaaat ggatgatgga agtgtctcat ttatctcaga gcatatctca    8520
ttgaatcatt atacatatgt gtccattggc tgatgtatag ctaagctaag aagatgcctt    8580
ccagttaagt ggatatgcta tggtatataa cagaaatatt aggtctgaat ccagttacaa    8640
cacttagcta gttgctgatg aattaatcga gatatgcata agttattcac caaactccta    8700
tagaaaaaat ttatgataga aatatgccat tagagtcact ttagtaggat atgtgaaaga    8760
ttttttctc aataaatttc tctttcattg ttagctagct attgttaacc ctcttgggac     8820
tatagttgat acaatgagct acttagtctt tagatttatc aagagggct caaacttata    8880
ttgtggcata tctaggtgta ttttcgagtc acgtgaacc tacactaggc tctcgagatt     8940
atatatagta gtttacactt tttaaaaata cttatatata aatgtgtgaa tctacgctca    9000
aaatattata taatatgatg atgattagat gtaacttttc gcaatagtgc actatttttt    9060
caaaatttt aatatgcctg accaagtata aacctagtag atatgaatga ttgataattt     9120
tcacttcatg tttttatgca aaatggattc ataaatacaa gcgtactcta ttaatagtaa    9180
caaataagga ccaaatgtgt atcactttcc aaagtaaggg gtgaaattca ggaataaaac    9240
agccagctag gatggagttg gattttacat tttaaggact tgttacctt ataataacca     9300
aaaacattat aaattacaat aataatttgt tctataaaac cgttttagtc aaaccagtca    9360
aaacttcatc tgtttttttt ttccttcttt tgtcagaggc cattactgcc aacccatgat    9420
aaagaaatac cgactttctt ttctcatttt taaccttctt tcattttctt gaattttgaa    9480
ctttgaactc catcatcccg cctctctcac atttctatct ccatttc                 9528
```

<210> SEQ ID NO 25
<211> LENGTH: 4558
<212> TYPE: DNA
<213> ORGANISM: Solanum melongena

<400> SEQUENCE: 25

```
gtcagtcact tcacctcttt ttcttaccctg ccctgaatag tagtaggcta cctttctttc     60
tcgcctttct tccatctttt tccagataaa ggttggatgt tttagaatga aactgcgttt    120
tggagatttg tttgcttgag ttagagtggg ttgagattga ttctaccttc atacaagatt    180
catttgcttt gacagaggac cagtatttgg gtgcatgttt acttcacctt cctaagctat    240
tcttcagttc cccttttccc ttcattaatg ttcaaagttg tctagttcat actagaaaca    300
cggcagggct cctcttaaaa aagaaagtg caattttcta cttttgcat tgtcacaata      360
ctaagagatt tcatctccaa aaccaggaag tgatgcttgt gagggaacgt tttccctttc    420
ttttacccc tctctctatc tctctcttaa atgaagattt cttagagttt atgtggtcaa    480
gaaaccgtac agtactttc ctgataaatg gtatggatac ttctgaaaga aaaatagaac     540
```

```
tgcctcactg ataaatggtg tgggattcca ctaggtatgt tgttgttgtt gttgttttct    600
ctatcatgat gcatacagta tgcagtgtat ggaaaggttg gtgtgatttt gagatttgga    660
ttttattttc ttctgcttct acccatctaa agattattct ttttctcgtg tgtatttttc    720
ttgataaaaa agatcattct tctgttgtgg gcttattcag ctccatgttc taacttgatc    780
aaaaaagtca aatgtgctct cttttttctt g tcttttccgt tttttgtaat aagacctctt    840 ttagttttg catgttatca ctgtactttt gtatgttacc attttcatga gatgacaatc     900
ttgcaatggg aacatatgca gcacaaaact ctccatttag tatcatctgt cagaaacata    960
tagggaaaga atctactgac atatctagca tgctcaagca cttggccctc acaattttgt   1020
ctgcaaaatg gaacttaggg attacttcga ctactaaattt gagaattaat tgcctagatt    1080
ttcaatgact gagtaaatga tggtccaagg ggctcagaaa gtatgagtac agacacatca    1140
ttacgtacct gtccattaca gagcagtatt ctcttttga acaggagaat tgtgtcctca      1200
atagtcctcc aaattaaaat cacaattat tgcaataaac aaattcggat gaaaccttaa     1260
gctgaatgaa gatagtagag ctatgttaat gagccatttg tagagcaata gagttgctac    1320
atgtatgggt aaattaatta gtgtattgtc tatattcttt gttagtgact aatggactag    1380
ctgtatccct atcacttaga aatcactaat ggagtctcac tgaattgatt ccaggctttc    1440
gtaaatgtcg ttctcaccct gtgtgatgct ggtgattcag ttgttatgtt tgcaccatac    1500
tatttcaatg cacacatgtc attccagatg acaggtgtta ctgatattct ggtgggtcct    1560
ggtgatccca agacactcca tcctgatgca ggttttgtaag ttcagatgat gttcattttg    1620 tgatacccctc cccattatta agactgctat tcctttagtt tccttaagac tgattacact    1680
agatgttgtc atatacatct ctgttgtgta gcatgcatgt tcaagtttga gggaacatcc    1740
tttttatctt tgtcatctca gcactttgga atatatatca taatcactaa tcacatatgt    1800
actatgagtt actttttcc tctttgcttg aaattttatca aaaaactcca tcttctctga     1860
atctaacact acttgtgcag aaatcaactt aagaagaggt tgctgcagaa gtagtgttca    1920
gctttgtatt gcaagttgtg taaatcattc ataatggtct attagtcttg atttgtagaa    1980
tgttgtctgg aaagcaatca ttctgtgttt tttctcgtat tggatgtcct cacccccatcc    2040 ccaccagaaa gaaaccaaaa aaaataatga atttagtaaa cttatagttt gacactttga    2100
agcataatgt taacctaaat attgcttcta ttttgcataa tggacttgag agtttcaaaa    2160
cattatctgc cttcgttatt tgattgttta tggattgata tattccatga tttctcaatt    2220
ttcagactgg ttggagagta ctttaaagaa tactgtacca acaccaaagc tcgtcactgt    2280
tgttaatcct ggcaatccat caggaacata tatccccgag tctcttctta aggtctctat    2340
ctcatcttta tagatatgaa tgtattggtt gaagtcatca gttattcaaa gtgcattact    2400
attctcatct gatttttact ttattgaaac atcaacaagt tgcattttgt tcatgtagag    2460
gatatctgat atttgtaaga aggcaggatg ttggctcgta attgataaca catatgagta    2520 agttacttt tctgttgcat acgaatcttt tagtttctca ttttaaattg tgtactggtt      2580
gttaataact ggtgccgata tgttttctca tccatggatg aaagatgaca ttcttagaac    2640
taaagatgat gaggggttgtt gaatggacta atcctggaat acttttggtt agaccagcaa    2700
gagattattg aataaaccaa ggaaacaggt cgtttgcatt gcattgtgag gaaatctttt    2760
tgctttgtga acctaaactt gaactaaatt tgataggcaa gaaaatttat ggtatcctgg    2820
gatctgttgc catattttga ttgctgagaa ggggagaaag gaaatagcta aggtgaaaga    2880
```

| | |
|---|---|
| atgatcagtc tttgaattca tccaaattgg cccacttgtt gctgtttgtt ctcaatctct | 2940 |
| agatggaaaa taagcctaga aagttggctt ctcaacgagt tagatagtta ggacacatta | 3000 |
| ctattgagtc tttcctcctc catgaatgtg aacatcttgt tctgtcaaac atcatctctg | 3060 |
| ttccttcttt ttcttgcaac ttttttgctt cactctgct tgtcgttttc tatattcctg | 3120 |
| aatgatatgt tcttatatat atgttgtaag ttatttgcag gtatttcatg tatgataatc | 3180 |
| ggaaacatgt ttgcatagaa gcaaaccaca ttgtcaacat cttttccttc tctaaagcat | 3240 |
| atgggatgat gggatggaga gttggatatg taagtgatgc ttgttctaac ttatatctag | 3300 |
| caatgtaata atattgggca gacaagtgat tattattctg ctgggtgagc ctcaacacaa | 3360 |
| ccagaaaata tacctggtta aagatgatt tttttctatgt tttccgcaac tgcatcttct | 3420 |
| tgcctcataa actccctcgt ctttaccttt aaaccaaaaa ccaaaaaaaa tttaaaaaaa | 3480 |
| ttaaactgtt gtctttactt atacctcttt ttaaaaccag catgtatgac acctttaatc | 3540 |
| agtctctcta tccttgtcca tcattaactt ttataacgaa taatgttgcg tcctgtcatt | 3600 |
| tgtgcctggt tgagtgatct gctggaattg gatataaaat tggcctcaat aacaaccaaa | 3660 |
| atacaagtgt tcttttgcaa caaaaaggag ttgttccaac agctaagact tatggcatat | 3720 |
| gagacatgat tgctttacca gatgtttttg ctgcaatgta aattttgcag caaaattcct | 3780 |
| cagcaaactt ttgtactgaa gatttactcc tgaatggaga aggttgtttc atcttgtgag | 3840 |
| tgagctaaac tcatgtctta atcgatgcag atagcatacc catcggaagt ggaagggctt | 3900 |
| gcagctcaac tccttaaagt tcaggacaac ataccaatct gtgcttcaat aatctcacaa | 3960 |
| cgactggctc tttactcaat ggaaatggga ccagaatggg taactaatca agtaaaagac | 4020 |
| cttgtcaaga acagagaggt gcttctagaa gccttatctc ctttgggaaa gggagctgtt | 4080 |
| aaaggggag aaggtgccat ttacctgtgg gcaaagctgc cagataaata catggacgac | 4140 |
| ttcaaagtag ttcactggct agctaagagg catggagtag tcctgatccc tggaagttcc | 4200 |
| agcggttgtc caggttatgt tagggtctcc tttggaggat tgatcgagaa ggactgtcga | 4260 |
| gcagctgcag aaaggctcag aaaaggtttg gaagagctgg taaatagtgg aatggcgtca | 4320 |
| tgattctctc tgactaaaat ttagtgtcag ctggttctcc tggacatcag tcatcaacaa | 4380 |
| tacaatgaca gacactttct atccttaata attgaagggt tttaagcttt gcaacttgat | 4440 |
| cattggacat gcaagttaaa acttgccatt ctgtatagtt tgaaatgaag tattcataga | 4500 |
| tacctacttt tcttaaatgg atgatggaag tgtctcattt atctcagagc atatctca | 4558 |

<210> SEQ ID NO 26
<211> LENGTH: 227
<212> TYPE: DNA
<213> ORGANISM: Solanum melongena

<400> SEQUENCE: 26

| | |
|---|---|
| tatggtatat aacagaaata ttaggtctga atccagttac aacacttagc tagttgctga | 60 |
| tgaattaatc gagatatgca taagttattc accaaactcc tatagaaaaa atttatgata | 120 |
| gaaatatgcc attagagtca ctttagtagg atatgtgaaa gattttttc tcaataaatt | 180 |
| tctctttcat tgttagctag ctattgttaa ccctcttggg actatag | 227 |

<210> SEQ ID NO 27
<211> LENGTH: 1339
<212> TYPE: DNA
<213> ORGANISM: Solanum melongena

<400> SEQUENCE: 27

```
ttgggtcatg aaaataacct ccataaatcc tcggtgatgg ttactgctgg tgctaatcag      60
gtaaaatgtt acttttttac tattcagtca tctgaggata taggtatggt atataacaga     120
aatattaggt ctgaatccag ttacaacact tagctagttg ctgatgaatt aatcgagata     180
tgcataagtt attcaccaaa ctcctataga aaaatttat gatagaaata tgccattaga      240
gtcactttag taggatatgt gaaagatttt tttctcaata aatttctctt tcattgttag     300
ctagctattg ttaaccctct tgggactata gttgaatcat tatacatatg tgtccattgg     360
ctgatgtata gctaagctaa gaagatgcct tccagttaag tggatatgct atggtatata     420
acagaaatat taggtctgaa tccagttaca acacttagct agttgctgat gaattaatcg     480
agatatgcat aagttattca ccaaactcct atagaaaaaa tttatgatag aaatatgcca     540
ttagagtcac tttagtagga tatgtgaaag attttttttct caataaattt ctctttcatt    600
gttagctagc tattgttaac cctcttggga ctatagttga tacaatgagc tacttagtct     660
ttagattta caagagggg ctcaaactta ttgtggcat atctaggtgt attttcgagt        720
ccacgtgaac ctacactagg ctctcgagat tatatatagt agtttacact ttttaaaaat     780
acttatatat aaatgtgtga atctacgctc aaaatattat ataatatgat gatgattaga    840
tgtaacttttt cgcaatagtg cactatttttt tcaaaaattt taatatgcct gaccaagtat   900
aaacctagta gatgaatg attgataatt ttcacttcat gtttttatgc aaaatggatt      960
cataaataca agcgtactct attaatagta acaataagg accaaatgtg tatcactttc    1020
caaagtaagg ggtgaaattc aggaataaaa cagccagcta ggatggagtt ggattttaca   1080
ttttaaggac tttgttacct tataataacc aaaaacatta taaattacaa taataatttg   1140
ttctataaaa ccgttttagt caaccagtc aaaacttcat ctgttttttt tttccttctt    1200
ttgtcagagg ccattactgc caacccatga taaagaaata ccgactttct tttctcattt  1260
ttaaccttct ttcattttct tgaattttga actttgaact ccatcatccc gcctctctca  1320
catttctatc tccattttc                                                1339
```

<210> SEQ ID NO 28
<211> LENGTH: 394
<212> TYPE: PRT
<213> ORGANISM: Solanum lycopersicum

<400> SEQUENCE: 28

```
Met Gly Ser Phe Gly Met Leu Ala Arg Arg Ala Val Leu Thr Glu Thr
1               5                   10                  15

Pro Val Met Val Gln Ile Gln Glu Leu Val Arg Ser Asn Lys Gly Cys
            20                  25                  30

Ile Ser Leu Ala Gln Gly Val Val Tyr Trp Gln Pro Ala Gln Ala
        35                  40                  45

Leu Glu Lys Val Lys Glu Ala Ile Trp Glu Pro Ser Val Ser Arg Tyr
    50                  55                  60

Gly Ala Asp Glu Gly Leu Pro Glu Leu Arg Glu Ala Leu Met Gln Lys
65                  70                  75                  80

Leu Gly Arg Glu Asn Asn Leu His Lys Ser Ser Val Met Val Thr Ala
                85                  90                  95

Gly Ala Asn Gln Ala Phe Val Asn Val Leu Thr Leu Cys Asp Ala
            100                 105                 110

Gly Asp Ser Val Val Met Phe Ala Pro Tyr Tyr Phe Asn Ala His Met
        115                 120                 125
```

```
Ser Phe Gln Met Thr Gly Val Thr Asp Ile Leu Val Gly Pro Gly Asp
    130                 135                 140

Ala Lys Thr Leu His Pro Asp Ala Asp Trp Leu Glu Ser Thr Leu Lys
145                 150                 155                 160

Asn Thr Val Pro Thr Pro Lys Leu Val Thr Val Asn Pro Gly Asn
                165                 170                 175

Pro Ser Gly Thr Tyr Ile Pro Glu Ser Leu Leu Lys Arg Ile Ser Asp
                180                 185                 190

Ile Cys Lys Glu Ala Gly Cys Trp Leu Val Ile Asp Asn Thr Tyr Glu
            195                 200                 205

Tyr Phe Met Tyr Asp Asp Arg Lys His Val Cys Ile Glu Ala Asn His
    210                 215                 220

Ile Val Asn Ile Phe Ser Phe Ser Lys Ala Tyr Gly Met Met Gly Trp
225                 230                 235                 240

Arg Val Gly Tyr Ile Ala Tyr Pro Ser Glu Val Gly Leu Ala Val
                245                 250                 255

Gln Leu Leu Lys Val Gln Asp Asn Ile Pro Ile Cys Ala Ser Ile Ile
            260                 265                 270

Ser Gln Arg Leu Ala Leu Tyr Ser Met Glu Met Gly Pro Glu Trp Val
    275                 280                 285

Ala Asn Gln Val Lys Asp Leu Val Lys Asn Arg Glu Val Leu Gln Glu
290                 295                 300

Ala Leu Ser Pro Leu Gly Glu Gly Ala Val Lys Gly Glu Ala Ala
305                 310                 315                 320

Ile Tyr Leu Trp Ala Lys Leu Pro Asp Lys Tyr Met Asp Asp Phe Lys
                325                 330                 335

Val Val His Trp Leu Ala Lys Arg His Gly Val Val Leu Ile Pro Gly
            340                 345                 350

Ser Ser Ser Gly Cys Pro Gly Tyr Leu Arg Ile Ala Phe Gly Gly Leu
    355                 360                 365

Ile Glu Lys Asp Cys Arg Val Ala Ala Glu Arg Leu Arg Lys Gly Leu
    370                 375                 380

Glu Glu Leu Val Asn Phe Gly Met Val Ser
385                 390
```

<210> SEQ ID NO 29
<211> LENGTH: 1185
<212> TYPE: DNA
<213> ORGANISM: Solanum lycopersicum

<400> SEQUENCE: 29

```
atgggtctt ttggaatgct tgctagaagg gctgtgctta ccgagacacc agttatggtt    60
cagatacaag aactggttcg aagtaataaa ggttgtattt ctctagctca gggagtagtg   120
tactggcaac cacctgcgca agcacttgaa aaggtgaaag aagctatctg gaaccttca   180
gttagtcgct atggtgccga tgagggcctt cctgaactta gggaggcatt gatgcaaaag   240
ttgggtcgtg aaaataaccct acataaatct tcagtgatgg ttactgccgg tgcaaatcag   300
gctttcgtaa atgtcgttct cacactgtgt gatgctgggg attcggtcgt tatgtttgca   360
ccatactatt tcaatgcaca catgtcattc cagatgacag tgttaccga tattctggtg   420
ggtcctggtg atgcaaagac actccatcct gatgcagact ggttggagag tactctaaag   480
aatactgtac caaccccaaa gcttgtcact gttgttaatc ccggcaatcc atcaggaaca   540
tatattcctg agtcccttct taagaggata tctgatattt gtaaggaagc gggatgttgg   600
```

```
ctcgtaattg ataacacata tgagtatttt atgtatgatg atcgcaagca tgtttgcata    660
gaagcaaacc acattgtcaa catctttcc ttctccaaag catatgggat gatgggatgg    720
cgagttggat atatagcata cccatcggaa gtggaagggc ttgcagttca actccttaaa    780
gttcaggaca acataccgat ttgtgcttca ataatctcac aacgactggc tctctactca    840
atggaaatgg accagaatg ggtagctaat caagttaagg accttgtcaa gaacagagag    900
gtgctacaag aagccttatc tcctttggga gaggggctg ttaaaggggg agaagctgcc    960
atttacctgt gggcaaagct gccagataaa tacatggacg acttcaaagt agttcactgg   1020
ctagctaaga ggcatggagt agtcctgatc cctggaagtt ccagcggttg tccaggttat   1080
cttaggatcg cctttggagg attgattgag aaggactgtc gagtagctgc agaaaggctc   1140
agaaaaggtt tggaagagct ggtaaatttt ggaatggttt catga                   1185
```

<210> SEQ ID NO 30
<211> LENGTH: 394
<212> TYPE: PRT
<213> ORGANISM: Solanum pimpinellifolium

<400> SEQUENCE: 30

```
Met Gly Ser Phe Gly Met Leu Ala Arg Arg Ala Val Leu Thr Glu Thr
1               5                   10                  15
Pro Val Met Val Gln Ile Gln Glu Leu Val Arg Ser Asn Lys Gly Cys
            20                  25                  30
Ile Ser Leu Ala Gln Gly Val Val Tyr Trp Gln Pro Ala Gln Ala
        35                  40                  45
Leu Glu Lys Val Lys Glu Ala Ile Trp Glu Pro Ser Val Ser Arg Tyr
    50                  55                  60
Gly Ala Asp Glu Gly Leu Pro Glu Leu Arg Glu Ala Leu Met Gln Lys
65                  70                  75                  80
Leu Gly Arg Glu Asn Asn Leu His Lys Ser Ser Val Met Val Thr Ala
                85                  90                  95
Gly Ala Asn Gln Ala Phe Val Asn Val Leu Thr Leu Cys Asp Ala
            100                 105                 110
Gly Asp Ser Val Val Met Phe Ala Pro Tyr Tyr Phe Asn Ala His Met
        115                 120                 125
Ser Phe Gln Met Thr Gly Val Thr Asp Ile Leu Val Gly Pro Gly Asp
    130                 135                 140
Ala Lys Thr Leu His Pro Asp Ala Asp Trp Leu Glu Ser Thr Leu Lys
145                 150                 155                 160
Asn Thr Val Pro Thr Pro Lys Leu Val Thr Val Asn Pro Gly Asn
                165                 170                 175
Pro Ser Gly Thr Tyr Ile Pro Gly Ser Leu Leu Lys Arg Ile Ser Asp
            180                 185                 190
Ile Cys Lys Glu Ala Gly Cys Trp Leu Val Ile Asp Asn Thr Tyr Glu
        195                 200                 205
Tyr Phe Met Tyr Asp Asp Arg Lys His Val Cys Ile Glu Ala Asn His
    210                 215                 220
Ile Val Asn Ile Phe Ser Phe Ser Lys Ala Tyr Gly Met Met Gly Trp
225                 230                 235                 240
Arg Val Gly Tyr Ile Ala Tyr Pro Ser Glu Val Glu Gly Leu Ala Val
                245                 250                 255
Gln Leu Leu Lys Val Gln Asp Asn Ile Pro Ile Cys Ala Ser Ile Ile
            260                 265                 270
```

Ser Gln Arg Leu Ala Leu Tyr Ser Met Glu Met Gly Pro Glu Trp Val
         275                 280                 285

Ala Asn Gln Val Lys Asp Leu Val Lys Asn Arg Glu Val Leu Gln Glu
290                 295                 300

Ala Leu Ser Pro Leu Gly Glu Gly Ala Val Lys Gly Gly Ala Ala
305                 310                 315                 320

Ile Tyr Leu Trp Ala Lys Leu Pro Asp Lys Tyr Met Asp Asp Phe Lys
                325                 330                 335

Val Val His Trp Leu Ala Lys Arg His Gly Val Val Leu Ile Pro Gly
         340                 345                 350

Ser Ser Ser Gly Cys Pro Gly Tyr Leu Arg Ile Ala Phe Gly Gly Leu
         355                 360                 365

Ile Glu Lys Asp Cys Arg Val Ala Ala Glu Arg Leu Arg Lys Gly Leu
370                 375                 380

Glu Glu Leu Val Asn Phe Gly Met Val Ser
385                 390

<210> SEQ ID NO 31
<211> LENGTH: 1185
<212> TYPE: DNA
<213> ORGANISM: Solanum pimpinellifolium

<400> SEQUENCE: 31

| | | | | | |
|---|---|---|---|---|---|
| atggggtctt | ttggaatgct | tgctagaagg | gctgtgctta | ccgagacacc | agttatggtt | 60 |
| cagatacaag | aactggttcg | aagtaataaa | ggttgtattt | ctctagctca | gggagtagtg | 120 |
| tactggcaac | cacctgcgca | agcacttgaa | aaggtgaaag | aagctatctg | gaaccttca | 180 |
| gttagtcgct | atggtgccga | tgagggcctt | cctgaactta | gggaggcgtt | gatgcaaaag | 240 |
| ttgggtcgtg | aaaataacct | acataaatct | tcagtgatgg | ttactgccgg | tgcaaatcag | 300 |
| gctttcgtaa | atgtcgttct | cacactgtgt | gatgctgggg | attcggtcgt | tatgtttgca | 360 |
| ccatactatt | tcaatgcaca | catgtcattc | cagatgacag | tgttaccga | tattctggtg | 420 |
| ggtcctggtg | atgcaaagac | actccatcct | gatgcagact | ggttggagag | tactctaaag | 480 |
| aatactgtac | caaccccaaa | gcttgtcact | gttgttaatc | ccggcaatcc | atcaggaaca | 540 |
| tatattcctg | agtcccttct | taagaggata | tctgatattt | gtaaggaagc | gggatgttgg | 600 |
| ctcgtaattg | ataacacata | tgagtatttt | atgtatgatg | atcgcaagca | tgtttgcata | 660 |
| gaagcaaacc | acattgtcaa | catctttcc | ttctccaaag | catatgggat | gatgggatgg | 720 |
| cgagttggat | atatagcata | cccatcggaa | gtggaagggc | ttgcagttca | actccttaaa | 780 |
| gttcaggaca | cataccgat | ttgtgcttca | ataatctctc | aacgactggc | tctctactca | 840 |
| atggaaatgg | gaccagaatg | ggtagctaat | caagttaagg | accttgtcaa | gaacagagag | 900 |
| gtgctacaag | aagccttatc | tcctttggga | gaggggctg | ttaaaggggg | agaagctgcc | 960 |
| atttacctgt | gggcaaagct | gccagataaa | tacatgacg | acttcaaagt | agttcactgg | 1020 |
| ctagctaaga | ggcatggagt | agtcctgatc | cctggaagtt | ccagcggttg | tccaggttat | 1080 |
| cttaggatcg | cctttggagg | attgattgag | aaggactgtc | gagtagctgc | agaaaggctc | 1140 |
| agaaaaggtt | tggaagagct | ggtaaatttt | ggaatggttt | catga | | 1185 |

<210> SEQ ID NO 32
<211> LENGTH: 394
<212> TYPE: PRT
<213> ORGANISM: Solanum tuberosum phureja

<400> SEQUENCE: 32

Met Gly Ser Phe Gly Met Leu Ala Arg Arg Ala Val Leu Thr Glu Thr
1               5                   10                  15

Pro Val Met Val Gln Ile Gln Glu Leu Val Arg Gly Asn Lys Asp Cys
            20                  25                  30

Ile Ser Leu Ala Gln Gly Val Val Tyr Trp Gln Pro Ala Arg Ala
        35                  40                  45

Leu Glu Lys Val Lys Glu Ala Ile Trp Glu Pro Ser Val Ser Arg Tyr
50                  55                  60

Gly Ala Asp Glu Gly Leu Pro Glu Leu Arg Glu Ala Leu Ile Gln Lys
65                  70                  75                  80

Leu Gly Arg Glu Asn Asn Leu His Lys Ser Ser Val Met Val Thr Ala
                85                  90                  95

Gly Ala Asn Gln Ala Phe Val Asn Val Leu Thr Leu Cys Asp Ala
            100                 105                 110

Gly Asp Ser Val Val Met Phe Ala Pro Tyr Tyr Phe Asn Ala His Met
        115                 120                 125

Ser Phe Gln Met Thr Gly Val Thr Asp Ile Leu Val Gly Pro Gly Asp
    130                 135                 140

Ala Lys Thr Leu His Pro Asp Ala Asp Trp Leu Glu Ser Thr Leu Lys
145                 150                 155                 160

Asn Thr Val Pro Thr Pro Lys Leu Val Thr Val Asn Pro Gly Asn
                165                 170                 175

Pro Ser Gly Thr Tyr Ile Pro Glu Ser Leu Leu Lys Arg Ile Ser Asp
            180                 185                 190

Ile Cys Lys Glu Ala Gly Cys Trp Leu Val Ile Asp Asn Thr Tyr Glu
        195                 200                 205

Tyr Phe Met Tyr Asp Asp Arg Lys His Val Cys Ile Glu Ala Asn His
    210                 215                 220

Ile Val Asn Ile Phe Ser Phe Ser Lys Ala Tyr Gly Met Met Gly Trp
225                 230                 235                 240

Arg Val Gly Tyr Ile Ala Tyr Pro Ser Glu Val Gly Leu Ala Ala
                245                 250                 255

Gln Leu Leu Lys Val Gln Asp Asn Ile Pro Ile Cys Ala Ser Ile Ile
            260                 265                 270

Ser Gln Arg Leu Ala Leu Tyr Ser Met Glu Met Gly Pro Glu Trp Val
        275                 280                 285

Thr Asn Gln Val Lys Asp Leu Val Lys Asn Arg Glu Val Leu Gln Glu
    290                 295                 300

Ala Leu Ser Pro Leu Gly Glu Glu Ala Val Lys Gly Gly Glu Gly Ala
305                 310                 315                 320

Ile Tyr Leu Trp Ala Lys Leu Pro Asp Lys Tyr Met Asp Asp Phe Lys
                325                 330                 335

Val Val His Trp Leu Ala Lys Arg His Gly Ile Val Leu Ile Pro Gly
            340                 345                 350

Ser Ser Ser Gly Cys Pro Gly Tyr Val Arg Ile Ala Phe Gly Gly Leu
        355                 360                 365

Ile Glu Lys Asp Cys Arg Val Ala Ala Glu Arg Leu Arg Lys Gly Leu
    370                 375                 380

Glu Glu Leu Val Asn Ser Gly Met Val Ser
385                 390

<210> SEQ ID NO 33
<211> LENGTH: 1185

```
<212> TYPE: DNA
<213> ORGANISM: Solanum tuberosum phureja

<400> SEQUENCE: 33
atggggtctt ttggaatgct tgctagaaga gctgtgctta ccgagacacc agttatggtt      60
cagatacaag aactggttcg aggtaataaa gattgtattt ctctagctca gggagtagtg     120
tactggcaac cacctgcgcg agcacttgaa aaggtgaaag aagctatctg gaaccttca      180 gttagtcgct atggtgccga tgagggcctt cctgagctta gggaggcgtt gattcaaaag     240
ttgggtcgtg aaaataacct acataaatcc tcagtgatgg ttactgctgg tgcaaatcag     300
gctttcgtaa atgtcgttct cacactgtgt gatgctggcg attcggtcgt tatgtttgca     360
ccatactatt tcaatgcaca catgtcattc agatgacag tgttaccga tattctggtg       420 ggtcctggtg atgcaaagac actccatcct gatgcagact ggttggagag tactctaaag    480
aatactgtac caaccccaaa gcttgtcact gttgttaatc ccggcaatcc atcaggaacg     540
tatatccctg agtcccttct taagaggata tctgatattt gtaaggaagc gggatgttgg    600
ctcgtaattg ataacacata tgagtatttc atgtatgatg atcggaagca tgtttgcata    660
gaagcaaacc acattgtcaa catcttttcc ttctccaaag catatgggat gatgggatgg   720
cgagttggat atatagcata cccatcggaa gtggaagggc tcgcagctca actccttaaa   780
gttcaggaca catacccgat ttgtgcttca ataatctcac aacgactggc tctttactcc   840
atggaaatgg accagaatgg gtaactaat caagttaaag accttgtcaa gaacagagag    900
gtgcttcaag aagccttatc tcctttggga gaggaagctg ttaaaggggg agaaggtgcc   960
atttacctgt gggcaaagct gccagataaa tacatggacg acttcaaagt agttcactgg  1020
ttagctaaga ggcatggaat agttctgatc cctggaagtt ccagcggttg tccaggttat   1080
gttaggatcg cctttggagg attgattgag aaggactgtc gagtagctgc agaaaggctc  1140
agaaaaggtt tggaagagct ggtaaatagt ggaatggttt catga                  1185

<210> SEQ ID NO 34
<211> LENGTH: 394
<212> TYPE: PRT
<213> ORGANISM: Capsicum annuum

<400> SEQUENCE: 34

Met Gly Ser Phe Gly Met Leu Ala Arg Arg Ala Val Leu Thr Glu Thr
1               5                   10                  15

Pro Val Met Val Gln Ile Gln Glu Leu Val Arg Gly Leu Lys Asp Cys
                20                  25                  30

Val Ser Leu Ala Gln Gly Val Val Tyr Trp Gln Pro Pro Ala Gln Ala
            35                  40                  45

Leu Glu Lys Val Lys Glu Ile Ile Trp Glu Pro Ser Val Ser Arg Tyr
        50                  55                  60

Gly Ala Asp Glu Gly Leu Pro Glu Leu Arg Glu Ala Leu Lys Gln Lys
65                  70                  75                  80

Leu Gly Arg Glu Asn Asn Leu His Lys Ser Ser Val Met Val Thr Ser
                85                  90                  95

Gly Ala Asn Gln Ala Phe Val Asn Val Leu Ala Leu Cys Asp Ala
            100                 105                 110

Gly Asp Ser Val Val Met Phe Ala Pro Tyr Tyr Phe Asn Ala Tyr Met
        115                 120                 125

Ser Phe Gln Met Thr Gly Val Thr Asp Ile Leu Val Gly Ser Val Asp
    130                 135                 140
```

```
Ala Lys Thr Leu Gln Pro Asp Ala Asp Trp Leu Glu Ser Thr Leu Lys
145                 150                 155                 160

Asn Thr Val Pro Thr Pro Lys Leu Val Thr Val Val Asn Pro Gly Asn
                165                 170                 175

Pro Ser Gly Thr Tyr Ile Pro Glu Ser Leu Leu Lys Arg Ile Ser Asp
            180                 185                 190

Ile Cys Lys Glu Ala Gly Cys Trp Leu Val Val Asp Asn Thr Tyr Glu
        195                 200                 205

Tyr Phe Met Tyr Asp Asp Arg Lys His Val Cys Val Glu Ala Asn His
    210                 215                 220

Ile Val Asn Ile Phe Ser Phe Ser Lys Ala Tyr Gly Met Met Gly Trp
225                 230                 235                 240

Arg Val Gly Tyr Ile Ala Tyr Pro Ser Glu Val Asp Gly Leu Ala Ala
            245                 250                 255

Gln Leu Leu Lys Val Gln Asp Asn Ile Pro Ile Cys Ala Ser Ile Ile
            260                 265                 270

Ser Gln Arg Leu Ala Leu Tyr Ser Met Glu Val Gly Pro Glu Trp Val
    275                 280                 285

Ala Asp Gln Val Lys Asn Leu Val Lys Asn Arg Asp Val Leu Leu Glu
290                 295                 300

Ala Leu Ser Pro Leu Gly Glu Glu Ala Val Lys Gly Gly Gly Ala
305                 310                 315                 320

Leu Tyr Leu Trp Val Lys Leu Pro Asp Lys Tyr Ala Asp Asp Val Lys
                325                 330                 335

Val Val His Trp Leu Ala Lys Arg His Gly Val Val Leu Ile Pro Gly
            340                 345                 350

Ser Ser Cys Gly Cys Pro Gly Phe Val Arg Ile Ser Phe Gly Gly Leu
    355                 360                 365

Ile Glu Lys Asp Thr Ile Thr Ala Ala Lys Arg Leu Arg Lys Gly Leu
    370                 375                 380

Glu Glu Leu Leu Asp Ser Gly Met Asp Ser
385                 390

<210> SEQ ID NO 35
<211> LENGTH: 1185
<212> TYPE: DNA
<213> ORGANISM: Capsicum annuum

<400> SEQUENCE: 35
atgggttctt ttggaatgct agctagaaga gctgttctta cagaaacacc tgttatggtt      60
cagattcaag aattggtacg aggtcttaaa gattgtgttt ctttagctca gggagtagtg     120
tactggcaac cacctgcgca agcacttgaa aaggtgaaag aaattatctg gaaccttca      180 gttagtcgct atggtgccga tgagggcctt cctgagctca gggaggcgtt gaaacaaaag     240
ttgggtcgtg aaaataacct acataaatcc tcagtgatgg ttacttctgg tgcaaatcag     300
gcttttgtaa atgtcgttct cgcactgtgt gatgctggtg attcggttgt catgtttgca     360
ccatactatt tcaatgcata catgtcattc cagatgacgg tgttaccga tattctggtg      420 ggttctgttg atgcaaagac actccagcct gatgcagact ggttggagag tactctaaag     480
aatactgtac caaccccaaa gcttgtcact gttgttaatc ccggcaatcc gtcaggaaca     540
tatatccctg agtcccttct taagaggata tctgatattt gtaaggaagc gggatgttgg     600
ctcgtagttg ataacacata tgagtatttc atgtatgatg ataggaagca tgtttgcgta     660
```

```
gaagcaaacc acattgtaaa catctttttcc ttctctaaag catatgggat gatgggatgg    720
agagttggat atatagcata cccatcggaa gtggacgggc tcgcagctca actccttaaa    780
gttcaggaca acatacctat ttgtgcttcg ataatctcac aacgactggc tctttactca    840
atggaagtgg gaccagaatg ggtagctgat caagtaaaaa acctcgtcaa gaacagagat    900
gtacttctag aagctctctc tcctttggga gaggaagctg ttaaaggggg agaaggtgcc    960
ctttacctgt gggtaaagct gcccgataag tacgcggacg acgttaaagt agttcactgg   1020
ctagctaaga ggcatggagt agtcctgatc cccggcagtt cctgcggctg tccaggtttt   1080
gttagaatct ccttcggagg attgattgaa aaggacacta taacagctgc aaaaaggctc   1140
agaaaaggtt tggaagagct gttagatagt ggaatggatt catga                    1185
```

<210> SEQ ID NO 36
<211> LENGTH: 394
<212> TYPE: PRT
<213> ORGANISM: Malus domestica

<400> SEQUENCE: 36

```
Met Gly Ser Tyr Gly Gln Leu Ala Arg Arg Ala Val Glu Thr Asn Met
1               5                   10                  15

Pro Ile Met Val Gln Ile Gln Leu Val Arg Gly Ala Lys Asn Ala
            20                  25                  30

Val Ser Leu Ala Gln Gly Val Val Tyr Trp Gln Pro Lys Gln Ala
        35                  40                  45

Leu Asp Lys Val Arg Glu Leu Val Trp Glu Pro Ser Ile Ser Arg Tyr
    50                  55                  60

Gly Ala Asp Glu Gly Ile Pro Glu Leu Arg Glu Ala Leu Val Gln Lys
65                  70                  75                  80

Leu His Arg Glu Asn Lys Leu Tyr Lys Ser Val Met Val Thr Ala
                85                  90                  95

Gly Ala Asn Gln Ala Phe Val Asn Leu Ala Leu Thr Leu Cys Asp Ala
            100                 105                 110

Gly Asp Ser Val Val Met Phe Ala Pro Tyr Tyr Phe Asn Ala Tyr Met
        115                 120                 125

Ser Phe Gln Met Thr Gly Val Thr Asn Ile Leu Val Gly Pro Gly His
    130                 135                 140

Pro Lys Thr Leu Tyr Pro Asp Ala Asp Trp Leu Glu Lys Thr Leu Ser
145                 150                 155                 160

Glu Thr Lys Pro Thr Pro Lys Leu Val Thr Val Asn Pro Gly Asn
                165                 170                 175

Pro Ser Gly Thr Tyr Ile Pro Asp Ser Leu Leu Lys Arg Ile Ser Asp
            180                 185                 190

Ile Cys Arg Asp Ala Gly Ser Trp Leu Val Val Asp Asn Thr Tyr Glu
        195                 200                 205

Tyr Phe Met Tyr Asp Asp Leu Lys His Thr Cys Val Glu Gly Asn His
    210                 215                 220

Ile Ile Asn Ile Phe Ser Phe Ser Lys Ala Tyr Gly Met Met Gly Trp
225                 230                 235                 240

Arg Val Gly Tyr Ile Ala Tyr Pro Ser Glu Val Glu Gly Phe Gly Thr
                245                 250                 255

Gln Leu Leu Lys Val Gln Asp Asn Ile Pro Ile Cys Ala Ser Ile Ile
            260                 265                 270

Ser Gln His Leu Ala Leu His Ser Leu Glu Met Gly Pro Glu Trp Val
        275                 280                 285
```

```
Thr Glu Arg Val Lys Gly Leu Val Lys Asn Arg Glu Ile Val Leu Glu
    290                 295                 300

Ala Leu Ser Pro Leu Gly Asp Asn Ala Val Lys Gly Gly Glu Gly Ala
305                 310                 315                 320

Ile Tyr Leu Trp Ala Lys Leu Pro Asp Lys Tyr Val Asp Asp Lys
                325                 330                 335

Phe Val His Trp Leu Ala His Arg His Gly Val Val Ile Pro Gly
                340                 345                 350

Ser Ala Cys Gly Cys Pro Gly Asn Val Arg Ile Ser Phe Gly Gly Leu
    355                 360                 365

Val Glu Asp Asp Cys Lys Ala Ala Ala Glu Arg Leu Arg Arg Gly Phe
    370                 375                 380

Glu Glu Leu Ile Arg Asp Gly Met Val Glu
385                 390
```

<210> SEQ ID NO 37
<211> LENGTH: 1185
<212> TYPE: DNA
<213> ORGANISM: Malus domestica

<400> SEQUENCE: 37

```
atgggttcct atggacaact tgcaaggagg gctgtggaga ctaatatgcc gatcatggtt    60
cagatacagc agctggtccg aggagccaaa aatgccgtgt cactggctca gggagtggtt   120
tattggcaac cacccaagca ggcattggac aaggtgagag aacttgtttg ggagccttca   180
attagtcgtt acggtgctga tgaaggtata cctgaactca gggaggcatt ggtacaaaag   240
ttgcatcgtg aaaataagtt gtacaaatct tcagtgatgg ttactgcagg cgcaaatcag   300
gcatttgtga accttgctct tacattgtgt gatgccggag actctgtggt aatgtttgca   360
ccatactact tcaatgctta catgtccttt cagatgacag gagtcactaa tatactcgtg   420
ggtcctggtc acccaaagac actctaccca gatgcagact ggttggagaa aacgttatcc   480
gaaaccaaac caaccccaaa acttgttaca gttgttaatc ctggcaaccc aagtggaacc   540
tatattccgg attctcttct taagaggata tctgatatat gcagagatgc tggatcctgg   600
ctagttgtgg ataatacata tgagtatttt atgtatgatg atttgaaaca cacatgtgtg   660
gagggaaatc acataatcaa catttttttcc ttctcgaaag cttatgggat gatgggatgg   720
cgtgttggat atatagctta cccatcagaa gtagagggct ttggtaccca actcctcaaa   780
gttcaggata acattccatc tgtgcttca ataatttcgc agcaccttgc cctccactca   840
ttggaaatgg acccgaatg ggtcactgaa cgagtgaaag gtctagtcaa gaacagagaa   900
attgttctag aagctctctc tcccctcggg gacaatgctg ttaaaggtgg agaaggtgct   960
atatacttgt gggcaaagct tccggacaaa tatgtagatg atgataaatt tgttcactgg  1020
cttgctcaca ggcatggggt ggtggtgatc cccggaagtg cttgtggatg cccggggaat  1080
gtgagaatct ccttcggtgg cttggtggag gatgactgca agctgctgc agaaaggctg  1140
aggagagggt tcgaagagtt gatcagagat ggaatggtcg agtaa             1185
```

<210> SEQ ID NO 38
<211> LENGTH: 355
<212> TYPE: PRT
<213> ORGANISM: Solanum melongena

<400> SEQUENCE: 38

Met Gly Ser Phe Gly Met Leu Ala Arg Arg Ala Val Leu Thr Asp Thr

```
  1               5                  10                 15
Pro Val Met Val Gln Ile Gln Glu Leu Ile Arg Gly Asn Lys Asp Cys
                 20                 25                 30

Ile Ser Leu Ala Gln Gly Val Val Tyr Trp Gln Pro Ala Gln Ala
            35                 40                 45

Leu Glu Lys Val Lys Glu Ile Ile Trp Glu Pro Ser Val Ser Arg Tyr
        50                 55                 60

Gly Ala Asp Glu Gly Leu Pro Glu Leu Arg Glu Ala Leu Met Gln Lys
 65                 70                 75                 80

Leu Gly His Glu Asn Asn Leu His Lys Ser Ser Val Met Val Thr Ala
                85                 90                 95

Gly Ala Asn Gln Val Asn Glu Gly Val Gln Leu Lys Val Asn Cys Leu
            100                105                110

Gly Asn Tyr Met Pro Leu His Thr Tyr Tyr Glu Glu Arg Lys Phe Ser
        115                120                125

Asn Leu Ser Phe Asn Ala Tyr Gly Ser Asn Tyr Lys Ile Ser Ser Tyr
130                 135                140

Cys Pro Lys Ile His Gly Cys Met His Cys Thr Thr Ala Lys Ala Ala
145                 150                155                160

Gly Ser Glu Thr Arg Ser Ala Asp Arg Phe Gln His Gly Asn Pro Gln
                165                170                175

Gly Glu Glu Gln Glu Ser Ser Thr Tyr Phe Leu Cys Gly Glu Glu Met
            180                185                190

Pro Ala Ser Ala Gly Cys His Lys Ser Met Leu Gln His Phe Lys Trp
        195                200                205

Arg Leu Pro Arg Tyr Gln Ser Pro Lys Glu Glu Asp His Ser Ser
    210                215                220

Trp Lys Gln Leu Asn Lys Cys Val Ser Asp His Phe Ser Arg Leu Ser
225                 230                235                240

Val Ser Ile Ser Ser Gln Val Thr Thr Lys Glu Pro Ser Gln Leu Leu
                245                250                255

Arg Gln Glu Val Pro Thr Thr Arg Lys Asp Lys Arg Asn Gln Arg Phe
            260                265                270

Ser Lys Lys Arg His Ser Glu Ser Tyr Leu Cys Gly Thr Ile Asn Ile
        275                280                285

Asn Lys Val Gly Arg His Arg His Phe Ser Lys Gly Ser Thr Thr Met
    290                295                300

Gln Ser Ile Cys Leu Tyr Ile Glu Phe Thr Gly Cys Gly Ala Asn Lys
305                 310                315                320

Ala Ala Ile Lys Phe His Gly Asn Ala Pro Ala Arg Tyr His Thr Lys
                325                330                335

Tyr Ala Gly Asn Pro Cys Arg Leu Asp Cys Gly Gly Lys Leu Val Phe
            340                345                350

Ile Pro Asn
        355
```

<210> SEQ ID NO 39
<211> LENGTH: 27
<212> TYPE: DNA
<213> ORGANISM: Artificial Sequence
<220> FEATURE:
<223> OTHER INFORMATION: Antisense nucleotide

<400> SEQUENCE: 39
gccctcatca gcaccatagc gactaac                                    27

<210> SEQ ID NO 40
<211> LENGTH: 28
<212> TYPE: DNA
<213> ORGANISM: Artificial Sequence
<220> FEATURE:
<223> OTHER INFORMATION: Antisense nucleotide

<400> SEQUENCE: 40
gcaccatagc gactaactga aggttccc                                      28

<210> SEQ ID NO 41
<211> LENGTH: 26
<212> TYPE: DNA
<213> ORGANISM: Artificial Sequence
<220> FEATURE:
<223> OTHER INFORMATION: Sense nucleotide

<400> SEQUENCE: 41
ctgggaacct tcagttagtc gctatg                                        26

<210> SEQ ID NO 42
<211> LENGTH: 26
<212> TYPE: DNA
<213> ORGANISM: Artificial Sequence
<220> FEATURE:
<223> OTHER INFORMATION: Sense nucleotide

<400> SEQUENCE: 42
ttagtcgcta tggtgctgat gagggc                                        26

<210> SEQ ID NO 43
<211> LENGTH: 30
<212> TYPE: DNA
<213> ORGANISM: Artificial Sequence
<220> FEATURE:
<223> OTHER INFORMATION: Sense nucleotide

<400> SEQUENCE: 43
ctccccgggt ttttgctctg tgggtaggtg                                    30

<210> SEQ ID NO 44
<211> LENGTH: 26
<212> TYPE: DNA
<213> ORGANISM: Artificial Sequence
<220> FEATURE:
<223> OTHER INFORMATION: Antisense nucleotide

<400> SEQUENCE: 44
ctcgagctcc aggagaacca gctgac                                        26

<210> SEQ ID NO 45
<211> LENGTH: 24
<212> TYPE: DNA
<213> ORGANISM: Artificial Sequence
<220> FEATURE:
<223> OTHER INFORMATION: Sense nucleotide

<400> SEQUENCE: 45
aagagctgtt cttaccgata cacc                                          24

<210> SEQ ID NO 46
<211> LENGTH: 23
<212> TYPE: DNA
<213> ORGANISM: Artificial Sequence
<220> FEATURE:

<223> OTHER INFORMATION: Antisense nucleotide

<400> SEQUENCE: 46
gattagcacc agcagtaacc atc                                           23

<210> SEQ ID NO 47
<211> LENGTH: 20
<212> TYPE: DNA
<213> ORGANISM: Artificial Sequence
<220> FEATURE:
<223> OTHER INFORMATION: Sense nucleotide

<400> SEQUENCE: 47 caacccatc tctcactcgt                                                20

<210> SEQ ID NO 48
<211> LENGTH: 20
<212> TYPE: DNA
<213> ORGANISM: Artificial Sequence
<220> FEATURE:
<223> OTHER INFORMATION: Antisense nucleotide

<400> SEQUENCE: 48
aacaatgtga cagcccacaa                                               20

<210> SEQ ID NO 49
<211> LENGTH: 24
<212> TYPE: DNA
<213> ORGANISM: Artificial Sequence
<220> FEATURE:
<223> OTHER INFORMATION: Sense nucleotide

<400> SEQUENCE: 49
tcatctgagg atatagggtc agtc                                          24

<210> SEQ ID NO 50
<211> LENGTH: 23
<212> TYPE: DNA
<213> ORGANISM: Artificial Sequence
<220> FEATURE:
<223> OTHER INFORMATION: Antisense nucleotide

<400> SEQUENCE: 50
ccaaatctca aaatcacacc aac                                           23

<210> SEQ ID NO 51
<211> LENGTH: 24
<212> TYPE: DNA
<213> ORGANISM: Artificial Sequence
<220> FEATURE:
<223> OTHER INFORMATION: Sense nucleotide

<400> SEQUENCE: 51
agtcatctga ggatataggt atgg                                          24

<210> SEQ ID NO 52
<211> LENGTH: 29
<212> TYPE: DNA
<213> ORGANISM: Artificial Sequence
<220> FEATURE:
<223> OTHER INFORMATION: Antisense nucleotide

<400> SEQUENCE: 52
ggtaacaaag tccttaaaat gtaaaatcc                                     29

```
<210> SEQ ID NO 53
<211> LENGTH: 22
<212> TYPE: DNA
<213> ORGANISM: Artificial Sequence
<220> FEATURE:
<223> OTHER INFORMATION: Sense nucleotide

<400> SEQUENCE: 53
tcatttgttt cccaaataac ga                                              22

<210> SEQ ID NO 54
<211> LENGTH: 29
<212> TYPE: DNA
<213> ORGANISM: Artificial Sequence
<220> FEATURE:
<223> OTHER INFORMATION: Antisense nucleotide

<400> SEQUENCE: 54
ctccccgggc tagcgagcat tccgaaaga                                       29

<210> SEQ ID NO 55
<211> LENGTH: 2173
<212> TYPE: DNA
<213> ORGANISM: Solanum melongena

<400> SEQUENCE: 55
tcatttgttt cccaaataac gataaataaa taaataaata tcctctccat ccaattgatc     60
attacttgtt tattactctc tctgtctcat tttaattaaa cttgtgagat taatatatac    120
atattaaaaa aaatattcga agacaaaatt tatatcatac ttttcactat tgcccttcgt    180
aaaatcataa atatatagtg taacttatct cttagaaaat ataaaagttt aataaataaa    240
agggcaaaaa taaaaaaaat ctcaaacatt catcctgaac tttgaacaat tcaattattt    300
tgaaccttga aaaaagtttt aaaactttg taaatatata ttactactta tagattgatt    360
aataatatat gtttagccta gaaaattaat aaattattta tttgttgttt gtatctattc    420 tattttatt attatataat actattcaat atttcatata ttttctacca catttgtatt    480
aaatatattc aaaggataat attatcttta ctattattta ttgtttaaat aaagtgtgtc    540
caaattaagg tgaataactg ttgttagacg tagaaattaa atacccaca aggtatccat    600 actgatatca ctttttttt aattagatat ctattatttg aatgaatatg acaagaatct    660
tctcctttaa aatcaaattt aaattaattg agattttgat atatagtgaa ttaaatatga    720
aattaaaaaa taaagtcaa tacgagccct tagatcgaag aagtactagg gggaggtgat    780
tagacatgat atgccgaaat ttaatctcat tgaggacatg accctagata ggtagacgta    840
gaggtcgcga attagaatag taggataatt ggttggtagg gttaggtggt tacctagtca    900
gggggcctaa cagggttgag tagtaatatt ttttttcta gcatgagttg tcattatttg    960
ttgcttatat gttaattgta ttatatttt gtattatcat gtgctttctt ttactttgt    1020 catatctagt cctttctgag tatggatttt aaaatgaggg ttcccagaaa cagtctctct    1080
acttaggcag tgataaggtc tgcatacatt ctaccctccc tagactccac ttatgagatt    1140
ttactgatta tattgttgtt gttgttgata tatatttatt tattctattc atgtaccaaa    1200
agattcctga agagatcatt ttataagaaa taacaataat aatgaaataa ctttataaat    1260
atgagataat tttatctttt tccaaccaaa caacccataa atttagggaa acatttactc    1320
cggaaatata ataattactc catcaatttt aatttattta tcatatattt ttttaaaaac    1380 tattttata tatttttttc atttcatttt atgtgacaca cacatattta aaaaaaactt    1440
```

```
ttaaaattttt atggtttaaa atcgctctta aatatttgta ttgctgaaaa ttatttcatt    1500
aaaaataaaa tataaaaata aactatttct aattttaata agataatatt tttctaagac    1560
aatgaataaa aatttagaaa gccttcatta ttttcttaaa tcctattaaa ataggataac    1620
agaaactgag gttgtagaac atttaggggg ttgaatttga tgaattggac agtaggtggg    1680
ggatagggca agaaggcagc aaaaagggtg agaaaacag aaagaaagaa aggcatacag     1740
agaatttccc cctttttttt ctcttaccaa aattaatgga caattcaact tctaacagtc    1800
aaacaaattc ctaacatatg cagctataac gtggataaag cagaaaaata caaaaaaaag   1860
gtttccatct ttttggcatt tgcctttgcc agctattact atattattaa ttcccagttg    1920
cagttagcag tttcaagggt tgtccgtagc agtcaaattt attcatattt aacaaaaaga   1980
tccaattttt atatttttta caatcccttt ataaggttc caagcttttt gtaagatttt     2040
cagaaaggga aaggcctttt ttgctctgtg ggtaggtgga taagaactct tttcttgaag    2100
gtagtgttta ttttattgtt tttactgaga aagaggaaat gggttctttc ggaatgctcg    2160
ctagcccggg gag                                                       2173
```

<210> SEQ ID NO 56
<211> LENGTH: 35
<212> TYPE: DNA
<213> ORGANISM: Artificial Sequence
<220> FEATURE:
<223> OTHER INFORMATION: Sense nucleotide

<400> SEQUENCE: 56

```
ctccccggga agcttgcagg atgttggctc gtaat                               35
```

<210> SEQ ID NO 57
<211> LENGTH: 32
<212> TYPE: DNA
<213> ORGANISM: Artificial Sequence
<220> FEATURE:
<223> OTHER INFORMATION: Antisense nucleotide

<400> SEQUENCE: 57

```
ctcctcgagc tcaacataac ctggacaacc gc                                  32
```

<210> SEQ ID NO 58
<211> LENGTH: 522
<212> TYPE: DNA
<213> ORGANISM: Artificial Sequence
<220> FEATURE:
<223> OTHER INFORMATION: PCR product

<400> SEQUENCE: 58

```
ctccccggga agcttgcagg atgttggctc gtaattgata acacatatga gtatttcatg     60
tatgataatc ggaaacatgt ttgcatagaa gcaaaccaca ttgtcaacat ctttccttc    120 tctaaagcat atgggatgat gggatggaga gttggatata tagcataccc atcggaagtg   180
gaagggcttg cagctcaact ccttaaagtt caggacaaca taccaatctg tgcttcaata   240
atctcacaac gactggctct ttactcaatg gaaatgggac cagaatgggt aactaatcaa   300
gtaaaagacc ttgtcaagaa cagagaggtg cttctagaag ccttatctcc tttgggaaag   360
ggagctgtta aaggggggaga aggtgccatt tacctgtggg caaagctgcc agataaatac   420
atggacgact tcaaagtagt tcactggcta gctaagaggc atggagtagt cctgatccct   480
ggaagttcca gcggttgtcc aggttatgtt gagctcgagg ag                       522
```

<210> SEQ ID NO 59
<211> LENGTH: 35
<212> TYPE: DNA
<213> ORGANISM: Artificial Sequence
<220> FEATURE:
<223> OTHER INFORMATION: Sense nucleotide

<400> SEQUENCE: 59
ctccccggga tcgatggagg cattgatgca aaagt                               35

<210> SEQ ID NO 60
<211> LENGTH: 32
<212> TYPE: DNA
<213> ORGANISM: Artificial Sequence
<220> FEATURE:
<223> OTHER INFORMATION: Antisense nucleotide

<400> SEQUENCE: 60
ctcctcgagc tctcccatca tcccatatgc tt                                  32

<210> SEQ ID NO 61
<211> LENGTH: 523
<212> TYPE: DNA
<213> ORGANISM: Artificial Sequence
<220> FEATURE:
<223> OTHER INFORMATION: PCR product

<400> SEQUENCE: 61
ctccccggga tcgatggagg cattgatgca aaagttgggt cgtgaaaata acctacataa    60
atcttcagtg atggttactg ccggtgcaaa tcaggctttc gtaaatgtcg ttctcacact   120
gtgtgatgct ggggattcgg tcgttatgtt tgcaccatac tatttcaatg cacacatgtc   180
attccagatg acaggtgtta ccgatattct ggtgggtcct ggtgatgcaa agacactcca   240
tcctgatgca gactggttgg agagtactct aaagaatact gtaccaaccc caaagcttgt   300
cactgttgtt aatcccggca atccatcagg aacatatatt cctgagtccc ttcttaagag   360
gatatctgat atttgtaagg aagcgggatg ttggctcgta attgataaca catatgagta   420
ttttatgtat gatgatcgca agcatgtttg catagaagca aaccacattg tcaacatctt   480
ttccttctcc aaagcatatg ggatgatggg agagctcgag gag                     523

<210> SEQ ID NO 62
<211> LENGTH: 1908
<212> TYPE: DNA
<213> ORGANISM: Solanum lycopersicum

<400> SEQUENCE: 62
tctgttcctc attaatattc tgattttatt aatcaagatt gtgagtacca atttgttact    60
cattgatttt cctctcctaa gatttattca tgattcgatg gccgttaatg gtgtattttt   120
caactaggat gatttagatt tgacttctat atgaatattt catgacttt atgaaatatt   180 tcgagatcgt gattttttcta tgaattttt gagatgtctt ttaagagaat ttagcagtct   240
ttatatagac agaaactagg atttatgatt gagtagcttc cgaaaattct aataaaatcc   300
caacttgaat cgaacatatt tgttaaatc ctacgaaatt tcaccgtata cagatctctt   360 taaaaaatc cattccctata agggaagaac aaatatataa cgattctatt cgtataagga   420
ataagttcct atacttatta gaggagtgga taagcttctc agtatcaaca tgcatgtttg   480
atgtctcttc aaatatggta tatcttttta tcatctattt gttatttgg tataacttaa   540 tataagtgtg tcctactttt tcactctcca tttttttttg tctctttttct ttcattactt   600

| aaaatgttcc atgcaaaata ttaaatataa caaattttat tacctttta acactcttaa | 660 |
| aaagaaatta tttaatatat ttagttgact cttctcattt catttacata agtggatttt | 720 |
| tttacttctt ttatgtaatt taaaataggt aaattgttca gagttcaaaa taaatgtttt | 780 |
| gaatttttcc tttttttga cttttattta aattttaggt tataatttc aagatgtata | 840 |
| tatttatagt tttactttga attatttata ttttaaaaat agtataaaag gataaaattg | 900 |
| aaaaattatg tttaaacttt ttttaaagaa aatatttatt acttcacaag tttacttaat | 960 |
| ataaaataaa gaaagtaaca tctatcgact tccttgtgtc tagtaaataa cacaaggaag | 1020 |
| tgatagtata tacgaaaaag aaattccatt tgtataaagg agtacttctc tttgaaatgc | 1080 |
| atcttacact ttcctaattc aatttaatca agattcaata tatttacgag attcaataaa | 1140 |
| aattagaaaa gtaaaagtaa atgcatgctc ttattactca cgggataact ttgtccatct | 1200 |
| tgttttgta caaaacgatt ctttaagagg tcattttta ttaaggatac acaataatta | 1260 |
| ttttagacaa tgtgaaatct ctctcaatca attattccat ctcgatgaca tataaccccca | 1320 |
| taatatttaa ggaaacataa ttaatttatt tgtcttactt tatttttgcg ttcgaccaag | 1380 |
| aattggacaa gtaggttggg agatagggtc aactaaggca caaaagggaa aggcaaagag | 1440 |
| agaaatttgc ttcattttct ctacaaaaat taatactaat ggatacttca acttctaaca | 1500 |
| gtcaaacaaa ttcctaacat attacttact gtaatgctat aacgtgtatg aaacacaaaa | 1560 |
| atacagaaag gggttacgtc attatggcct ttggcttttg ccttttgcca gctactacta | 1620 |
| tattattaat tcctagttgc agttagcagt ttcaagggtt gtccgtagca gtcaaattta | 1680 |
| ttcattaatt taacaaaaag atccaatttt tatatttttt acgatctcat tctatataag | 1740 |
| ttccaatctt tttgcaagat cttttcagaa aaggaaaaaa ggcctttttt actttctggg | 1800 |
| taggtggata agaactctta tctttgaagg gttttttttt tttttattg ttttagagag | 1860 |
| aaaagaggaa atggggtctt tggaatgct tgctagaagc ccggggag | 1908 |

<210> SEQ ID NO 63
<211> LENGTH: 27
<212> TYPE: DNA
<213> ORGANISM: Artificial Sequence
<220> FEATURE:
<223> OTHER INFORMATION: Sense nucleotide

<400> SEQUENCE: 63
tctgttcctc attaatattc tgatttt                                    27

<210> SEQ ID NO 64
<211> LENGTH: 33
<212> TYPE: DNA
<213> ORGANISM: Artificial Sequence
<220> FEATURE:
<223> OTHER INFORMATION: Antisense nucleotide

<400> SEQUENCE: 64
ctccccgggc ttctagcaag cattccaaaa gac                              33

<210> SEQ ID NO 65
<211> LENGTH: 22
<212> TYPE: DNA
<213> ORGANISM: Artificial Sequence
<220> FEATURE:
<223> OTHER INFORMATION: Sense nucleotide

<400> SEQUENCE: 65
ttgctagaag ggctgtgctt ac                                          22

<210> SEQ ID NO 66
<211> LENGTH: 22
<212> TYPE: DNA
<213> ORGANISM: Artificial Sequence
<220> FEATURE:
<223> OTHER INFORMATION: Antisense nucleotide

<400> SEQUENCE: 66
gcaccatagc gactaactga ag                                              22

<210> SEQ ID NO 67
<211> LENGTH: 20
<212> TYPE: DNA
<213> ORGANISM: Artificial Sequence
<220> FEATURE:
<223> OTHER INFORMATION: Sense nucleotide

<400> SEQUENCE: 67
aagtggttgc cttcccttgc                                                 20

<210> SEQ ID NO 68
<211> LENGTH: 24
<212> TYPE: DNA
<213> ORGANISM: Artificial Sequence
<220> FEATURE:
<223> OTHER INFORMATION: Antisense nucleotide

<400> SEQUENCE: 68
gttttgtctc tggtttcttc tgcc                                            24

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
tggagccacc cgcagttcga aaag                                            24

<210> SEQ ID NO 70
<211> LENGTH: 28
<212> TYPE: DNA
<213> ORGANISM: Artificial Sequence
<220> FEATURE:
<223> OTHER INFORMATION: Sense nucleotide

<400> SEQUENCE: 70
ctctctagat tgtttccca ataacga                                          28

<210> SEQ ID NO 71
<211> LENGTH: 29
<212> TYPE: DNA
<213> ORGANISM: Artificial Sequence
<220> FEATURE:
<223> OTHER INFORMATION: Antisense nucleotide

<400> SEQUENCE: 71
ctccccgggt cgattgcaaa acacaacaa                                       29

<210> SEQ ID NO 72
<211> LENGTH: 2313
<212> TYPE: DNA
<213> ORGANISM: Artificial Sequence
<220> FEATURE:

<223> OTHER INFORMATION: PCR product

<400> SEQUENCE: 72

| | | | | | |
|---|---|---|---|---|---|
| ctctctagat | ttgtttccca | aataacgata | aataaataaa | taaatatcct | ctccatccaa | 60 |
| ttgatcatta | cttgtttatt | actctctctg | tctcatttta | attaaacttg | tgagattaat | 120 |
| atatacatat | taaaaaaaat | attcgaagac | aaaatttata | tcatactttt | cactattgcc | 180 |
| cttcgtaaaa | tcataaatat | atagtgtaac | ttatctctta | gaaatataaa | aagtttaata | 240 |
| aataaaaggg | caaaaataaa | aaaaatctca | aacattcatc | ctgaactttg | aacaattcaa | 300 |
| ttattttgaa | ccttgaaaaa | aagttttaaa | actttgtaaa | tatatattac | tacttataga | 360 |
| ttgattaata | atatatgttt | agcctagaaa | attaataaat | tatttatttg | ttgtttgtat | 420 |
| ctattctatt | tttattatta | tataatacta | ttcaatattt | catatatttt | ctaccacatt | 480 |
| tgtattaaat | atattcaaag | gataatatta | tctttactat | tatttattgt | ttaaataaag | 540 |
| tgtgtccaaa | ttaaggtgaa | taactgttgt | tagacgtaga | aattaaatac | cccacaaggt | 600 |
| atccatactg | atatcacttt | ttttttaatt | agatatctat | tatttgaatg | aatatgacaa | 660 |
| gaatcttctc | ctttaaaatc | aaatttaaat | taattgagat | tttgatatat | agtgaattaa | 720 |
| atatgaaatt | aaaaaataaa | agtcaatacg | agcccttaga | tcgaagaagt | actagggga | 780 |
| ggtgattaga | catgatatgc | cgaaatttaa | tctcattgag | gacatgaccc | tagataggta | 840 |
| gacgtagagg | tcgcgaatta | aatagtagg | ataattggtt | ggtagggtta | ggtggttacc | 900 |
| tagtcagggg | gcctaacagg | gttgagtagt | aatattttt | tttctagcat | gagttgtcat | 960 |
| tatttgttgc | ttatatgtta | attgtattat | attttttgtat | tatcatgtgc | tttcttttac | 1020 |
| ttttgtcata | tctagtcctt | tctgagtatg | gattttaaaa | tgagggttcc | cagaaacagt | 1080 |
| ctctctactt | aggcagtgat | aaggtctgca | tacattctac | cctccctaga | ctccacttat | 1140 |
| gagattttac | tgattatatt | gttgttgttg | ttgatataat | tttatttatt | ctattcatgt | 1200 |
| accaaaagat | tcctgaagag | atcattttat | aagaaataac | aataataatg | aaataacttt | 1260 |
| ataaatatga | gataattttta | tcttttttcca | accaaacaac | ccataaattt | agggaaacat | 1320 |
| ttactccgga | aatataataa | ttactccatc | aattttaatt | tatttatcat | atattttttt | 1380 |
| aaaaactatt | tttatatatt | tttttcattt | cattttatgt | gacacacaca | tatttaaaaa | 1440 |
| aaacttttaa | aattttatgg | tttaaaatcg | ctcttaaata | tttgtattgc | tgaaaattat | 1500 |
| ttcattaaaa | ataaaatata | aaaataaaact | atttctaatt | ttaataagat | aatatttttc | 1560 |
| taagacaatg | aataaaaatt | tagaaagcct | tcattatttt | cttaaatcct | attaaaatag | 1620 |
| gataacagaa | actgaggttg | tagaacattt | tagggggttga | atttgatgaa | ttggacagta | 1680 |
| ggtgggggat | agggcaagaa | ggcagcaaaa | agggtgagaa | aaacagaaag | aaagaaaggc | 1740 |
| atacagagaa | tttcccccctt | ttttttctct | taccaaaatt | aatggacaat | tcaacttcta | 1800 |
| acagtcaaac | aaattcctaa | catatgcagc | tataacgtgg | ataaagcaga | aaaatacaaa | 1860 |
| aaaaaggttt | ccatcttttt | ggcatttgcc | tttgccagct | attactatat | tattaattcc | 1920 |
| cagttgcagt | tagcagtttc | aagggttgtc | cgtagcagtc | aaatttattc | atatttaaca | 1980 |
| aaaagatcca | atttttatat | tttttacaat | ccctttatat | aggttccaag | cttttttgtaa | 2040 |
| gattttcaga | aagggaaagg | ccttttttgc | tctgtgggta | ggtggataag | aactcttttc | 2100 |
| ttgaaggtag | tgtttatttt | attgtttta | ctgagaaaga | ggaaatgggt | tctttcggaa | 2160 |
| tgctcgctag | aagagctgtt | cttaccgata | caccagttat | ggttcaggta | aattacaaga | 2220 |
| tcctagattg | gatttcttgc | tcttttgttt | ggtttaaggt | tctgtgcttt | aatgggatat | 2280 | gttgttgttg tgttttgcaa tcgacccggg gag         2313

<210> SEQ ID NO 73
<211> LENGTH: 1209
<212> TYPE: DNA
<213> ORGANISM: Artificial Sequence
<220> FEATURE:
<223> OTHER INFORMATION: Sequence based on Solanum melongena cDNA

<400> SEQUENCE: 73

| | |
|---|---|
| atgggttctt tcggaatgct cgctagaaga gctgttctta ccgatacacc agttatggtt | 60 |
| cagatacaag aactgattcg aggtaataaa gattgtattt ctctagctca gggagtagtg | 120 |
| tactggcaac cacctgcaca agcacttgaa aaggtgaaag aaattatctg gaaccttca | 180 |
| gttagtcgct atggtgctga tgagggcctt cctgagctta gggaggcgtt gatgcaaaag | 240 |
| ttgggtcatg aaaataacct ccataaatcc tcggtgatgg ttactgctgg tgctaatcag | 300 |
| gctttcgtaa atgtcgttct caccctgtgt gatgctggtg attcagttgt tatgtttgca | 360 |
| ccatactatt tcaatgcaca catgtcattc cagatgacag gtgttactga tattctggtg | 420 |
| ggtcctggtg atcccaagac actccatcct gatgcagact ggttggagag tacttaaag | 480 |
| aatactgtac caacaccaaa gctcgtcact gttgttaatc ctggcaatcc atcaggaaca | 540 |
| tatatccccg agtctcttct taagaggata tctgatattt gtaagaaggc aggatgttgg | 600 |
| ctcgtaattg ataacacata tgagtatttc atgtatgata atcggaaaca tgtttgcata | 660 |
| gaagcaaacc acattgtcaa catctttttcc ttctctaaag catatgggat gatgggatgg | 720 |
| agagttggat atatagcata cccatcggaa gtggaagggc ttgcagctca actccttaaa | 780 |
| gttcaggaca atataccaat ctgtgcttca ataatctcac aacgactggc tctttactca | 840 |
| atggaaatgg gaccagaatg ggtaactaat caagtaaaag accttgtcaa gaacagagag | 900 |
| gtgcttctag aagccttatc tccttttggga agggagctg ttaaaggggg agaaggtgcc | 960 |
| atttacctgt gggcaaagct gccagataaa tacatggacg acttcaaagt agttcactgg | 1020 |
| ctagctaaga ggcatggagt agtcctgatc cctggaagtt ccagcggttg tccaggttat | 1080 |
| gttagggtct cctttggagg attgatcgag aaggactgtc gagcagctgc agaaaggctc | 1140 |
| agaaaaggtt tggaagagct ggtaaatagt ggaatggcgt catggagcca cccgcagttc | 1200 |
| gaaaagtga | 1209 |

<210> SEQ ID NO 74
<211> LENGTH: 1209
<212> TYPE: DNA
<213> ORGANISM: Artificial Sequence
<220> FEATURE:
<223> OTHER INFORMATION: Sequence based on Solanum melongena cDNA

<400> SEQUENCE: 74

| | |
|---|---|
| atggggtcct ttggcatgct agcgcgtcgt gcagtgttga ccgatacccc ggtcatggtt | 60 |
| cagattcagg agttgatccg cggtaacaaa gattgcatta gcctcgctca aggggtagtg | 120 |
| tattggcaac ctccagcaca agcgttggaa aaggtgaagg agatcatctg ggagccgagt | 180 |
| gtgagccgct atggtgcgga tgaaggactg ccggaactgc gtgaagccct gatgcaaaaa | 240 |
| ctcggccacg aaaacaatct gcacaaaagc tcagtgatgg tgacggcagg tgcaaatcag | 300 |
| gcgtttgtta atgtggtcct gacactgtgt gatgcaggtg actctgtggt catgtttgcg | 360 |
| ccgtactact ttaacgccca catgagcttc cagatgactg gcgtaaccga catcctggta | 420 |

```
ggtccaggtg accccaaaac gctgcatcct gatgcggatt ggctcgaatc gacgctgaaa    480
aacacagttc ccaccccgaa acttgtcact gttgtcaatc cgggtaatcc gagtggcacg    540
tacattccgg aaagtctgtt aaaacggatt ccgacatct gcaaaaaagc cggctgttgg     600
ttggtgatag ataacaccta tgagtacttt atgtatgaca atcgcaaaca tgtgtgcatt    660
gaagcgaacc acattgtaaa catcttctcg ttctcaaagg cgtatggtat gatgggctgg    720
agagttggat atatcgccta tccgtcggaa gtggaagggt tagccgcaca actgcttaaa    780
gtccaggata acattcccat atgcgcttct atcatttccc agcgtttagc cctgtactcc    840
atggaaatgg gaccagagtg ggtgaccaac caggtcaagg atctggtaaa aaatcgcgaa    900
gttctgcttg aagcgttgtc tcctctcgga aaaggcgccg ttaagggcgg ggaaggtgcg    960
atttacctgt gggctaaact gccggataag tatatgacg acttcaaagt tgtccattgg    1020
ctggcgaaac gtcatggcgt ggttctgatt ccgggtagca gctcaggctg tccaggctat   1080
gtgcgcgttt cgtttggcgg gttaatcgag aaagattgtc gtgctgcagc tgaacgactt   1140
cgcaaaggcc tggaagagtt agtaaatagc ggtatggcca gttggtctca tccgcagttc   1200
gaaaaataa                                                           1209

<210> SEQ ID NO 75
<211> LENGTH: 16
<212> TYPE: DNA
<213> ORGANISM: Artificial Sequence
<220> FEATURE:
<223> OTHER INFORMATION: Synthetic nucleotide

<400> SEQUENCE: 75
taccatggcg ggatcc                                                    16

<210> SEQ ID NO 76
<211> LENGTH: 17
<212> TYPE: DNA
<213> ORGANISM: Artificial Sequence
<220> FEATURE:
<223> OTHER INFORMATION: Synthetic nucleotide

<400> SEQUENCE: 76
taggccgcat aagcccg                                                   17

<210> SEQ ID NO 77
<211> LENGTH: 1242
<212> TYPE: DNA
<213> ORGANISM: Artificial Sequence
<220> FEATURE:
<223> OTHER INFORMATION: Synthetic sequence

<400> SEQUENCE: 77
taccatggcg ggatccatgg ggtcctttgg catgctagcg cgtcgtgcag tgttgaccga     60 tacccccggtc atggttcaga ttcaggagtt gatccgcggt aacaaagatt gcattagcct   120
cgctcaaggg gtagtgtatt ggcaacctcc agcacaagcg ttggaaaagg tgaaggagat   180
catctgggag ccgagtgtga gccgctatgg tgcggatgaa ggactgccgg aactgcgtga   240
agccctgatg caaaaactcg gccacgaaaa caatctgcac aaaagctcag tgatggtgac   300
ggcaggtgca aatcaggcgt tgttaatgt ggtcctgaca ctgtgtgatg caggtgactc    360
tgtggtcatg tttgcgccgt actactttaa cgcccacatg agcttccaga tgactggcgt   420
aaccgacatc ctggtaggtc caggtgaccc caaaacgctg catcctgatg cggattggct   480
cgaatcgacg ctgaaaaaca cagttcccac cccgaaactt gtcactgttg tcaatccggg   540
```

```
taatccgagt ggcacgtaca ttccggaaag tctgttaaaa cggatttccg acatctgcaa      600
aaaagccggc tgttggttgg tgatagataa cacctatgag tactttatgt atgacaatcg      660
caaacatgtg tgcattgaag cgaaccacat tgtaaacatc ttctcgttct caaaggcgta      720
tggtatgatg ggctggagag ttggatatat cgcctatccg tcggaagtgg aagggttagc      780
cgcacaactg cttaaagtcc aggataacat tcccatatgc gcttctatca tttcccagcg      840
tttagccctg tactccatgg aaatgggacc agagtgggtg accaaccagg tcaaggatct      900
ggtaaaaaat cgcgaagttc tgcttgaagc gttgtctcct ctcggaaaag gcgccgttaa      960
gggcggggaa ggtgcgattt acctgtgggc taaactgccg gataagtata tggacgactt     1020
caaagttgtc cattggctgg cgaaacgtca tggcgtggtt ctgattccgg gtagcagctc     1080
aggctgtcca ggctatgtgc gcgtttcgtt tggcgggtta atcgagaaag attgtcgtgc     1140
tgcagctgaa cgacttcgca aaggcctgga agagttagta aatagcggta tggccagttg     1200
gtctcatccg cagttcgaaa aataataggc cgcataagcc cg                        1242
```

<210> SEQ ID NO 78
<211> LENGTH: 7
<212> TYPE: PRT
<213> ORGANISM: Artificial sequence
<220> FEATURE:
<223> OTHER INFORMATION: Sequence from expression vector

<400> SEQUENCE: 78

Thr Ser Thr Met Ala Gly Ser
1               5

PARTHENOCARPY REGULATION GENE AND USE THEREOF

TECHNICAL FIELD

The present invention relates to a parthenocarpy regulatory gene and a method for producing a plant with the use of the parthenocarpy regulatory gene, and the like.

BACKGROUND ART

In solanaceous plants such as eggplant and tomato, in general, pollination is normally carried out after anthesis, and a fruit is enlarged after seeds are formed in the fruit. On the other hand, a trait with which a fruit is normally enlarged and matured without pollination and seed formation is called parthenocarpy. This trait is significantly advantageous in fields of agriculture, horticulture, and the like in terms of harvesting fruits without carrying out, for example, work such as pollination induction with the use of flower visiting insects or fructification induction by hormone drug application.

Conventionally, with regard to solanaceous plants, it has been known that change in amount of auxin, which is one of phytohormones, in an ovary is one of factors for inducing parthenocarpy. For example, it is known that parthenocarpy is induced by applying a synthetic auxin to an eggplant flower or the like (Non-patent Literature 1).

With regard to a synthesis mechanism, in a plant, of indole acetic acid (hereinafter, referred to as "IAA") which is one of natural auxin, there have been prior study in which *Arabidopsis* is used as an experimental model plant. In *Arabidopsis*, the existence of an IPyA pathway is known as a biosynthetic pathway. In addition, the existence of a TAM pathway, an IAM pathway, and the like is presumed. It is becoming clear that many genes are relevant to these pathways and, recently, not only a gene which encodes an enzyme that positively functions with respect to IAA synthesis but also the existence of a gene which encodes an enzyme that negatively functions have been reported. For example, Non-patent Literature 2 discloses VAS1 which catalyzes reaction to generate tryptophan by transferring an amino group from methionine to an indole pyruvic acid (IPyA) in an IPyA pathway which is one of IAA synthesis pathways of *Arabidopsis*. Thus, VAS1 encodes an enzyme that negatively functions with respect to IAA synthesis.

Non-patent Literature 3 discloses that parthenocarpy is induced in eggplant by placenta-specific and ovule-specific expression of iaaM which is an IAA synthesis enzyme relevant to an IAM pathway that (i) is one of the IAA synthesis pathways and (ii) exists in a bacterium. Note that an experiment in Non-patent Literature 3 was carried out with the use of a plant in which excessive expression of bacterium-derived iaaM of *Pseudomonas* was caused under control by a snapdragon-derived promotor.

CITATION LIST

Non-Patent Literature

[Non-Patent Literature 1]
Nothmann et al. (1975) J. Hort. Sci. 50: 23-27
[Non-Patent Literature 2]
Zheng et al. (2013) Nature Chem. Biol. 9: 244-246
[Non-Patent Literature 3]
Rotino et al., (1997) Nature Biotechnology 15: 1398-1401

SUMMARY OF INVENTION

Technical Problem

As disclosed in Non-patent Literatures 2 and 3, existence of genes relevant to IAA synthesis has been known. However, the IAA synthesis mechanism is a highly complicated pathway, and it is predictable that many unknown genes play significant roles in the IAA synthesis pathway. Further, clarification of functions of the unknown genes in the IAA synthesis may lead to a highly useful technique in fields of agriculture, horticulture, and the like. Depending on cultivation conditions or cultivar lines, phenotypic expression of parthenocarpy can become unstable, and therefore it is sometimes difficult to evaluate parthenocarpy if the evaluation is based only on appearance of a plant. Moreover, in order to evaluate parthenocarpy, much manpower and time are required for emasculation before anthesis, evaluation of fruit set, and the like.

The present invention is accomplished in view of the problems, and its object is (i) to identify a novel gene that is responsible for parthenocarpy and (ii) to provide use of the novel gene.

Solution to Problem

In order to attain the object, the present invention encompasses any one of the following aspects:
<1> A method for evaluating parthenocarpy of a plant, the method including the step of: checking whether or not expression of a parthenocarpy regulatory gene, which includes a polynucleotide recited in any of (1) through (4) below, is inhibited in the plant; or checking whether or not a function of a polypeptide, which is encoded by the parthenocarpy regulatory gene, is inhibited in the plant.
(1) A polynucleotide that encodes a polypeptide having an amino acid sequence represented by SEQ ID NO: 1,
(2) a polynucleotide that encodes a polypeptide (i) having a sequence identity of 75% or higher relative to the amino acid sequence represented by SEQ ID NO: 1 and (ii) having a parthenocarpy regulatory activity,
(3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and
(4) a polynucleotide that (i) is hybridized with a polynucleotide, which has a sequence complementary to the polynucleotide recited in the above (1), under a stringent condition and (ii) encodes a polypeptide having a parthenocarpy regulatory activity.
<2> A parthenocarpy regulatory gene that includes a polynucleotide recited in any of (1) through (4) below.
(1) A polynucleotide that encodes a polypeptide having an amino acid sequence represented by SEQ ID NO: 1,
(2) a polynucleotide that encodes a polypeptide (i) having a sequence identity of 75% or higher relative to the amino acid sequence represented by SEQ ID NO: 1 and (ii) having a parthenocarpy regulatory activity,
(3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and (4) a polynucleotide that (i) is hybridized with a polynucleotide, which has a sequence complementary to the polynucleotide recited in the above (1), under a stringent condition and (ii) encodes a polypeptide having a parthenocarpy regulatory activity.

<3> A polypeptide recited in any of (1) through (4) below.
(1) A polypeptide having an amino acid sequence represented by SEQ ID NO: 1,
(2) a polypeptide (i) having a sequence identity of 75% or higher relative to the amino acid sequence represented by SEQ ID NO: 1 and (ii) having a parthenocarpy regulatory activity,
(3) a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and
(4) a polypeptide that (i) is encoded by a polynucleotide which is hybridized, under a stringent condition, with a polynucleotide that has a sequence complementary to a polynucleotide for encoding the polypeptide recited in the above (1) and (ii) has a parthenocarpy regulatory activity.

<4> A plant which is a parthenocarpic plant and in which (i) expression of a parthenocarpy regulatory gene, which includes a polynucleotide recited in any of (1) through (4) below, is inhibited or (ii) a function of a polypeptide, which is encoded by the parthenocarpy regulatory gene, is inhibited.
(1) A polynucleotide that encodes a polypeptide having an amino acid sequence represented by SEQ ID NO: 1,
(2) a polynucleotide that encodes a polypeptide (i) having a sequence identity of 75% or higher relative to the amino acid sequence represented by SEQ ID NO: 1 and (ii) having a parthenocarpy regulatory activity,
(3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and
(4) a polynucleotide that (i) is hybridized with a polynucleotide, which has a sequence complementary to the polynucleotide recited in the above (1), under a stringent condition and (ii) encodes a polypeptide having a parthenocarpy regulatory activity.

Advantageous Effects of Invention

It is possible to evaluate parthenocarpy of a plant or to produce a parthenocarpic plant by using, as an indicator or a target, a gene or a polypeptide encoded by the gene.

BRIEF DESCRIPTION OF DRAWINGS

FIG. 1A and FIG. 1B present views illustrating parthenocarpy of a parthenocarpic eggplant line "PCSS" in Example 1 of the present invention.

FIG. 3A and FIG. 3B present views illustrating a correspondence between a phenotype (i.e., presence/absence of parthenocarpy) and a marker genotype in generations after crossbreeding of a parthenocarpic eggplant line PCSS and a non-parthenocarpic eggplant line TN-43 in Example 1 of the present invention.

DESCRIPTION OF EMBODIMENTS

Figure 2:
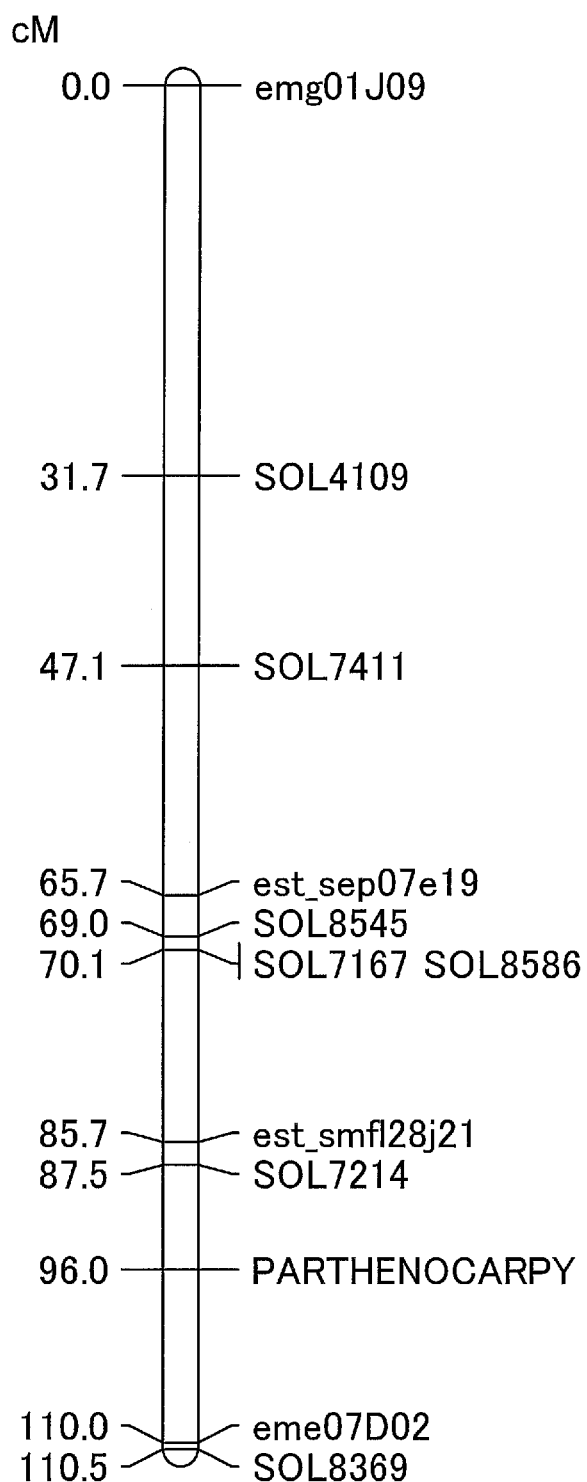
FIG. 2 is a view illustrating a linkage map of a region in which a parthenocarpy responsible gene A is located in Example 1 of the present invention.

The following description will discuss an embodiment of the present invention. Note that the present invention is not limited to this.

Definitions of Terms

In this specification, "polynucleotide" can be reworded as "nucleic acid" or "nucleic acid molecule", and is intended to be a polymer of nucleotides. Moreover, "base sequence" can be reworded as "nucleic acid sequence" or "nucleotide sequence", and is intended to be a sequence of deoxyribonucleotide or a sequence of ribonucleotide, unless otherwise particularly noted.

In this specification, "polypeptide" can be reworded as "protein".

In this specification, "parthenocarpy (parthenocarpic)" is intended to be a trait of a plant whose fruit is enlarged without pollination.

In this specification, "heterozygote (heterozygous)" is intended to be a state in which different allelic genes are at corresponding gene loci on respective homologous chromosomes, and "homozygote (homozygous)" is intended to be a state in which identical allelic genes are at corresponding gene loci on respective homologous chromosomes.

In this specification, "eggplant" is a concept that encompasses, in the broad sense, cultivated species "*Solanum* (hereinafter, referred to as "S") *melongena*" and wild species "*S. incanum*", "*S. torvum*", "*S. nigrum*", "*S. aethiopicum*", "*S. macrocarpon*", and "*S. quitoense*", and is intended to be "*S. melongena*" in the narrow sense.

In this specification, "tomato" is a concept that encompasses, in the broad sense, cultivated species "*S. lycopersicum*" and wild species "*S. cheesmaniae*, *S. chilense*, *S. chmielewskii*, *S. galapagense*, *S. habrochaites*, *S. lycopersicoides*, *S. neorickii*, *S. pennellii*, *S. peruvianum*, and *S. pimpinellifolium*", and is intended to be "*S. lycopersicum*" in the narrow sense.

In this specification, "pepper" is a concept that encompasses, in the broad sense, cultivated species "*Capsicum* (hereinafter, referred to as "C") *annuum*", and wild species "*C. pubescens*", "*C. baccatum*", "*C. chinense*", and "*C. frutescens*", and is intended to be "*C. annuum*" in the narrow sense. Moreover, "pepper" is a concept that encompasses plants called by names other than "pepper", e.g., horticultural crops called "piment", "paprika", and "sweet pepper".

In this specification, "A and/or B" is a concept that includes both "A and B" and "A or B", and can be reworded as at least one of A and B.

In this specification, a wording "polynucleotides are complementary to each other" is synonymous with "base sequences of respective polynucleotides are complementary to each other".

[1. Parthenocarpy Regulatory Gene]

A parthenocarpy regulatory gene in accordance with the present invention encodes a polypeptide that has an activity (i.e., a parthenocarpy regulatory activity) to regulate at least parthenocarpy. The polypeptide "that has an activity to regulate parthenocarpy" indicates that expression of a trait, i.e., parthenocarpy is inhibited by the presence of the polypeptide, that is, parthenocarpy is negatively regulated. Moreover, in a case where expression of the parthenocarpy regulatory gene of the present invention is inhibited or an activity of a polypeptide encoded by the parthenocarpy regulatory gene is inhibited, a plant shows a parthenocarpy trait or has a predisposition of the trait even though parthenocarpy is not shown.

Moreover, an example of the parthenocarpy regulatory gene of the present invention encodes an amino group transferase which catalyzes reaction to synthesize tryptophan by transferring an amino group of amino acid to IPyA. In a case where the transferase has an activity, expression of parthenocarpy trait is inhibited (i.e., having parthenocarpy regulatory activity), whereas in a case where the activity of the transferase is inhibited, a plant shows a parthenocarpy trait or has a predisposition of the trait even though parthenocarpy is not shown.

The parthenocarpy regulatory gene of the present invention includes any of polynucleotides described in the following (1) through (4):

(1) A polynucleotide that encodes a polypeptide having an amino acid sequence represented by SEQ ID NO: 1.
(2) A polynucleotide that encodes a polypeptide (i) having a sequence identity of 75% or higher relative to the amino acid sequence represented by SEQ ID NO: 1 and (ii) having a parthenocarpy regulatory activity. Note that the sequence identity of the amino acid sequence is preferably 80% or higher, more preferably 85% or higher, more preferably 90% or higher, further preferably 95% or higher, particularly preferably 96% or higher, 97% or higher, 98% or higher, or 99% or higher. For example, a mutant gene derived from eggplant and a homologous gene derived from a plant other than eggplant are encompassed in this scope.
(3) A polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity. Note that the number of amino acids which are substituted, deleted, inserted, and/or added is more preferably 1 to 78, more preferably 1 to 43, more preferably 1 to 39, more preferably 1 to 19, further preferably 1 to 15, particularly preferably 1 to 11, 1 to 5, or 6.

Note that the deletion, substitution, and/or addition of amino acids can be, for example, (i) carried out by artificially introducing a mutation(s) by the use of site-directed mutagenesis such as a Kunkel method (Kunkel et al. (1985): Proc. Natl. Acad. Sci. USA, vol. 82. p 488-) or (ii) derived from a naturally occurring similar mutant polypeptide.

(4) A polynucleotide that (i) is hybridized with a polynucleotide, which has a sequence complementary to the polynucleotide described in the above (1), under a stringent condition and (ii) encodes a polypeptide having a parthenocarpy regulatory activity. Note that the stringent condition is, for example, a condition described in Reference Literature [Molecular cloning—a Laboratory manual 2nd edition (Sambrook et al., 1989)]. Specifically, the stringent condition is, for example, a condition in which the polynucleotide is hybridized by being constantly heated, at 65° C. for 8 to 16 hours together with a probe, in a solution that contains 6×SSC (composition of 1×SSC: 0.15 M of sodium chloride, 0.015 M of sodium citrate, pH 7.0), 0.5% of SDS, 5×Denhardt's solution, and 100 mg/mL of herring sperm DNA. Note that the polynucleotide preferably has a sequence identity of 75% or higher, more preferably has a sequence identity of 80% or higher, more preferably has a sequence identity of 85% or higher, further preferably has a sequence identity of 90% or higher, particularly preferably has a sequence identity of 95% or higher, 96% or higher, 97% or higher, 98% or higher, or 99% or higher, relative to the base sequence of the polynucleotide described in the above (1).

The parthenocarpy regulatory gene of the present invention can exist in a form of RNA (e.g., mRNA) or a form of DNA (e.g., cDNA or genomic DNA). The DNA can be double-stranded or single-stranded. The base sequence represented by SEQ ID NO: 2, which is an example of the polynucleotide of the present invention, is a full-length cDNA of a gene that encodes the polypeptide represented by SEQ ID NO: 1. The parthenocarpy regulatory gene of the present invention can include an additional sequence such as a sequence of an untranslated region (UTR).

A method for obtaining (isolating) the parthenocarpy regulatory gene of the present invention is not limited to a particular one, and can be a method which includes, for example, (i) preparing a probe which is specifically hybridized with a part of the base sequence of the parthenocarpy regulatory gene and (ii) screening a genomic DNA library or a cDNA library.

Alternatively, the method for obtaining the parthenocarpy regulatory gene of the present invention can be a method which uses amplifying means such as PCR. For example, a large amount of DNA fragments each containing the parthenocarpy regulatory gene of the present invention can be obtained by (i) preparing primers from respective 5' end and 3' end sequences (or complementary sequences thereof) in cDNA of the parthenocarpy regulatory gene, (ii) carrying out PCR or the like with the use of the primers and genomic DNA (or cDNA) or the like as a template, and (iii) amplifying a DNA region between the primers.

An origin of the parthenocarpy regulatory gene of the present invention is not limited to a particular one, provided that the origin is a plant. The origin can be a solanaceous plant, a rosaceous plant, a cucurbitaceous plant, or the like, and the solanaceous plant is preferable. Among these, the origin is preferably a *Solanum* plant such as eggplant or tomato, or a *Capsicum* plant such as pepper, more preferably any of eggplant, tomato, and pepper, further preferably eggplant or tomato, particularly preferably eggplant.

Note that whether or not a candidate gene of the isolated parthenocarpy regulatory gene has an intended parthenocarpy regulatory activity can be evaluated by observing whether or not parthenocarpy of the original plant is induced by inhibiting expression of the candidate gene in the original plant.

The parthenocarpy regulatory gene of the present invention can be used to elucidate a mechanism of parthenocarpy of a plant.

Examples of the parthenocarpy regulatory gene of the present invention encompass a gene derived from *S. melongena* which is eggplant (SEQ ID NO: 2, SEQ ID NO: 3 (including ORF), SEQ ID NO: 4 (from a transcription start site to a transcription end site), and SEQ ID NO: 24 (a sequence from 2000 bases upstream of a transcription start site to 1000 bases downstream of a transcription end site)), a gene derived from *S. lycopersicum* which is tomato (SEQ ID NO: 29), a gene derived from *S. pimpinellifolium* which is an allied species of tomato (SEQ ID NO: 31), a gene derived from *S. tuberosum phureja* which is potato (diploid species) (SEQ ID NO: 33), a gene derived from *Capsicum annuum* which is pepper (SEQ ID NO: 35), a gene derived from *Malus domestica* which is apple (SEQ ID NO: 37), and the like. Moreover, the parthenocarpy regulatory gene of the present invention encompasses a gene including nucleotides which have a parthenocarpy regulatory activity and have a sequence identity of 75% or higher, 80% or higher, 85% or higher, 90% or higher, 95% or higher, 96% or higher, 97% or higher, 98% or higher, or 99% or higher, relative to a base sequence of the above exemplified polynucleotide.

The parthenocarpy regulatory gene of the present invention is not limited to a particular expression site and a particular developing stage at which expression occurs. For example, the parthenocarpy regulatory gene of the present invention is expressed in a bud before anthesis or in an ovary at anthesis.

[2. Polypeptide as Parthenocarpy Regulatory Protein]

The polypeptide of the present invention is a product obtained by translating the parthenocarpy regulatory gene described in the part [1. Parthenocarpy regulatory gene] above and has at least an activity to regulate parthenocarpy of a plant. As above described, the polypeptide of the present invention inhibits appearance of the trait of parthenocarpy, i.e., negatively regulates parthenocarpy.

The polypeptide of the present invention can be isolated from a natural resource or can be chemically synthesized. Specifically, the polypeptide encompasses a product obtained by purifying a substance isolated from a natural resource, a product obtained in chemical synthesis process, and a translated product obtained from a procaryotic host or a eucaryotic host (e.g., bacterial cell, yeast cell, higher plant cell, insect cell, or mammalian cell) by a recombination technique.

Specifically, the polypeptide of the present invention is a polypeptide described in any of (1) through (4) below. Note that the polypeptide is a translated product of the parthenocarpy regulatory gene. Therefore, a meaning of the wordings such as "hybridize under a stringent condition" can be understood with reference to the descriptions in [1. Parthenocarpy regulatory gene] above.

(1) A polypeptide having an amino acid sequence represented by SEQ ID NO: 1.

(2) A polypeptide (i) having a sequence identity of 75% or higher relative to the amino acid sequence represented by SEQ ID NO: 1 and (ii) having a parthenocarpy regulatory activity. Note that the sequence identity is preferably 80% or higher, more preferably 85% or higher, more preferably 90% or higher, further preferably 95% or higher, particularly preferably 96% or higher, 97% or higher, 98% or higher, or 99% or higher.

(3) A polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity. Note that the number of amino acids which are substituted, deleted, inserted, and/or added is more preferably 1 to 78, more preferably 1 to 43, more preferably 1 to 39, more preferably 1 to 19, further preferably 1 to 15, particularly preferably 1 to 11, 1 to 5, or 6.

(4) A polypeptide that (i) is encoded by a polynucleotide which is hybridized, under a stringent condition, with a polynucleotide that has a sequence complementary to a polynucleotide for encoding the polypeptide described in the above (1) and (ii) has a parthenocarpy regulatory activity.

The polypeptide may be a polypeptide constituted by peptide bonding of amino acids. Note, however, that the polypeptide is not limited to this and can contain a structure other than a polypeptide structure. The structure other than polypeptide can be a sugar chain, an isoprenoid group, and the like, but is not limited to these in particular.

Moreover, an aspect of the polypeptide of the present invention is an amino group transferase. More specifically, for example, the polypeptide of the present invention has a function as enzyme protein for catalyzing a reaction to generate tryptophan by transferring an amino group contained in amino acid to IPyA. As another aspect, for example, the polypeptide of the present invention has a function as an enzyme protein for catalyzing a reaction to generate tryptophan by transferring an amino group contained in methionine to IPyA.

Note that examples of the polypeptide of the present invention as the parthenocarpy regulatory protein encompass a polypeptide derived from *S. melongena* which is eggplant (SEQ ID NO: 1), a polypeptide derived from *S. lycopersicum* which is tomato (SEQ ID NO: 28), a polypeptide derived from *S. pimpinellifolium* which is an allied species of tomato (SEQ ID NO: 30), a polypeptide derived from *S. tuberosum phureja* which is potato (diploid species) (SEQ ID NO: 32), a polypeptide derived from *Capsicum annuum* which is pepper (SEQ ID NO: 34), a polypeptide derived from *Malus domestica* which is apple (SEQ ID NO: 36), and the like.

[3. Recombinant Expression Vector and Transformant]

The present invention also provides (i) a recombinant expression vector in which the parthenocarpy regulatory gene of the present invention is incorporated such that the parthenocarpy regulatory gene can be expressed and (ii) a transformant in which the recombinant expression vector or the parthenocarpy regulatory gene is introduced such that the recombinant expression vector or the parthenocarpy regulatory gene can be expressed.

A type of a vector for constituting the recombinant expression vector is not limited to a particular one, and a vector which can be expressed in a host cell can be selected as appropriate. That is, a promoter sequence is appropriately selected depending on a type of a host cell, and a vector, in which the promoter sequence and the parthenocarpy regulatory gene of the present invention are incorporated in, for example, a plasmid, a phagemid, a cosmid, or the like, can be used as an expression vector.

Examples of the host cell into which an expression vector is introduced encompass a bacterial cell, a yeast cell, a fungal cell other than a yeast cell, a higher eucaryotic cell, and the like. The bacterial cell can be, for example, an *E. coli* cell. Examples of the higher eucaryotic cell encompass a plant cell and an animal cell. Examples of the plant cell encompass a dicotyledon cell and a monocotyledon cell. The dicotyledon cell can be, for example, a suspension cultured cell of a solanaceous plant (e.g., a tobacco BY-2 strain and a tomato Sly-1 strain), and the monocotyledon cell can be, for example, an Oc strain which is a suspension cultured cell of rice. Examples of the animal cell encompass an insect cell, an amphibian cell, a reptile cell, an avian cell, a fish cell, a mammalian cell, and the like.

The vector is preferably an expression vector. In the expression vector, the polynucleotide of the present invention is functionally linked with an element (e.g., promoter) that is necessary for transcription. Moreover, according to need, the polynucleotide of the present invention can be linked with an enhancer, a selection marker, a splicing signal, a poly A addition signal, a 5'-UTR sequence, and/or the like. The promoter is a DNA sequence that shows a transcription activity in a host cell, and can be appropriately selected depending on a type of host.

Examples of a promoter sequence that can work in a host cell encompass a 35S promoter of cauliflower mosaic virus, a nopaline synthetase gene promoter of *Agrobacterium*, a rice ubiquitin gene promoter, and the like.

It is possible to use a sequence of a promoter region in the polynucleotide of the present invention as a recombinant expression promoter of the present invention.

In the expression vector, the polynucleotide of the present invention can be functionally linked with a proper terminator (e.g., a NOS terminator or a 35S terminator of cauliflower mosaic virus), according to need. A type of the proper terminator can be selected as appropriate in accordance with a type of a host cell, provided that the terminator is a sequence that can terminate transcription of a gene that is transcribed by the above described promoter. The enhancer is used to enhance expression efficiency of an intended gene, and can be, for example, an omega sequence of tobacco mosaic virus.

The recombinant expression vector of the present invention can further contain a selection marker. The selection marker can be, for example, a resistance gene for a drug such as ampicillin, kanamycin, tetracycline, chloramphenicol, neomycin, hygromycin, or spectinomycin.

In the recombinant expression vector, the polynucleotide of the present invention can be bound with a suitable tag sequence for protein purification or a suitable spacer sequence, according to need.

The transformant encompasses an organism, as well as a cell, a tissue, and an organ in which the recombinant expression vector or the parthenocarpy regulatory gene is introduced such that the recombinant expression vector or the parthenocarpy regulatory gene can be expressed. A species of the transformant is not limited to a particular one and can be, for example, a microorganism such as *E. coli*, a plant, an animal, or the like.

[4. Method for Evaluating Parthenocarpy of Plant]

A method of the present invention for evaluating parthenocarpy includes a step of checking (i) whether or not expression of the parthenocarpy regulatory gene is inhibited in a plant or (ii) whether or not a function of a polypeptide encoded by the parthenocarpy regulatory gene is inhibited in the plant. Here, the "parthenocarpy regulatory gene" indicates the parthenocarpy regulatory gene described in [1. Parthenocarpy regulatory gene] above, and the "polypeptide encoded by the parthenocarpy regulatory gene" indicates the polypeptide described in [2. Polypeptide as parthenocarpy regulatory protein] above. Note that the inhibition of expression of the parthenocarpy regulatory gene encompasses inhibition of gene transcription and inhibition of translation into a protein.

Moreover, the case where "expression of the parthenocarpy regulatory gene is inhibited" encompasses both (i) a case where expression of a functional parthenocarpic gene which exists is inhibited and (ii) a case where a parthenocarpic gene itself which can be expressed does not have a function or only has an incomplete function. Among these, an example case where the parthenocarpic gene does not have a function can be a case where a mutant parthenocarpic gene whose function is deficient is expressed.

Further, the case where "a function of a polypeptide encoded by the parthenocarpy regulatory gene is inhibited" encompasses both (i) a case where an expression level of a polypeptide which has an activity and exists is controlled and (ii) a case where a polypeptide itself which is expressed does not have an activity or only has an incomplete function.

Moreover, in the checking step, it is preferable to select, as a candidate plant whose parthenocarpy is regulated, (i) a plant in which expression of the parthenocarpy regulatory gene is determined to be inhibited or (ii) a plant in which the function of the polypeptide encoded by the parthenocarpy regulatory gene is determined to be inhibited.

A method for carrying out the checking step is not limited to a particular one and can be, for example, a genetic method, a biochemical method, and the like. Among these, examples of the genetic method encompass measurement of an expression level of a parthenocarpy regulatory gene, analysis of a base sequence of a parthenocarpy regulatory gene, analysis with use of a marker sequence, and the like. Examples of the biochemical method encompass analysis of an amino acid sequence of a polypeptide, measurement of an activity of a polypeptide, quantitative determination of a metabolic reaction product to which a polypeptide relates, and the like. The following descriptions 1) through 6) will discuss details of these methods. Note that, among these methods, the method of 1) or 2) is preferable in view of easiness in working.

1) Measurement of Expression Level of Parthenocarpy Regulatory Gene

An expression level of the parthenocarpy regulatory gene in a target plant is measured and, if necessary, compared with a standard expression level, and thus whether or not expression of the parthenocarpy regulatory gene is inhibited is checked. The expression level of the gene can be measured by, for example, (i) measuring an amount of a transcript with a method such as quantitative RT-PCR or Northern hybridization or (ii) measuring an amount of a translated product with a method such as quantitative Western blotting. The standard expression level indicates, for example, an expression level of the parthenocarpy regulatory gene in a conspecific plant that does not show parthenocarpy (e.g., an individual having the parthenocarpy regulatory gene as a homozygote). Note that, in a case where transcription or translation of the parthenocarpy regulatory gene is substantially completely inhibited with the use of a method such as gene disruption or RNAi, the comparison with the standard expression level may be unnecessary.

With regard to the expression level of the parthenocarpy regulatory gene, it is preferable to measure a particular site-specific expression level at a particular developing stage. The particular site can be an ovary or an entire flower bud, and the developing stage can be a stage before anthesis or a stage at anthesis.

2) Analysis of Base Sequence of Parthenocarpy Regulatory Gene

A base sequence of a parthenocarpy regulatory gene (genomic DNA, mRNA, or cDNA) of a target plant is analyzed. Then, in a case where a mutation(s) that influences a function of the polypeptide encoded by the parthenocarpy regulatory gene is found as a result of the analysis, it is determined that the function of the polypeptide is inhibited. The mutation(s) that influences the function of the polypeptide can be, for example, deletion of several tens to several thousands of base pairs of nucleotides including a coding region of the parthenocarpy regulatory gene, preferably deletion of at least 4000 bp to 5000 bp nucleotides.

Another example of the mutation(s) that influences the function of the polypeptide can be duplication of several tens to several thousands of base pairs of nucleotides including a coding region of the parthenocarpy regulatory gene, preferably duplication of at least 200 bp to 300 bp of nucleotides.

Another example of the mutation(s) that influences the function of the polypeptide can be a mutation on the parthenocarpy regulatory gene which mutation causes a so-called nonsense mutation or frame-shift mutation. Such a mutation can be caused by 1 bp or more of mutation in the coding region.

Moreover, those mutations occur, for example, in one region or in a plurality of regions. In a case where the mutations occur in the plurality of regions, the above described different types of mutations can occur in respective mutation regions.

Note that such a mutation(s) may occur in at least one of two parthenocarpy regulatory genes (i.e., a pair of parthenocarpy regulatory genes) in a homologous chromosome, and it is preferable that the mutation(s) occurs in both the two parthenocarpy regulatory genes (i.e., recessive homozygote).

3) Analysis Using Marker Sequence

In a case where a marker sequence that shows a linkage with the mutation(s) on the parthenocarpy regulatory gene is utilized, the base sequence of the parthenocarpy regulatory gene can be directly or indirectly checked. The marker sequence is, for example, located within approximately 20 cM (i.e., approximately 20 cM to 0 cM), preferably located within approximately 10 cM, more preferably located within approximately 1 cM, further preferably located within approximately 0.1 cM, from a location of the parthenocarpy regulatory gene. Note that it is of course possible to use the mutation(s) on the parthenocarpy regulatory gene as a marker sequence.

4) Analysis of Amino Acid Sequence of Polypeptide

A polypeptide encoded by the parthenocarpy regulatory gene is isolated from a target plant, and an amino acid sequence of the polypeptide is analyzed. Then, in a case where a mutation(s) (e.g., generation of a truncated body that causes deletion of several tens or more of amino acids), which influences a function of the polypeptide, is found as a result of the analysis, it is determined that the function of the polypeptide is inhibited.

5) Measurement of Activity of Polypeptide

From a target plant, a polypeptide encoded by the parthenocarpy regulatory gene is isolated. Alternatively, a clone of the parthenocarpy regulatory gene in the target plant is introduced into an expression vector and then the expression vector is introduced into a host cell, and thus a polypeptide is transiently expressed. The host cell expressing the polypeptide is cultured, the polypeptide is extracted and purified from the host cell, and the polypeptide is then used to check presence/absence of an amino group transferase activity that catalyzes tryptophan synthesis in which IPyA and amino acid are used as substrates. In a case where the amino group transferase activity does not exist or is lower than a normal plant, it is determined that the function of the polypeptide is inhibited. In an aspect, presence/absence of an amino group transferase activity that catalyzes tryptophan synthesis in which IPyA and methionine are used as substrates is checked, and in a case where the amino group transferase activity does not exist or is lower than a normal plant, it is determined that the function of the polypeptide is inhibited.

As an expression vector for expressing the above peptide, the expression vector described in [3. Recombinant expression vector and transformant] is suitably used.

Moreover, as a host cell, the host cell described in [3. Recombinant expression vector and transformant] is suitably used.

The methods of synthesis, extraction, and purification of a polypeptide are not limited to particular ones, and known methods can be suitably used. Examples of the method for synthesizing the polypeptide encompass (i) a method in which a polypeptide is transiently expressed in a leaf of tobacco or the like via *Agrobacterium* and (ii) a method in which a polypeptide is expressed by transforming an expression vector of a polypeptide into *E. coli* and culturing the *E. coli*.

The method for measuring an amino group transferase activity that catalyzes tryptophan synthesis in which IPyA and amino acid are used as substrates can be, for example, a method in which a reaction solution is prepared by incubating a mixture of (i) the polypeptide obtained by the above described method, (ii) an amino acid mixed solution (Arg, Gln, Cys, Asp, Gly, Met, Phe, and Glu), and (iii) IPyA, and then the reaction solution is purified and subjected to LC/MS/MS analysis. In another aspect, a method is employed in which a reaction solution is prepared by incubating a mixture of the polypeptide obtained by the above described method, methionine (e.g., L-Met), and IPyA, and then the reaction solution is purified and subjected to LC/MS/MS analysis. Moreover, it is preferable to carry out checking of 6) below in addition to the analysis of 4) or 5) in order to check, in the parthenocarpy evaluating method of the present invention, whether or not a function of the polypeptide of the present invention is inhibited.

6) Measurement of Amounts of Endogenous Indole Acetic Acid (IAA) and an Endogenous Indole Pyruvic Acid (IPyA)

From a target plant, a solution is extracted which contains at least one of endogenous indole acetic acid (IAA) and an endogenous indole pyruvic acid (IPyA), and an amount of at least one of these substances is checked. Then, in a case where the amount of the substances is significantly larger than that of a normal plant as a result of the checking, it is determined that a function of the polypeptide is inhibited. Note that the significantly larger amount of substances is not limited to a particular one, and is preferably an amount (concentration) which is twice or more, more preferably three times or more.

Moreover, the amount of at least one of the substances is preferably a site-specific amount checked at a particular developing stage. The particular site can be an ovary or an entire flower bud, and the developing stage can be a stage before anthesis or a stage at anthesis. That is, it is more preferable to measure a concentration of IAA or IPyA that is a precursor of IAA in an ovary or a flower bud before anthesis or at anthesis.

Examples of the method for measuring the amount of the substance encompass measurement with the use of a mass spectrometer, measurement with the use of HPLC, ELISA, and the like. Among these, in view of excellent sensitivity and accuracy, the measuring method with the use of a mass spectrometer is preferable. The mass spectrometer used in the measurement can be LC/MS/MS, GC/MS, or the like.

A type of a plant to which the evaluating method of the present invention is applied is not limited to a particular one, and the plant can be a solanaceous plant, a rosaceous plant, a cucurbitaceous plant, or the like, and the solanaceous plant is preferable. Among these, the plant is preferably a *Solanum* plant such as eggplant or tomato or a *Capsicum* plant such as pepper, more preferably any of eggplant, tomato, and pepper, further preferably eggplant or tomato, particularly preferably eggplant. Moreover, examples of a plant to which the evaluating method is applied encompass a breeding material (parental plant, i.e., pollen parent or seed parent) and offspring obtained by breeding. Note that the term "breeding" indicates a concept that encompasses (i) a method utilizing crossing and (ii) a genetic engineering method.

The phenotypic expression of parthenocarpy sometimes becomes unstable depending on a cultivation condition or a cultivar line and therefore it is often difficult to carry out evaluation based only on appearance of a plant. Moreover, a plant in which the parthenocarpy regulatory gene is heterozygous is worth using as a breeding material or the like but, in particular, when the parthenocarpy regulatory gene is heterozygous, it is sometimes impossible to clearly evaluate only from appearance whether or not the parthenocarpy can be shown. The method of the present invention for evaluating the parthenocarpy is carried out at a gene level, and therefore trait evaluation can be carried out without making genes homozygous. For example, this makes it possible to significantly improve efficiency in breeding selection. Further, the parthenocarpy regulatory gene has been identified, and it is therefore possible to segregate, with the use of a gene engineering technique or the like, linkage with an unfavorable trait which has naturally cosegregated with the parthenocarpy regulatory gene.

[5. Method for Producing Parthenocarpy-Regulated Plant, and Produced Plant]

A form (hereinafter, referred to as "form 1") of a method of the present invention for producing a parthenocarpy-regulated plant is a method that includes a step of selecting a parthenocarpy-regulated plant by carrying out the evaluating method described in [4. Method for evaluating parthenocarpy of plant] above.

Alternatively, another form (hereinafter, referred to as "form 2") of the method of the present invention for producing a parthenocarpy-regulated plant is a method that includes a step of inhibiting expression of the parthenocarpy regulatory gene in the plant or a step of inhibiting a function of a polypeptide encoded by the parthenocarpy regulatory gene in the plant. Here, the "parthenocarpy regulatory gene" is the one described in [1. Parthenocarpy regulatory gene] above, and the "polypeptide encoded by the parthenocarpy regulatory gene" is the one described in [2. Polypeptide as parthenocarpy regulatory protein] above.

Note that, in the form 2, it is preferable to inhibit expression of the parthenocarpy regulatory gene by disrupting the parthenocarpy regulatory gene or introducing, to the plant, a polynucleotide that inhibits expression of the parthenocarpy regulatory gene. Note that the wording "inhibit expression of the parthenocarpy regulatory gene" encompasses (i) inhibition of transcription of a gene and (ii) inhibition of translation into protein. The method for inhibiting expression of the parthenocarpy regulatory gene by disrupting the parthenocarpy regulatory gene or introducing, to the plant, a polynucleotide that inhibits expression of the parthenocarpy regulatory gene can be, for example, a genetic engineering method.

A method for disrupting the parthenocarpy regulatory gene is not limited to a particular one. For example, as the genetic engineering method, it is possible to employ (i) a method in which specific gene disruption is carried out by the use of homologous recombination, (ii) a method in which gene mutation induction is carried out by EMS (ethyl methane sulfonate) treatment, (iii) a method in which a termination codon is introduced to a midway of the parthenocarpy regulatory gene by use of site-directed mutagenesis, or (iv) a method in which a part of a gene is physically disrupted by irradiating the part of the gene with a heavy ion beam or the like.

Moreover, the method for introducing, to the plant, a polynucleotide that inhibits expression of the parthenocarpy regulatory gene is not limited to a particular one and can be, for example, a method such as RNA interference or antisense RNA. A method for introducing, to the plant, an expression cassette (e.g., vector) containing the polynucleotide is not limited to a particular one, and it is possible to employ, as appropriate, a method using polyethyleneglycol, electroporation, a method via *Agrobacterium*, or a method using a particle gun. Note that the expression cassette containing the polynucleotide can be introduced to a plant cell, a callus, a plant tissue, or a plant individual.

Note that expression of the parthenocarpy regulatory gene can be inhibited by introducing a mutation(s), which inhibits gene expression, to an expression adjusting sequence (e.g., a promoter sequence or an enhancer sequence) that regulates expression of the parthenocarpy regulatory gene.

The present invention also provides a parthenocarpy-regulated plant, which has been produced by the above described production method. The term "parthenocarpy-regulated plant" indicates a concept that encompasses (i) a plant in which the trait of parthenocarpy is shown and (ii) a plant in which the trait of parthenocarpy is not shown but which has a predisposition of the parthenocarpy.

A type of a plant which is produced by the method of the present invention is not limited to a particular one, and the plant can be a solanaceous plant, a rosaceous plant, a cucurbitaceous plant, or the like, and the solanaceous plant is preferable. Among these, the plant is preferably a *Solanum* plant such as eggplant or tomato or a *Capsicum* plant such as pepper, more preferably any of eggplant, tomato, and pepper, further preferably eggplant or tomato, particularly preferably eggplant.

An aspect of the plant produced by the method of the present invention encompasses a plant which shows parthenocarpy due to the parthenocarpy regulatory gene of the present invention having gene mutation identical with that of a plant (eggplant) specified by an accession number of FERM BP-22257 described in [6. Parthenocarpy-regulated plant] below or a progeny plant thereof.

Another aspect of the plant produced by the method of the present invention encompasses a plant (i) in which the parthenocarpy regulatory gene of the present invention has gene mutation and (ii) which therefore shows parthenocarpy identical with that of a plant (eggplant) specified by an accession number of FERM BP-22257 described in [6. Parthenocarpy-regulated plant] below or a progeny plant thereof.

[6. Parthenocarpy-Regulated Plant]

The present invention also provides a novel plant that shows parthenocarpy. The plant is a parthenocarpic plant in which (i) expression of a parthenocarpy regulatory gene (i.e., the parthenocarpy regulatory gene of the present invention), which includes a polynucleotide recited in any of (1) through (4) below, is inhibited or (ii) a function of a polypeptide (i.e., the polypeptide of the present invention), which is encoded by the parthenocarpy regulatory gene, is inhibited.

(1) A polynucleotide that encodes a polypeptide having an amino acid sequence represented by SEQ ID NO: 1,
(2) a polynucleotide that encodes a polypeptide (i) having a sequence identity of 75% or higher relative to the amino acid sequence represented by SEQ ID NO: 1 and (ii) having a parthenocarpy regulatory activity,
(3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and
(4) a polynucleotide that (i) is hybridized with a polynucleotide, which has a sequence complementary to the polynucleotide recited in the above (1), under a stringent condition and (ii) encodes a polypeptide having a parthenocarpy regulatory activity.

In a preferable example of the novel parthenocarpic plant of the present invention, as a function of the polypeptide, an activity (amino group transferase activity) for catalyzing a reaction to synthesize tryptophan by transferring an amino group of the amino acids to an indole pyruvic acid (IPyA) is decreased or defective, as compared with a wild type. In another preferable example of the novel parthenocarpic plant of the present invention, as a function of the polypeptide, an activity (amino group transferase activity) for catalyzing a reaction to synthesize tryptophan by transferring an amino group of methionine to an indole pyruvic acid (IPyA) is decreased or detective, as compared with a wild type. That is, a plant is encompassed in which, in the amino acid sequence of the polypeptide, substitution, deletion, insertion, and/or addition of an amino acid occur(s) so as to cause decrease or a defect of the amino group transferase activity. A more specific example of such a plant is a plant (eggplant) specified by the accession number of FERM BP-22257 or a progeny plant thereof (see also Examples). Note that the plant is deposited, in accordance with the Budapest Treaty, at National Institute of Technology and Evaluation (NITE) Patent Microorganisms Depositary (2-5-8 Kazusakamatari, Kisarazu-shi, Chiba, 292-0818) as the accession number of FERM BP-22257 (deposited date: Sep. 11, 2013). A more specific example of the progeny plant can be eggplant that (i) is obtained by single-crossing or double-crossing the eggplant line specified by the accession number of FIRM BP-22257 with another eggplant line or with a plant specified by the accession number of FERM BP-22257 and (ii) shows parthenocarpy due to the parthenocarpy regulatory gene of the present invention having gene mutation identical with that of the plant specified by the accession number of FERM BP-22257.

Another example of the parthenocarpic plant of the present invention can be a plant (i) which has a mutation in a base sequence of the parthenocarpy regulatory gene of the present invention as compared with a wild type, (ii) in which an accumulation amount of mRNA in the parthenocarpy regulatory gene in a non-pollinated ovary at anthesis is controlled, and (iii) which shows parthenocarpy.

Still another example of the parthenocarpic plant of the present invention can be a plant (i) which has a mutation in an amino acid sequence of the polypeptide encoded by the parthenocarpy regulatory gene of the present invention as compared with a wild type, (ii) in which, as a function of the polypeptide, an amino group transferase activity in a non-pollinated ovary at anthesis is decreased or defective, and (iii) which shows parthenocarpy. Moreover, still further specific example of the parthenocarpic plant of the present invention can be a parthenocarpic plant (i) in which the amino group transferase activity as a function of the polypeptide encoded by the parthenocarpy regulatory gene of the present invention in the non-pollinated ovary at anthesis is an activity for catalyzing a reaction to synthesize tryptophan by transferring an amino group of methionine to an indole pyruvic acid (IPyA), (ii) which has a mutation in an amino acid sequence of the polypeptide as compared with a wild type, and (iii) in which the activity for catalyzing a reaction to synthesize tryptophan by transferring an amino group of methionine to an indole pyruvic acid (IPyA) is decreased or defective.

Moreover, yet another example of the parthenocarpic plant of the present invention can be a plant (i) which has a mutation in a base sequence of the parthenocarpy regulatory gene of the present invention as compared with a wild type, (ii) in which an endogenic amount of auxin (or IAA or IPyA) in a non-pollinated ovary at anthesis is increased, and (iii) which shows parthenocarpy.

Another example of the parthenocarpic plant of the present invention encompasses a plant in which the trait of parthenocarpy is shown, among parthenocarpy-regulated plants produced by the production method described in [5. Method for producing parthenocarpy-regulated plant, and produced plant] above. A type of the parthenocarpic plant of the present invention is not limited to a particular one, and the plant can be a solanaceous plant, a rosaceous plant, a cucurbitaceous plant, or the like, and the solanaceous plant is preferable. Among these, the parthenocarpic plant is preferably a *Solanum* plant such as eggplant or tomato or a *Capsicum* plant such as pepper, more preferably any of eggplant, tomato, and pepper, further preferably eggplant or tomato, particularly preferably eggplant. Moreover, the parthenocarpic plant of the present invention encompasses a progeny plant of the novel parthenocarpic plant. Note that the plant is a concept which encompasses a plant body itself, a part of the plant body, a seed, and the like. Further, the parthenocarpic plant of the present invention encompasses a plant that produces, from a flower which has not been pollinated, a fruit having a fruit weight that is equivalent to that of a fruit which is normally produced from a flower that has been normally pollinated under the same cultivation condition.

[7. Examples of Specific Aspects of the Present Invention]

The present invention encompasses any of the following <1> through <19>:

<1> A method for evaluating parthenocarpy of a plant, the method including the step of:
checking whether or not expression of a parthenocarpy regulatory gene, which includes a polynucleotide recited in any of (1) through (4) below, is inhibited in the plant; or
checking whether or not a function of a polypeptide, which is encoded by the parthenocarpy regulatory gene, is inhibited in the plant.
(1) A polynucleotide that encodes a polypeptide having an amino acid sequence represented by SEQ ID NO: 1,
(2) a polynucleotide that encodes a polypeptide (i) having a sequence identity of 75% or higher relative to the amino acid sequence represented by SEQ ID NO: 1 and (ii) having a parthenocarpy regulatory activity,
(3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and
(4) a polynucleotide that (i) is hybridized with a polynucleotide, which has a sequence complementary to the polynucleotide recited in the above (1), under a stringent condition and (ii) encodes a polypeptide having a parthenocarpy regulatory activity.

<2> The method described in <1> in which, in the step of checking, (i) a sequence of the polypeptide having the parthenocarpy regulatory activity, (ii) a base sequence of the parthenocarpy regulatory gene, (iii) an expression level of the parthenocarpy regulatory gene, or (iv) an amount of a transcript of the parthenocarpy regulatory gene is checked.

<3> The method described in <1> or <2> in which, in the step of checking, a plant in which the expression of the parthenocarpy regulatory gene is inhibited or a plant in which the function of the polypeptide encoded by the parthenocarpy regulatory gene is inhibited is selected as a parthenocarpic plant.

<4> A method for producing a parthenocarpy-regulated plant, the method including the step of selecting a parthenocarpic plant by carrying out the evaluating method recited in any one of <1> through <3>.

<5> A method for producing a parthenocarpy-regulated plant, the method including the step of:
inhibiting, in a plant, expression of a parthenocarpy regulatory gene that includes a polynucleotide recited in any of (1) through (4) below; or
inhibiting, in a plant, a function of a polypeptide encoded by the parthenocarpy regulatory gene.
(1) A polynucleotide that encodes a polypeptide having an amino acid sequence represented by SEQ ID NO: 1,
(2) a polynucleotide that encodes a polypeptide (i) having a sequence identity of 75% or higher relative to the amino acid sequence represented by SEQ ID NO: 1 and (ii) having a parthenocarpy regulatory activity,
(3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and
(4) a polynucleotide that (i) is hybridized with a polynucleotide, which has a sequence complementary to the polynucleotide recited in the above (1), under a stringent condition and (ii) encodes a polypeptide having a parthenocarpy regulatory activity.

<6> The method described in <5> in which, in the step, (i) a polynucleotide, which inhibits the expression of the parthenocarpy regulatory gene, is introduced into the plant or (ii) the parthenocarpy regulatory gene is disrupted.

<7> The method described in any one of <1> through <6>, in which the plant is a solanaceous plant.

<8> The method described in <7>, in which the plant is eggplant.

<9> A parthenocarpy-regulated plant produced by the production method described in any one of <5> through <8>.

<10> A parthenocarpy regulatory gene that includes a polynucleotide recited in any of (1) through (4) below.
(1) A polynucleotide that encodes a polypeptide having an amino acid sequence represented by SEQ ID NO: 1,
(2) a polynucleotide that encodes a polypeptide (i) having a sequence identity of 75% or higher relative to the amino acid sequence represented by SEQ ID NO: 1 and (ii) having a parthenocarpy regulatory activity, (3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and (4) a polynucleotide that (i) is hybridized with a polynucleotide, which has a sequence complementary to the polynucleotide recited in the above (1), under a stringent condition and (ii) encodes a polypeptide having a parthenocarpy regulatory activity.

<11> A polypeptide recited in any of (1) through (4) below.

(1) A polypeptide having an amino acid sequence represented by SEQ ID NO: 1, (2) a polypeptide (i) having a sequence identity of 75% or higher relative to the amino acid sequence represented by SEQ ID NO: 1 and (ii) having a parthenocarpy regulatory activity, (3) a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and (4) a polypeptide that (i) is encoded by a polynucleotide which is hybridized, under a stringent condition, with a polynucleotide that has a sequence complementary to a polynucleotide for encoding the polypeptide recited in the above (1) and (ii) has a parthenocarpy regulatory activity.

<12> A plant which is a parthenocarpic plant and in which (i) expression of a parthenocarpy regulatory gene, which includes a polynucleotide recited in any of (1) through (4) below, is inhibited or (ii) a function of a polypeptide, which is encoded by the parthenocarpy regulatory gene, is inhibited.

(1) A polynucleotide that encodes a polypeptide having an amino acid sequence represented by SEQ ID NO: 1, (2) a polynucleotide that encodes a polypeptide (i) having a sequence identity of 75% or higher relative to the amino acid sequence represented by SEQ ID NO: 1 and (ii) having a parthenocarpy regulatory activity, (3) a polynucleotide that encodes a polypeptide (i) having an amino acid sequence in which 1 to 98 amino acids are substituted in, deleted from, inserted into, and/or added to the amino acid sequence represented by SEQ ID NO: 1 and (ii) having a parthenocarpy regulatory activity, and (4) a polynucleotide that (i) is hybridized with a polynucleotide, which has a sequence complementary to the polynucleotide recited in the above (1), under a stringent condition and (ii) encodes a polypeptide having a parthenocarpy regulatory activity.

<13> The plant described in <12>, in which an activity (amino group transferase activity), which is the function of the polypeptide, for catalyzing a reaction to synthesize tryptophan by transferring an amino group of an amino acid to an indole pyruvic acid (IPyA) is decreased or defective.

<14> The plant described in <13>, in which, in the amino acid sequence of the polypeptide, substitution, deletion, insertion, and/or addition of an amino acid occur(s) so as to cause decrease or a defect of the amino group transferase activity.

<15> The plant described in <13> or <14>, in which the reaction to synthesize tryptophan by transferring an amino group of an amino acid to an indole pyruvic acid (IPyA), at least one amino acid whose amino group is to be transferred is methionine.

<16> A plant described in any one of <12> through <15> and a progeny plant thereof, each of the plant and the progeny plant being a solanaceous plant.

<17> The plant and the progeny plant thereof described in <16>, in which the solanaceous plant is eggplant, tomato, or pepper.

<18> The plant described in <17>, in which the plant is a plant specified by an accession number of FERM BP-22257 or is a progeny plant thereof.

<19> The plant described in any one of <12> through <18>, in which the plant is a plant body, a part of the plant body, or a seed of the plant body.

[8. Examples of Other Aspects of the Present Invention]

As other aspects, the present invention encompasses any of the following aspects:

<t1> A method for evaluating parthenocarpy of a plant, the method including the step of:

checking whether or not expression of a parthenocarpy regulatory gene, which includes a polynucleotide recited in any of (t1) through (t4) below, is inhibited in the plant; or checking whether or not a function of a polypeptide, which is encoded by the parthenocarpy regulatory gene, is inhibited in the plant.

(t1) A polynucleotide that encodes a polypeptide having an amino acid sequence represented by SEQ ID NO: 28, (t2) a polynucleotide that encodes a polypeptide (i) having a sequence identity of 75% or higher relative to the amino acid sequence represented by SEQ ID NO: 28 and (ii) having a parthenocarpy regulatory activity, (t3) a polynucleotide that encodes a polypeptide (i) having an amino acid sequence in which 1 to 98 amino acids are substituted in, deleted from, inserted into, and/or added to the amino acid sequence represented by SEQ ID NO: 28 and (ii) having a parthenocarpy regulatory activity, and (t4) a polynucleotide that (i) is hybridized with a polynucleotide, which has a sequence complementary to the polynucleotide recited in the above (t1), under a stringent condition and (ii) encodes a polypeptide having a parthenocarpy regulatory activity.

<t2> The method described in <t1> in which, in the step of checking, (i) a sequence of the polypeptide having the parthenocarpy regulatory activity, (ii) a base sequence of the parthenocarpy regulatory gene, (iii) an expression level of the parthenocarpy regulatory gene, or (iv) an amount of a transcript of the parthenocarpy regulatory gene is checked.

<t3> The method described in <t1> or <t2> in which, in the step of checking, a plant in which the expression of the parthenocarpy regulatory gene is inhibited or a plant in which the function of the polypeptide encoded by the parthenocarpy regulatory gene is inhibited is selected as a parthenocarpic plant.

<t4> A method for producing a parthenocarpy-regulated plant, the method including the step of selecting a parthenocarpic plant by carrying out the evaluating method recited in any one of <t1> through <t3>.

<t5> A method for producing a parthenocarpy-regulated plant, the method including the step of:

inhibiting, in a plant, expression of a parthenocarpy regulatory gene that includes a polynucleotide recited in any of (t1) through (t4) below; or inhibiting, in a plant, a function of a polypeptide encoded by the parthenocarpy regulatory gene.

(t1) A polynucleotide that encodes a polypeptide having an amino acid sequence represented by SEQ ID NO: 28, (t2) a polynucleotide that encodes a polypeptide (i) having a sequence identity of 75% or higher relative to the amino acid sequence represented by SEQ ID NO: 28 and (ii) having a parthenocarpy regulatory activity,
(t3) a polynucleotide that encodes a polypeptide (i) having an amino acid sequence in which 1 to 98 amino acids are substituted in, deleted from, inserted into, and/or added to the amino acid sequence represented by SEQ ID NO: 28 and (ii) having a parthenocarpy regulatory activity, and
(t4) a polynucleotide that (i) is hybridized with a polynucleotide, which has a sequence complementary to the polynucleotide recited in the above (t1), under a stringent condition and (ii) encodes a polypeptide having a parthenocarpy regulatory activity.

<t6> The method described in <t7> in which, in the step, (i) a polynucleotide, which inhibits the expression of the parthenocarpy regulatory gene, is introduced into the plant or (ii) the parthenocarpy regulatory gene is disrupted.

<t7> The method described in any one of <t1> through <t8>, in which the plant is a solanaceous plant.

<t8> The method described in <t9>, in which the plant is eggplant.

<t9> A parthenocarpy-regulated plant produced by the production method described in any one of <t5> through <t8>.

<t10> A parthenocarpy regulatory gene that includes a polynucleotide recited in any of (t1) through (t4) below.
(t1) A polynucleotide that encodes a polypeptide having an amino acid sequence represented by SEQ ID NO: 28,
(t2) a polynucleotide that encodes a polypeptide (i) having a sequence identity of 75% or higher relative to the amino acid sequence represented by SEQ ID NO: 28 and (ii) having a parthenocarpy regulatory activity,
(t3) a polynucleotide that encodes a polypeptide (i) having an amino acid sequence in which 1 to 98 amino acids are substituted in, deleted from, inserted into, and/or added to the amino acid sequence represented by SEQ ID NO: 28 and (ii) having a parthenocarpy regulatory activity, and
(t4) a polynucleotide that (i) is hybridized with a polynucleotide, which has a sequence complementary to the polynucleotide recited in the above (t1), under a stringent condition and (ii) encodes a polypeptide having a parthenocarpy regulatory activity.

<t11> A polypeptide recited in any of (t1) through (t4) below.
(t1) A polypeptide having an amino acid sequence represented by SEQ ID NO: 28,
(t2) a polypeptide (i) having a sequence identity of 75% or higher relative to the amino acid sequence represented by SEQ ID NO: 28 and (ii) having a parthenocarpy regulatory activity,
(t3) a polypeptide (i) having an amino acid sequence in which 1 to 98 amino acids are substituted in, deleted from, inserted into, and/or added to the amino acid sequence represented by SEQ ID NO: 28 and (ii) having a parthenocarpy regulatory activity, and
(t4) a polypeptide that (i) is encoded by a polynucleotide which is hybridized, under a stringent condition, with a polynucleotide that has a sequence complementary to a polynucleotide for encoding the polypeptide recited in the above (t1) and (ii) has a parthenocarpy regulatory activity.

<t12> A plant which is a parthenocarpic plant and in which (i) expression of a parthenocarpy regulatory gene, which includes a polynucleotide recited in any of (t1) through (t4) below, is inhibited or (ii) a function of a polypeptide, which is encoded by the parthenocarpy regulatory gene, is inhibited.

(t1) A polynucleotide that encodes a polypeptide having an amino acid sequence represented by SEQ ID NO: 28,
(t2) a polynucleotide that encodes a polypeptide (i) having a sequence identity of 75% or higher relative to the amino acid sequence represented by SEQ ID NO: 28 and (ii) having a parthenocarpy regulatory activity,
(t3) a polynucleotide that encodes a polypeptide (i) having an amino acid sequence in which 1 to 98 amino acids are substituted in, deleted from, inserted into, and/or added to the amino acid sequence represented by SEQ ID NO: 28 and (ii) having a parthenocarpy regulatory activity, and
(t4) a polynucleotide that (i) is hybridized with a polynucleotide, which has a sequence complementary to the polynucleotide recited in the above (t1), under a stringent condition and (ii) encodes a polypeptide having a parthenocarpy regulatory activity.

<t13> The plant described in <t12>, in which an activity (amino group transferase activity), which is the function of the polypeptide, for catalyzing a reaction to synthesize tryptophan by transferring an amino group of an amino acid to an indole pyruvic acid (IPyA) is decreased or defective.

<t14> The plant described in <t13>, in which, in the amino acid sequence of the polypeptide, substitution, deletion, insertion, and/or addition of an amino acid occur(s) so as to cause decrease or a defect of the amino group transferase activity.

<t15> The plant described in <t13> or <t14>, in which, in the reaction to synthesize tryptophan by transferring an amino group of an amino acid to an indole pyruvic acid (IPyA), at least one amino acid whose amino group is to be transferred is methionine.

<t16> A plant described in any one of <t12> through <t15> and a progeny plant thereof, each of the plant and the progeny plant being a solanaceous plant.

<t17> The plant and the progeny plant thereof described in <t16>, in which the solanaceous plant is eggplant, tomato, or pepper.

<t18> The plant described in <t17>, in which the plant is a plant specified by an accession number of FERM BP-22257 or is a progeny plant thereof.

<t19> The plant described in any one of <t12> through <t18>, in which the plant is a plant body, a part of the plant body, or a seed of the plant body.

As still other aspects, the present invention encompasses any of the following aspects:

<p1> A method for evaluating parthenocarpy of a plant, the method including the step of:
checking whether or not expression of a parthenocarpy regulatory gene, which includes a polynucleotide recited in any of (p1) through (p4) below, is inhibited in the plant; or
checking whether or not a function of a polypeptide, which is encoded by the parthenocarpy regulatory gene, is inhibited in the plant.

(p1) A polynucleotide that encodes a polypeptide having an amino acid sequence represented by SEQ ID NO: 34,
(p2) a polynucleotide that encodes a polypeptide (i) having a sequence identity of 75% or higher relative to the amino acid sequence represented by SEQ ID NO: 34 and (ii) having a parthenocarpy regulatory activity,
(p3) a polynucleotide that encodes a polypeptide (i) having an amino acid sequence in which 1 to 98 amino acids are substituted in, deleted from, inserted into, and/or added to the amino acid sequence represented by SEQ ID NO: 34 and (ii) having a parthenocarpy regulatory activity, and
(p4) a polynucleotide that (i) is hybridized with a polynucleotide, which has a sequence complementary to the polynucleotide recited in the above (p1), under a stringent condition and (ii) encodes a polypeptide having a parthenocarpy regulatory activity.

<p2> The method described in <p1> in which, in the step of checking, (i) a sequence of the polypeptide having the parthenocarpy regulatory activity, (ii) a base sequence of the parthenocarpy regulatory gene, (iii) an expression level of the parthenocarpy regulatory gene, or (iv) an amount of a transcript of the parthenocarpy regulatory gene is checked.

<p3> The method described in <p1> or <p2> in which, in the step of checking, a plant in which the expression of the parthenocarpy regulatory gene is inhibited or a plant in which the function of the polypeptide encoded by the parthenocarpy regulatory gene is inhibited is selected as a parthenocarpic plant.

<p4> A method for producing a parthenocarpy-regulated plant, the method including the step of selecting a parthenocarpic plant by carrying out the evaluating method recited in any one of <p1> through <p3>.

<p5> A method for producing a parthenocarpy-regulated plant, the method including the step of:
inhibiting, in a plant, expression of a parthenocarpy regulatory gene that includes a polynucleotide recited in any of (p1) through (p4) below; or
inhibiting, in a plant, a function of a polypeptide encoded by the parthenocarpy regulatory gene.

(p1) A polynucleotide that encodes a polypeptide having an amino acid sequence represented by SEQ ID NO: 34, (p2) a polynucleotide that encodes a polypeptide (i) having a sequence identity of 75% or higher relative to the amino acid sequence represented by SEQ ID NO: 34 and (ii) having a parthenocarpy regulatory activity, (p3) a polynucleotide that encodes a polypeptide (i) having an amino acid sequence in which 1 to 98 amino acids are substituted in, deleted from, inserted into, and/or added to the amino acid sequence represented by SEQ ID NO: 34 and (ii) having a parthenocarpy regulatory activity, and (p4) a polynucleotide that (i) is hybridized with a polynucleotide, which has a sequence complementary to the polynucleotide recited in the above (p1), under a stringent condition and (ii) encodes a polypeptide having a parthenocarpy regulatory activity.

<p6> The method described in <p7> in which, in the step, (i) a polynucleotide, which inhibits the expression of the parthenocarpy regulatory gene, is introduced into the plant or (ii) the parthenocarpy regulatory gene is disrupted.

<p7> The method described in any one of <p1> through <p8>, in which the plant is a solanaceous plant.

<p8> The method described in <p9>, in which the plant is eggplant.

<p9> A parthenocarpy-regulated plant produced by the production method described in any one of <p5> through <p8>.

<p10> A parthenocarpy regulatory gene that includes a polynucleotide recited in any of (p1) through (p4) below.

(p1) A polynucleotide that encodes a polypeptide having an amino acid sequence represented by SEQ ID NO: 34, (p2) a polynucleotide that encodes a polypeptide (i) having a sequence identity of 75% or higher relative to the amino acid sequence represented by SEQ ID NO: 34 and (ii) having a parthenocarpy regulatory activity, (p3) a polynucleotide that encodes a polypeptide (i) having an amino acid sequence in which 1 to 98 amino acids are substituted in, deleted from, inserted into, and/or added to the amino acid sequence represented by SEQ ID NO: 34 and (ii) having a parthenocarpy regulatory activity, and (p4) a polynucleotide that (i) is hybridized with a polynucleotide, which has a sequence complementary to the polynucleotide recited in the above (p1), under a stringent condition and (ii) encodes a polypeptide having a parthenocarpy regulatory activity.

<p11> A polypeptide recited in any of (p1) through (p4) below.

(p1) A polypeptide having an amino acid sequence represented by SEQ ID NO: 34, (p2) a polypeptide (i) having a sequence identity of 75% or higher relative to the amino acid sequence represented by SEQ ID NO: 34 and (ii) having a parthenocarpy regulatory activity, (p3) a polypeptide (i) having an amino acid sequence in which 1 to 98 amino acids are substituted in, deleted from, inserted into, and/or added to the amino acid sequence represented by SEQ ID NO: 34 and (ii) having a parthenocarpy regulatory activity, and (p4) a polypeptide that (i) is encoded by a polynucleotide which is hybridized, under a stringent condition, with a polynucleotide that has a sequence complementary to a polynucleotide for encoding the polypeptide recited in the above (p1) and (ii) has a parthenocarpy regulatory activity.

<p12> A plant which is a parthenocarpic plant and in which (i) expression of a parthenocarpy regulatory gene, which includes a polynucleotide recited in any of (p1) through (p4) below, is inhibited or (ii) a function of a polypeptide, which is encoded by the parthenocarpy regulatory gene, is inhibited.

(p1) A polynucleotide that encodes a polypeptide having an amino acid sequence represented by SEQ ID NO: 34, (p2) a polynucleotide that encodes a polypeptide (i) having a sequence identity of 75% or higher relative to the amino acid sequence represented by SEQ ID NO: 34 and (ii) having a parthenocarpy regulatory activity, (p3) a polynucleotide that encodes a polypeptide (i) having an amino acid sequence in which 1 to 98 amino acids are substituted in, deleted from, inserted into, and/or added to the amino acid sequence represented by SEQ ID NO: 34 and (ii) having a parthenocarpy regulatory activity, and (p4) a polynucleotide that (i) is hybridized with a polynucleotide, which has a sequence complementary to the polynucleotide recited in the above (p1), under a stringent condition and (ii) encodes a polypeptide having a parthenocarpy regulatory activity.

<p13> The plant described in <12>, in which an activity (amino group transferase activity), which is the function of the polypeptide, for catalyzing a reaction to synthesize tryptophan by transferring an amino group of an amino acid to an indole pyruvic acid (IPyA) is decreased or defective.

<p14> The plant described in <p13>, in which, in the amino acid sequence of the polypeptide, substitution, deletion, insertion, and/or addition of an amino acid occur(s) so as to cause decrease or a defect of the amino group transferase activity.

<p15> The plant described in <p13> or <p14>, in which, in the reaction to synthesize tryptophan by transferring an amino group of an amino acid to an indole pyruvic acid (IPyA), at least one amino acid whose amino group is to be transferred is methionine.

<p16> A plant described in any one of <p12> through <p15> and a progeny plant thereof, each of the plant and the progeny plant being a solanaceous plant.

<p17> The plant and the progeny plant thereof described in <p16>, in which the solanaceous plant is eggplant, tomato, or pepper.

<p18> The plant described in <p17>, in which the plant is a plant specified by an accession number of FERM BP-22257 or is a progeny plant thereof.

<p19> The plant described in any one of <p12> through <p18>, in which the plant is a plant body, a part of the plant body, or a seed of the plant body.

The present invention is not limited to the embodiments, but can be variously altered by a skilled person in the art within the scope of the claims. That is, an embodiment derived from a proper combination of technical means appropriately modified within the scope of the claims is also encompassed in the technical scope of the present invention. Further, it is possible to form a new technical feature by combining the technical means disclosed in the respective embodiments.

EXAMPLES

Example 1

Eggplant-Derived Parthenocarpy Gene A (1. Identification and Analysis of Eggplant-Derived Parthenocarpy Responsible Gene A)

<Discovery of Parthenocarpic Eggplant Line "PCSS">

The following description will be given with reference to FIG. 1. FIG. 1 is a view illustrating parthenocarpy of a parthenocarpic eggplant line "PCSS" in accordance with Example 1 of the present invention. (a) of FIG. 1 illustrates a fruit of eggplant, in a parthenocarpic eggplant line "PCSS," whose stigma was cut off in a bud stage before anthesis so that pollination was prevented. (b) of FIG. 1 illustrates (i) a fruit (left) of eggplant in the parthenocarpic eggplant line "PCSS" and (ii) a fruit (right) of eggplant "Senryo-nigo," which is of a common non-parthenocarpic cultivar. Each stigma of the eggplant in the parthenocarpic eggplant line "PCSS" and the eggplant "Senryo-nigo" was cut off in a bud stage before anthesis so that pollination was prevented.

The line PCSS is a selfed fixed line of parthenocarpic eggplant (*Solanum melongena*). This line was found in the process of breed improvement carried out with the use of crossbreed progeny between breeding mother plant lines "line 1" and "line 2" of eggplant which was bred uniquely by the inventors.

In a case where the stigma was cut off in the bud stage before the anthesis so that the pollination was prevented, the fruit of the eggplant "Senryo-nigo," which is of a common non-parthenocarpic cultivar, was hardly enlarged (see (b) of FIG. 1), whereas the fruit of the eggplant in the line PCSS was normally enlarged ((a) and (b) of FIG. 1).

A subsequent analysis clarified the following: (1) neither of the "line 1" nor the "line 2," each of which was used as a parent line for breeding, had parthenocarpy; (2) out of a great number of selfed sib lines obtained from crossbreed progeny between those two lines, no line had parthenocarpy, except for the line PCSS; (3) among selfed progeny of the line PCSS, all individuals had parthenocarpy; and (4) among crossbreed progeny between the line PCSS and a non-parthenocarpic line, individuals having parthenocarpy similar to that of the line PCSS appeared at a given frequency.

In view of the above results, it was concluded that the parthenocarpy of the line PCSS was attributed to a novel genetic mutation caused by a natural mutation in the process of cross breeding. As such, the line PCSS was registered with the accession number "FERM BP-22257" as a parthenocarpic eggplant line.

<Detailed Mapping of Parthenocarpy>

The first filial generation obtained by crossbreeding the parthenocarpic eggplant line PCSS with a non-parthenocarpic eggplant line TN-43 (bred by TAKII & CO., LTD.) was selfed so as to obtain the second filial generation (F2). 93 individuals in this F2 generation were cultivated, and evaluated in terms of parthenocarpy. As a result, out of the 93 individuals, 23 individuals had parthenocarpy, whereas 70 individuals had non-parthenocarpy. As such, a segregation ratio was approximately 1:3. This suggested that the parthenocarpy of the line PCSS was under the control of a single recessive gene. Genomic DNA was extracted from those F2 individuals, and marker genotypes of the genomic DNA were determined with the use of 64 DNA markers distributed over an entire eggplant genome (Reference Literature: Fukuoka et al. (2012) Theor. Appl. Genet. 125: 47-56). A chromosomal location, on a marker linkage map, of a gene responsible for the parthenocarpy was calculated with the use of Mapmaker/EXP (Reference Literature: Lander et al., 1987, Genomics 1: 174-181) in accordance with information on the marker genotypes, and the chromosomal location of the gene was deduced. FIG. 2 illustrates a linkage map of a region in which a parthenocarpy responsible gene A was deduced to be located. As illustrated in FIG. 2, it was deduced that the gene was located in a region of approximately 20 cM, sandwiched between two DNA markers SOL7214 and eme07D02, of the third chromosome.

Further, by direct comparison between the marker genotypes and phenotypes, determination of the region in which the gene was located was attempted. A result of the determination is illustrated in FIG. 3. FIG. 3 is a view illustrating correspondence between phenotypes and marker genotypes of each generation after crossbreeding of the parthenocarpic eggplant line PCSS with the non-parthenocarpic eggplant line TN-43. (a) of FIG. 3 is a view illustrating correspondence between phenotypes and marker genotypes of a F2 generation.

As illustrated in (a) of FIG. 3, an individual 24 and an individual 44 did not have parthenocarpy and an individual 30 and an individual 45 had parthenocarpy. This revealed that the gene was located in a region sandwiched between est_smfl28j21 and eme07D02. Note here that it is reported that, in a vicinity of this region which is present in the third linkage group of eggplant, order of arrangement of genes is highly-conserved, as compared with a tomato chromosome (synteny) (Reference Literatures: Wu et al. (2009) Theor. Appl. Genet. 118: 927-935, Fukuoka et al. (2012) Theor. Appl. Genet. 125: 47-56). In view of this, new DNA markers were developed with the use of a tomato genomic sequence so as to narrow down the chromosomal location of the gene. Out of two DNA markers which defined respective ends of the region in which the gene was deduced to be located, est_smfl28j21 was developed based on an eggplant expressed sequence SmFL28J21 (Reference Literature: Fukuoka et al. (2010) Gene 450: 76-84), and was found, by BLASTN search with respect to a tomato complete genomic sequence (SL2.40ch, Reference Literature: The Tomato Genome Consortium (2012) Nature 485: 635-641), to have an extremely high sequence identity with a predicted gene Solyc03g118430.2.1 that was present in a region from nucleotide number 61358472 to nucleotide number 61373773 of a tomato third chromosome. On the other hand, eme07D02 is a genomic SSR marker that uses repeat sequences scattered on an eggplant genome. Since it had been difficult to correctly predict correspondence between eme07D02 and the tomato genomic sequence, development of a marker was advanced in accordance with a sequence of SOL8369 located outside eme07D02 (i.e., opposite to est_smfl28j21). The eggplant expressed sequence SmFL14B23, derived from SOL8369, had an extremely high sequence identity with a predicted gene Solyc03g123840.2.1 predicted in a region from nucleotide number 64597421 to nucleotide number 64602015 of the tomato third chromosome. That is, it was deduced that the region in which the gene responsible for the parthenocarpy of the line PCSS was located corresponded, according to the tomato genome, to a region of approximately 3.24 Mb from nucleotide number 61358472 to nucleotide number 64602015 of the third chromosome in the tomato genome. Furthermore, with the use of uniquely deciphered eggplant EST sequences (43,250 sequences in total) as query sequences, BLAST search was carried out with respect to the tomato genomic sequence so as to check a sequence identity. As a result, 427 eggplant ESTs were found which corresponded to the predicted gene present in the region of 3.24 Mb on the tomato genome. In view of this, a PCR primer was designed in accordance with the 427 eggplant EST sequences, then genomic DNA of each of the line PCSS and the line TN-43 were amplified, and polymorphism of the genomic DNA was checked. It was thus possible to arrange nine SNP markers and one SSR marker between est_smfl28j21 and SOL8369. With the use of those markers, phenotypes (i.e., presence/absence of parthenocarpy) and marker genotypes of each individual in a F3 generation and subsequent generations were compared. First, in regard to a region sandwiched between est_smfl28j21 and SOL8369, F2 individuals which had a PCSS-derived region so as to become heterozygous and a TN-43-derived region were selfed, and an individual having recombination between the two regions was selected among progeny of the F2 individuals with the use of DNA markers. The individual was then further selfed so as to breed a recombinant homozygous line. The recombinant homozygous line was studied in terms of the presence/absence of parthenocarpy, and development of new SNP markers were repeated so as to identify a recombinant part. Results are illustrated in (b) of FIG. 3. (b) of FIG. 3 is a view illustrating correspondence between the phenotypes and the marker genotypes of the F3 generation and the subsequent generations. As illustrated in (b) of FIG. 3, a possible genomic region in which the gene responsible for the parthenocarpy was present could be narrowed down over generations, that is, the possible genomic region was narrowed down to a region sandwiched between ec3110A and ec3077F in the F3 generation, to a region sandwiched between SSR03 and ec3087X in a F5 generation which region was located on an inner side of the region sandwiched between ec3110A and ec3077F, and to a region sandwiched between SSR03 and PaSeq128 in a F8 generation which region was located on an inner side of the region sandwiched between SSR03 and ec3087X.

(2. Isolation of Parthenocarpy Responsible Gene A)

<Isolation and Sequence Determination of Full-Length cDNA of Gene A>

By screening of a BAC library of eggplant (line AE-P03, bred by incorporated administrative agency National Agriculture and Food Research Organization) with use of a PCR primer which amplifies PaSeq123, a BAC clone 08K19 including such a region was isolated. A shotgun library of this clone was created, and a base sequence was determined in regard to a full length of insert. As a result, it was revealed that, according to the line AE-P03, a physical distance between SSR03 and PaSeq128 was 31,484 bp. In a case where base sequences of both of the line PCSS and the line TN-43 in the region were determined, it was revealed that the line PCSS had a characteristic structure mutation which was not found in the line TN-43 and the line AE-P03. In a case where a structure of the structure mutation was analyzed in more detail, it was revealed that the line PCSS had deletion of 4558 bp and duplication of 227 bp in a region between SSR03 and PaSeq123.

With respect to the region sandwiched between SSR03 and PaSeq128, a structural gene was predicted by a gene prediction program GenScan (Reference Literature: Burge, C. and Karlin, S. (1997) J. Mol. Biol. 268: 78-94) with use of a wild type (AE-P03) sequence. As a result, presence of four structural genes was suggested. It was deduced that one (gene A) of the four structural genes was present in a part in which the structure mutation, specific to the line PCSS, occurred and that, according to the line PCSS, a gene region including a protein-encoding region was partially deleted due to deletion of the 4558 bp.

In view of this, full-length cDNA of the gene A was cloned by the RACE method so as to confirm that the gene predicted by the gene prediction program was actually present. Cloning was carried out the with use of (i) PCR primers designed in accordance with a base sequence of such a predicted gene and (ii) as a material, total RNA extracted from a bud of non-parthenocarpic eggplant "Nakateshinkuro," which is of standard cultivar.

First, total RNA was extracted, by the Trizol method, from an ovary taken out of a bud of eggplant "Nakateshinkuro" approximately 3 days before anthesis, and cDNA was synthesized with use of the SMARTer RACE cDNA amplification kit (Takara Bio Inc.). With use of (i) the cDNA as a template and (ii) polynucleotides represented by SEQ ID NO: 39 and SEQ ID NO: 40 as gene-specific primers, amplification of cDNA including a transcription start site and a translation start site of mRNA was attempted by the Nested-5'-RACE method. Resultant amplified products were cloned into an *E. coli* expression vector, and sequences of amplified products in clones were determined by the Sanger's method. For the purpose of eliminating an effect of a sequence mutation that is caused at a low frequency by PCR, such base sequences of the clones were independently determined. As a result, a sequence of 394 bp at a 5'-end of full-length cDNA was obtained. Similarly, amplification of cDNA including a translation end site and a polyadenylation site was attempted by a Nested-3'-RACE method with use of polynucleotides represented by SEQ ID NO: 41 and SEQ ID NO: 42 as gene-specific primers. Then, (i) cloning of the amplified product into an *E. coli* vector and (ii) determination of sequences were attempted. As a result, a sequence of 1247 bp at a 3' end of full-length cDNA was obtained. Thereafter, a sequence of 1625 bp which sequence was represented by SEQ ID NO: 2 was obtained by combining the sequence at the 5'-end with the sequence at the 3' end in accordance with overlap of those two sequences. The sequence thus obtained was determined as a full-length cDNA sequence of the parthenocarpy responsible gene A.

<Analysis of Expression Level of Gene A at each Site of Plant Body in Each Developing Stage>

Based on this result, DNA fragments each including the whole of protein codes of the gene A was cloned by PCR with use of the polynucleotides represented by SEQ ID NO: 43 and 44 as primers. As a template of the PCR, cDNA was used which was synthesized from total RNA of eggplant "Nakateshinkuro" with use of the Transcriptor First Strand cDNA Synthesis kit (Roche Diagnostics K.K.). Amplified fragments thus obtained were digested by enzymes XmaI and SacI, and inserted into an XmaI-SacI site of a cloning vector pUC19 (Takara Bio Inc.). In regard to clones thus obtained, base sequences of such inserted fragments were determined, and a clone was selected which did not have a mutation as compared with a full-length cDNA sequence represented by SEQ ID NO: 2. A sequence of the clone is represented by SEQ ID NO: 3.

Figure 4:
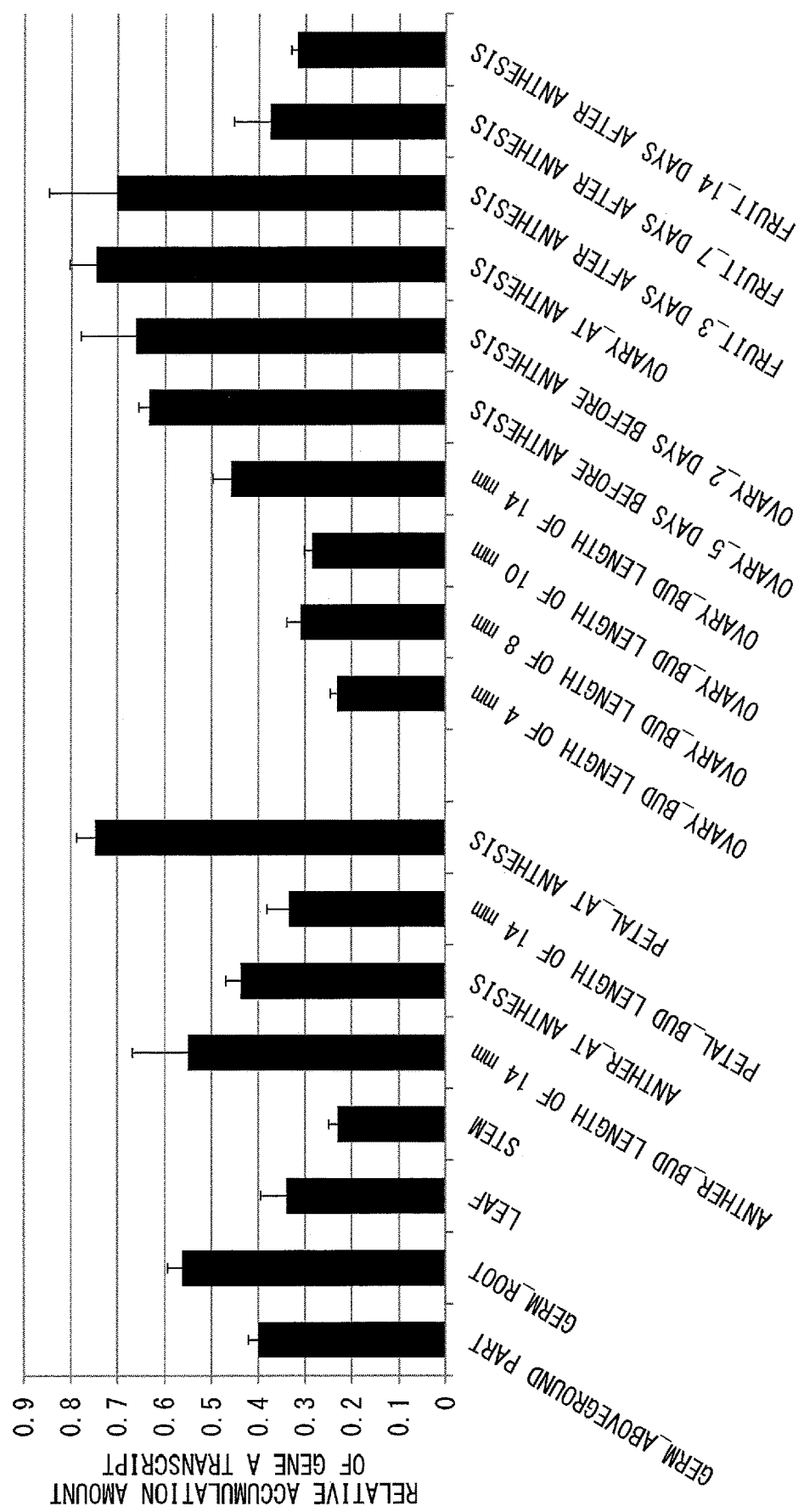
FIG. 4 is a view illustrating mRNA accumulation amounts in genes A of sites of "Nakateshinkuro" at different developing stages, in Example 1 of the present invention.

Further, RNA was extracted from ovaries, taken out of buds before anthesis (buds at respective 6 stages, i.e., buds having respective lengths of 4 mm, 8 mm, 10 mm, and 14 mm and buds being 5 days and 2 days before anthesis) and of flowers at anthesis, and developing unripe fruits (at 3 stages of 3 days, 7 days, and 14 days after anthesis) of eggplant "Nakateshinkuro." With use of such RNA as a template, cDNA was synthesized with use of the Superscript VILO cDNA synthesis kit (Life Technologies Corporation). With use of this cDNA as a template, an mRNA accumulation amount of the gene A was measured by quantitative PCR with use of oligonucleotides represented by SEQ ID NO: 45 and SEQ ID NO: 46 as primers. Eggplant constitutive expression gene 20F01A, which was found uniquely by the inventors, was used as an internal standard gene for standardizing a quantitative value. An experiment was carried out with the use of primer pairs represented by SEQ ID NO: 47 and SEQ ID NO: 48 as primers for amplifying the internal standard gene. Furthermore, mRNA accumulation amounts were similarly measured in regard to an aboveground part and a root of a germ (28 days after seeding), a matured leaf and a stem of a plant body 3 months after the seeding, and anthers and petals of a bud (having a bud length of 14 mm) before anthesis and a flower at anthesis of eggplant cultivar "Nakateshinkuro." Results of such quantitative determination are illustrated in FIG. 4. FIG. 4 illustrates mRNA accumulation amounts of the gene A of sites of "Nakateshinkuro" at different developing stages. As is clear from FIG. 4, it was clarified that expression of the gene A was increased in the ovaries as the buds developed, then was at the highest level at anthesis, and was decreased as the fruits developed. As a result, it was confirmed that the gene A was a gene which was expressed in expression patterns specific to development stages of a flower of general non-parthenocarpic eggplant.

<Detailed Analysis of Structure of Gene A and Mutation of Line PCSS>

It was clarified by comparison between full-length cDNA and a genomic DNA sequence that the gene A was made up of nine exons and eight introns and had 6528 bp between a transcription start site and a transcription end site. This sequence is represented by SEQ ID NO: 4. Further, sequences from the first to ninth exons of the gene A are represented by SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, and SEQ ID NO: 21, respectively. Moreover, sequences from the first to eighth introns are represented by SEQ ID NO: 6, SEQ ID NO: 8, SEQ ID NO: 10, SEQ ID NO: 12, SEQ ID NO: 14, SEQ ID NO: 16, SEQ ID NO: 18, and SEQ ID NO: 20, respectively. In addition, 2000 bases upstream of the transcription start site and 1000 bases downstream of the transcription end site are represented by SEQ ID NO: 22 and SEQ ID NO: 23, respectively. Those sequences are integrated, and resultant sequence of 9528 bases from the 2000 bases upstream of the transcription start site of the gene A to the 1000 bases downstream of the transcription end site of the gene A are represented by SEQ ID NO: 24 as a gene A region. The number of the first base of the sequence is "1" and the number of the last base of the sequence is "9528."

In a case where correspondence between (i) the gene A and (ii) a deletion region and a duplication region of the line PCSS was checked, a region (a sequence represented by SEQ ID NO: 25) corresponding to bases from nucleotide number 3963 of SEQ ID NO: 24 to nucleotide number 8520 of SEQ ID NO: 24 was deleted in such a mutant type gene A region of the line PCSS. This region is a region of 4,558 base pairs including (i) all bases from the 45th base in the fourth intron to the translation end site in the ninth exon and (ii) a subsequent untranslated region of 235 bases on a 3' end side. Moreover, it was clarified that a sequence (SEQ ID NO: 26) of 227 base pairs corresponding to bases from nucleotide number 8599 of SEQ ID NO: 24 to nucleotide number 8825 of SEQ ID NO: 24 was duplicated and inserted instead of the region of 4,558 base pairs which region was deleted.

Moreover, a region of a wild type gene which region ranged from a start site of the fourth exon to 1000 base pairs downstream of a transcription end site, that is, a sequence of 5670 bases from nucleotide number 3859 to nucleotide number 9528 of SEQ ID NO: 24 became, in the line PCSS, a sequence having a structure represented by SEQ ID NO: 27 and having a length of 1339 bases. Based on results of the foregoing analysis, a schematic diagram illustrating a structure of the gene A and a mutation structure of the gene A of the PSCC was created as illustrated in FIG. 5.

Figure 5:
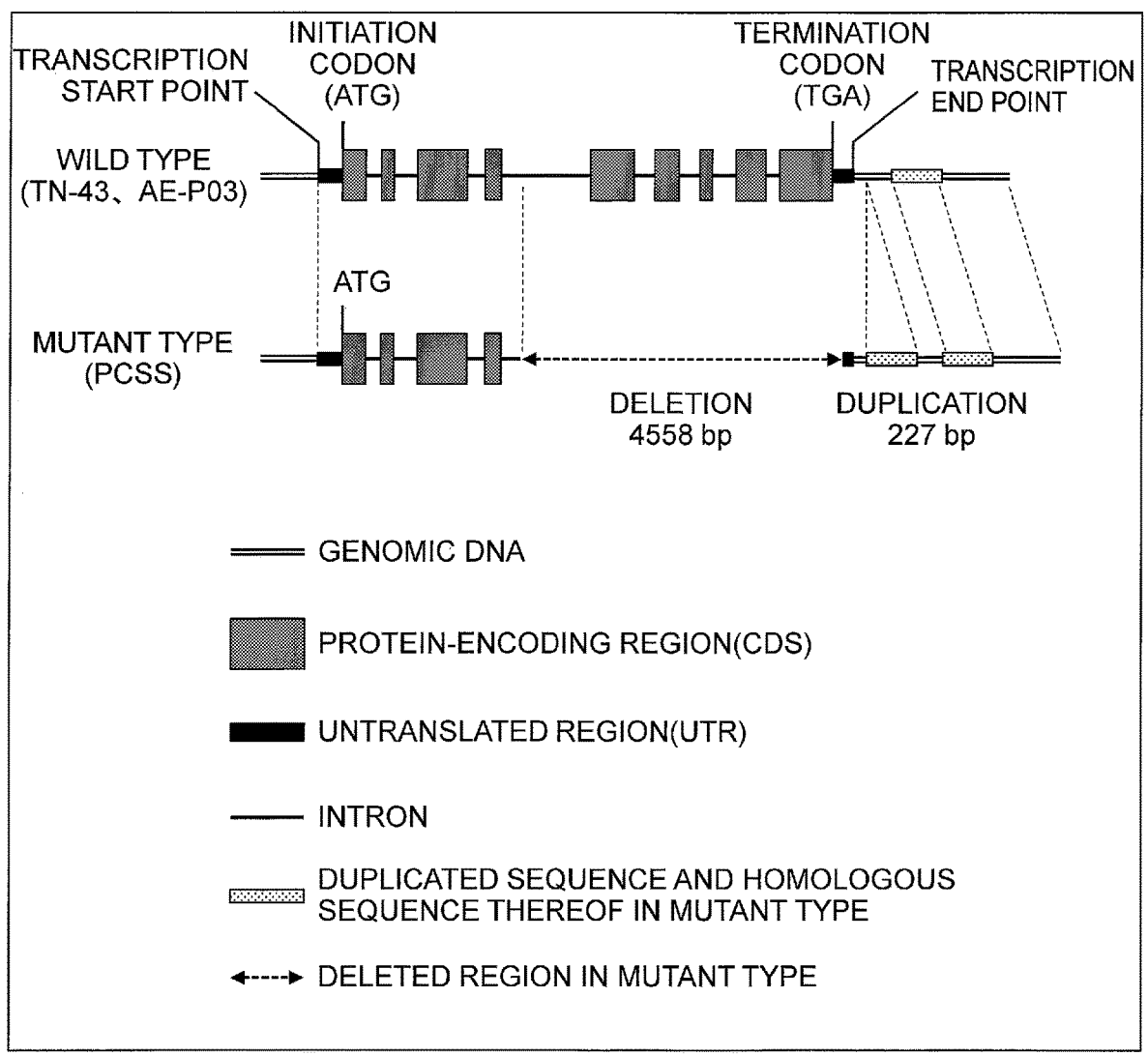
FIG. 5 is a view schematically illustrating a structure of a gene A and a mutation structure of a gene A in a PCSS line, in Example 1 of the present invention.

As is clear from FIG. 5, it was clarified that the gene A of the line PCSS had a great structure mutation as compared with the wild type gene. Therefore, it was strongly suggested that normal mRNA and a normal protein were not produced and accordingly a function of the gene A was completely lost. In view of this, assuming that this deletion mutation was attributed to parthenocarpy, the following experiments were carried out.

<Search of Gene A Deletion Mutation in Eggplant Germplasm Line>

PCR was carried out with the use of (i) as a template, total DNA roughly extracted from a plant by the Edwards method (Reference Literature: Edwards et al. (1991) Nucl. Acids Res. 19: 1349), which is a DNA extraction method well-known in this technical field and (ii) four primers represented by SEQ ID NOs: 49 through 52. According to a deletion type, a clear band of approximately 1 kbp was amplified. According to a wild type, a clear band of approximately 700 bp was amplified. Presence and absence of this deletion and a heterozygote could be each clearly determined. With use of this primer set, 269 items in eggplant germplasm lines collected from all over the world (out of 269 items, 48 items were allied wild species or unidentified) were checked in terms of the presence and absence of the deletion. As a result, a line having such deletion was not found at all. In view of this, it was concluded that the deletion mutation was a natural mutation which newly occurred in the foregoing breeding process.

<Analysis of Deduced Amino Acid Sequence of Gene A Product and Search for Homologous Sequence>

A deduced amino acid sequence of a protein (hereinafter, referred to as a protein A) encoded by the gene A is represented by SEQ ID NO: 1. In a case where this amino acid sequence was analyzed by carrying out BLAST search (http://blast.ncbi.nlm.nih.gov) through a RefSeq database, it was clarified that the amino acid sequence had a given level of sequence identity with an amino acid sequence of a pyridoxal-5'-phosphoric acid (PLP)-dependent amino group transferase (including a deduced sequence by genome decipherment study) which has been reported in various species.

In view of this, genes each of which was expected, by sequence identity search, to encode a protein having a high sequence identity with the protein A were obtained from gene databases of (i) tomato, (ii) *S. pimpinellifolium*, which is a tomato allied species, (iii) *S. tuberosum phureja*, which is potato, (iv) *Capsicum annuum*, which is pepper, and (v) *Malus* x *domestica*, which is apple.

Sequences having the highest sequence identity with the gene A were as follows. That is, in a case of tomato, Solyc03g120450.1.1 (data set name: ITAG2.30, http://solgenomics.net) had the highest sequence identity with the gene A. In a case of tomato allied species *S. pimpinellifolium*, a homologous part (data set name: *S. pimpinellifolium* WGS Contigs, web site: http://solgenomics.net) had the highest sequence identity with the gene A. In a case of potato, Sotub03g036610.1.1 (data set name: Potato ITAG Release 1, web site: http://solgenomics.net) had the highest sequence identity with the gene A. In a case of pepper, TC19330 (data set name: DFCI Pepper Gene Index ver. 4.0, reference literature: Quackenbuch et al., 2001, Nucl. Acid. Res. 29: 159-164, web site: http://compbio.dfci.harvard.edu/tgi/plant.html) had the highest sequence identity with the gene A. In a case of apple, MDP0000310976 (data set name: *Malus* x *domestica* Genome v1.0, reference literature: Velasco et al., 2010, Nature Genetics 42: 833-839, web site: http://www.rosaceae.org) had the highest sequence identity with the gene A. A base sequence of a coding region of a tomato-derived gene is represented by SEQ ID NO: 29, and a deduced amino acid sequence of the tomato-derived gene is represented by SEQ ID NO: 28. A base sequence of a coding region of a tomato allied species *S. pimpinellifolium*-derived gene is represented by SEQ ID NO: 31, and a deduced amino acid sequence of the tomato allied species *S. pimpinellifolium*-derived gene is represented by SEQ ID NO: 30. A base sequence of a coding region of a potato-derived gene is represented by SEQ ID NO: 33, and a deduced amino acid sequence of the potato-derived gene is represented by SEQ ID NO: 32. A base sequence of a coding region of pepper-derived gene is represented by SEQ ID NO: 35, and a deduced amino acid sequence of the pepper-derived gene is represented by SEQ ID NO: 34. A base sequence of a coding region of an apple-derived gene is represented by SEQ ID NO: 37, and a deduced amino acid sequence of the apple-derived gene is represented by SEQ ID NO: 36.

The sequence identity of each of the deduced amino acid sequences with the protein A of eggplant was as follows. That is, in the case of the tomato-derived gene, the deduced amino acid sequence had 94.9% sequence identity with the protein A. In the case of the tomato allied species *S. pimpinellifolium*-derived gene, the deduced amino acid sequence had 94.9% sequence identity with the protein A. In the case of the potato-derived gene, the deduced amino acid sequence had 95.7% sequence identity with the protein A. In the case of the pepper-derived gene, the deduced amino acid sequence had 90.1% sequence identity with the protein A. In the case of the apple-derived gene, the deduced amino acid sequence had 80.5% sequence identity with the protein A. According to *Arabidopsis*, no deduced amino acid sequence had 70% or more sequence identity with the protein A.

<Analysis of Structure of Gene A Transcript in PCSS>

A structure of a transcript of the mutant type gene A was analyzed by the Nested-5'-RACE method and the Nested-3'-RACE method with the use of (i) total RNA extracted from an ovary of the line PCSS and (ii) primers represented by SEQ ID NO: 39 through SEQ ID NO: 42 as with the case of the foregoing methods. As a result, the followings are clarified. That is, a splicing site between the fourth exon and the fourth intron was normal, but an end site of the fourth intron was downstream of a transcription end site of a normal type gene. Accordingly, a PCSS-type transcript was completely different from the normal type gene product in terms of sequences at and subsequent to the fourth exon on a 3' end side. Furthermore, the PCSS-type transcript had a large number of translation termination codons whose reading frames had not been changed. A deduced amino acid sequence of a protein translated from the PCSS-type transcript is represented by SEQ ID NO: 38. (Note that the entire sequence of the amino acid sequence represented by SEQ ID NO: 38 is MGSFGMLARRAVLTDTPVMVQIQELIRGN-KDCISLAQGVVYWQPPAQALEKVKEIIWEPSVSRYG-ADEGLPELREALMQKLGHENNLHKSSVMVTAGAN-QVNEGVQLKVNCLGNYMPLHTYYEERKFSNLSFN*AYGSNYKISSYCP*KIHGCMHCTTAKAAGSETRSAD-RFQH GNPQGEEQESSTYFLCGEEMPASA*GCHKSM-LQHFKWRLP*RYQSPKEEEDHSSWKQLNKCV*SDH-FSRL*SVSISSQVTTKE*P*SQLLRQEVP*TTRKDKRN-QRFSKKRHS*ESYL*CGTININKVGRHRH*F*SKGST-TMQSICL*YI*EFTGCGAN*KAAIKFHGNAPARYHTK-YAGNPCRLDCGGKLVFIPN. The sign "*" in the sequence indicates a translation termination signal given by a termination codon.) This results strongly suggested that, according to the line PCSS, (i) the transcript of the gene A was greatly different in structure from that of the normal type gene, (ii) a mutant type protein A translated from the transcript of the gene A structurally had a great deficit as compared with a normal type protein, and (iii) a function of the protein A was therefore completely lost.

<Isolation of Promotor of Gene A>

It was possible to obtain a sequence of an upstream region of the full-length cDNA sequence of the gene A from a sequence of the BAC clone 08K19. It was deduced that a genomic sequence of the upstream region was a promotor region related to control of expression of the gene A. In view of this, PCR primers (SEQ ID NO: 53 and SEQ ID NO: 54) which amplify the promotor region were synthesized, PCR was carried out with use of (i) the PCR primers and (ii) as a template, genomic DNA of eggplant cultivar "Nakate-shinkuro", and then a fragment of 2173 base pairs represented by SEQ ID NO: 55 was amplified. The fragment included, at its 3' end side, (i) a 5'-end-side untranslated region of 197 base pairs of the full-length cDNA sequence and (ii) a protein coding region of 26 base pairs. Since KOD-plus-NEO (Toyobo Co., Ltd.), which is a heat resisting DNA polymerase having strong 3'-5' exonuclease activity, was used in the PCR, both ends of a resultant amplified fragment were flush ends. Next, a resultant PCR product was digested by XmaI, which is isoschizomer of SmaI, to prepare a fragment whose 5' end was a flush end and whose 3' end was a 5' protruding type sticky end due to XmaI. Meanwhile, pUC198AA-CGN was digested by HindIII, caused to have flush ends with use of a KOD DNA polymerase (Toyobo Co., Ltd.), and then further digested by XmaI. Note that pUC198AA-CGN is a vector obtained by introducing pBI221 (DDBJ/GenBank/EMBL Accession No. AF502128) CaMV35S promotor::GUS::NOS terminator cassette to a HindIII-EcoRI site of a cloning vector pUC198AA (reference literature: Kuroda et al., 2010, Biosci. Biotechnol. Biochem. 74: 2348-2351). A CaMV35S promotor fragment was thus cut out from pUC198AA-CGN, and the foregoing amplified fragment was inserted to the part of pUC198AA-CGN from which part the CaMV35S promotor fragment had been removed. A resultant recombinant plasmid was transformed into *E. coli*, and the recombinant plasmid was extracted from a resultant colony. A base sequence of the recombinant plasmid was checked to select a clone which did not have a sequence mutation caused by PCR amplification. The promoter region (hereinafter, referred to as a promotor A) of the gene A was thus cloned, and was used for the following recombinant plasmid construction. A structure of a resultant vector (hereinafter, referred to pUC198AA-PgeneAGN) is illustrated in (a) of FIG. 6. Note that, in schematic views of vectors in FIG. 6, the promoter A region is shown as Pgene_A. Further, in schematic views of vectors in FIGS. 6 and 13, a NOS terminator region is shown as Tnos, a NOS promoter is shown as Pnos, and a CaMV35S promotor region is shown as P35S.

(3. Production of Parthenocarpic Eggplant Transformant by Mutation of Gene A)

<Construction of Vector for Inducing RNAi (RNA Interference) of Gene A>

A DNA fragment, represented by SEQ ID NO: 58, of 522 by was obtained with the use of (i) cDNA, represented by SEQ ID NO: 3, of the gene A as a template and (ii) primers respectively represented by SEQ ID NO: 56 and SEQ ID NO: 57. This fragment had (i) an XmaI recognition site and a HindIII recognition site at its 5' end and (ii) a SacI recognition site and an XhiO recognition site at its 3' end. The fragment was inserted into a cloning vector pTY262 (DDBJ/GenBank/EMBL Accession No. AB736152) to construct a RNAi-induction chimeric gene for the gene A. This pTY262 vector has an expression cassette including a CaMV35S promotor and a NOS terminator. In the pTY262 vector, cloning sites of an exogenous sequence are arranged so as to sandwich the first intron of a tomato tubulin gene.

First, the fragment of 522 bp (SEQ ID NO: 58) was digested by HindIII and SacI, and then inserted ahead of the NOS terminator. Next, a resultant vector was digested by XhoI, caused to have blunt ends with use of a KOD DNA polymerase (Toyobo Co., Ltd.), and then digested by XmaI. The fragment of 522 bp was digested by SacI, similarly caused to have flush ends with use of a KOD DNA polymerase (Toyobo Co., Ltd.), and then digested by XmaI. The fragment of 522 bp was then inserted ahead of the CaMV35S promoter of the foregoing linear vector. A resultant RNAi-induction chimeric gene had a structure in which the substantially entire fragment of 522 bp represented by SEQ ID NO: 58 was arranged in an inverted repeat sequence into which the first intron of the tomato tubulin gene was inserted. Expression of the RNAi-induction chimeric gene was induced by the CaMV35S promoter which induces constitutive expression of general plants (see (b) of FIG. 6). Note that, in the schematic view of the vectors in FIG. 6, the DNA fragment of 522 bp of the gene A is shown as RNAi-A. Note also that, in the schematic views of the vectors in FIGS. 6 and 13, a region of the first intron of a tomato tubulin gene is shown as TUA6_intron. The entire inverted repeat sequence of this vector pTY262-CgeneA-RNAiN was then (i) digested by a restriction enzyme KpnI, (ii) caused to have flush ends, (iii) cut by a SacI process, and (iv) inserted into a site from which a GUS gene of the vector pUC198AA-PgeneAGN was cut by a SmaI process and a SacI process. An RNAi-induction chimeric gene was thus constructed. A resultant RNAi-induction chimeric gene pUC198AA-PgeneA-RNAiN had an inverted repeat sequence identical, in structure, to that of the vector pTY262-CgeneA-RNAiN. Expression of the RNAi-induction chimeric gene pUC198AA-PgeneA-RNAiN was induced by the promoter A (see (c) of FIG. 6). This chimeric gene was cut by a restriction enzyme AscI, and inserted to an AscI recognition site of a binary vector pZK3BGFP which had been uniquely constructed by introducing a CaMV35S promotor::sGFP:: NOS terminator expression cassette (Reference Literature: Chiu et al., 1993, Curr. Biol. 6: 325-330) to a binary vector pZK3 (Reference Literature: Kuroda et al., 2010, Biosci. Biotechnol. Biochem. 74: 2348-2351). A binary vector pZK3BGFP-PgeneA-RNAiN was thus constructed (see (d) of FIG. 6).

<Production of Eggplant Transformant by RNAi>

An eggplant transformant was produced to which the binary vector for RNAi interference was introduced. A concrete method of producing the eggplant transformant was as follows. First, with the Agrobacterium method (Reference Literature: Billings, S et al., 1997, J Amer. Hort. Sci 122: 158-162), a cotyledon of eggplant cultivar "Nakateshinkuro" was infected with Agrobacterium having a binary vector, cultured on a kanamycin-containing medium, and selected. A redifferentiated plant was thus obtained. Whether or not gene transfer of the redifferentiated plant succeeded was evaluated by fluorescence expression by a marker gene GFP and checking by PCR of a transgene, and a transgenic plant at the original generation of transformation was obtained. Furthermore, among the first selfed generation of the transgenic plant, (i) an individual having a transgene as a homozygote and (ii) an individual having no transgene due to genetic segregation were each selected by quantitative PCR.

<Study of Parthenocarpy of Eggplant Transformant>

Figure 7:
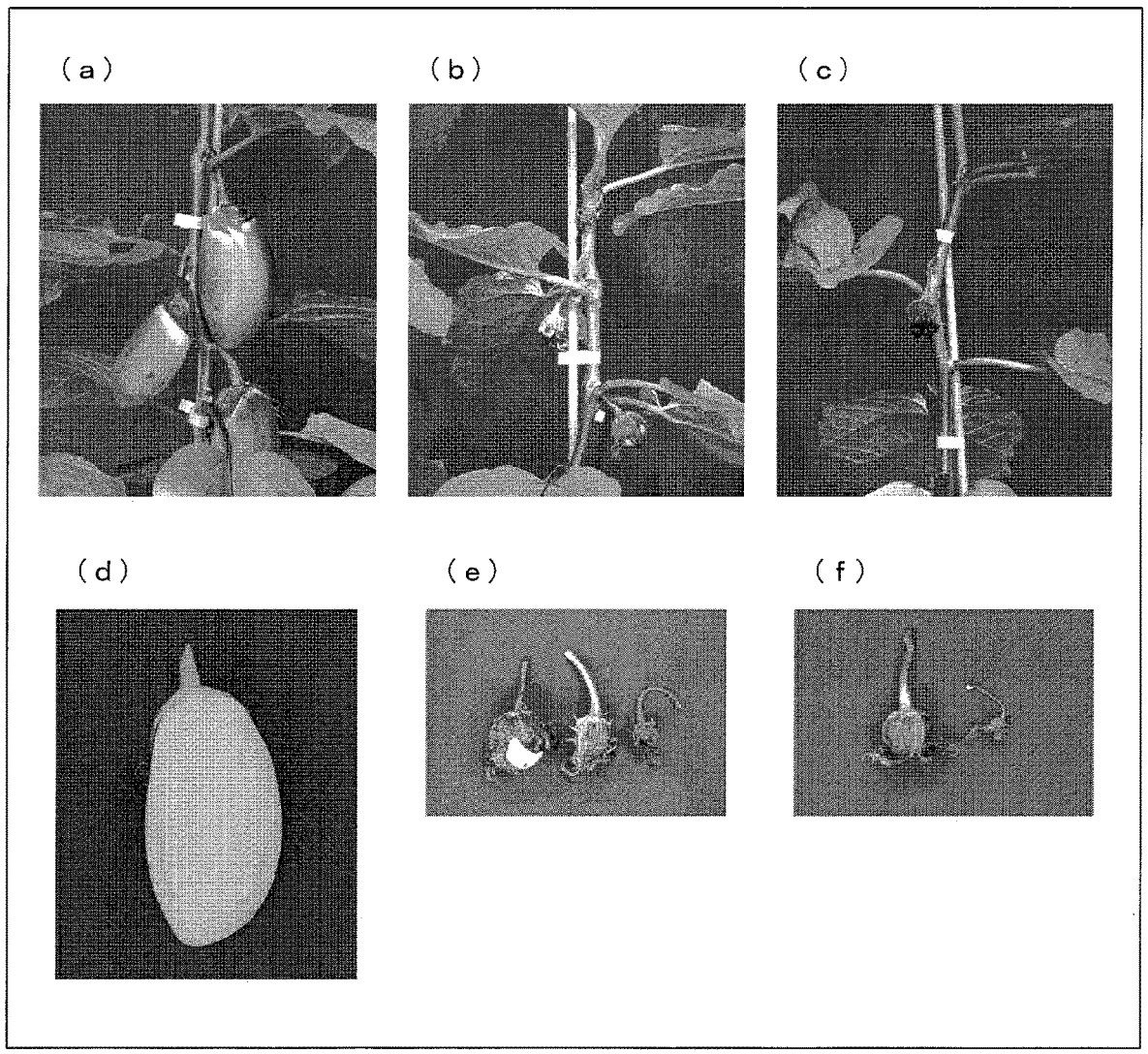
FIGS. 7A-F present views illustrating parthenocarpy of an eggplant transformant in Example 1 of the present invention.

An individual (12012-1_homozygote) which was of the eggplant transformant and had been selected as above was cultivated, and its parthenocarpy was checked by observing growth (enlargement) from an ovary, whose stigma had been removed before anthesis, to a fruit. Concurrently, (i) an original cultivar "Nakateshinkuro" (control) which was a non-transformant and (ii) an individual (12012-1_null) which had been derived from a transformant but lost a transgene by genetic segregation were cultivated and observed, as controls, in terms of growth (enlargement) of a fruit which had been subjected to similar treatment and normal open pollination. FIG. 7 show results of this. As shown in FIG. 7, even in the case where pollination had been prevented by removing the stigma before anthesis, the fruit of the individual 12012-1_homozygote which was a transformant having a transgene as a homozygote showed evident growth (enlargement), and thus showed parthenocarpy ((a) of FIG. 7). Moreover, it was confirmed that no seeds were formed in the individual 12012-1_homozygote because the 12012-1_homozygote was not pollinated ((d) of FIG. 7). On the other hand, in the individual 12012-1_null ((b) of FIG. 7), the fruit was hardly enlarged, as with the control ((c) of FIG. 7). With regard to the individual 12012-1_null and the control, (e) and (f) of FIG. 7 respectively show states of fruits which were insufficiently enlarged due to non-pollination.

Figure 8:
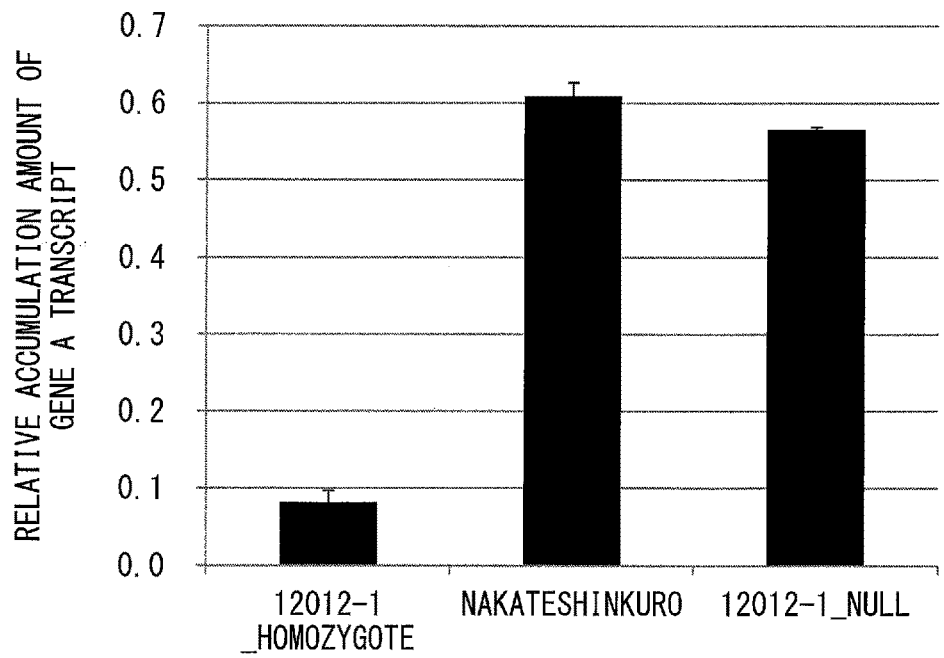
FIG. 8 is a view illustrating an accumulation amount of a transcript of parthenocarpic gene A in each of eggplant transformants in Example 1 of the present invention.

All RNAs were extracted, at anthesis, from ovaries of the eggplant transformant (individual 12012-1_homozygote), the non-transformant (control) of the original cultivar "Nakateshinkuro", and the individual (12012-1_null) which had lost a transgene, and cDNA was synthesized with the use of Superscript VILO cDNA synthesis kit (Life Technologies Corporation), while using all the RNAs as templates. While using the obtained cDNA as a template, an mRNA accumulation amount of the gene A was measured by quantitative PCR with the use of, as primers, oligonucleotides represented by SEQ ID NO: 45 and SEQ ID NO: 46, respectively. FIG. 8 shows results of this. As shown in FIG. 8, in the transformant (12012-1_homozygote), expression of the gene A in the ovary at anthesis was greatly inhibited.

Moreover, the individual 12012-1_null which had lost the transgene and did not show parthenocarpy at all had a gene A expression level which was substantially identical with that of the control (non-transformant), as with the growth (enlargement) state of the fruit.

From the above results, it was clarified that parthenocarpy was induced in eggplant by inhibiting expression of the gene A.

(4. Quantitative Determination of Indole Acetic Acid (IAA) Concentration and IAA Metabolite Concentration in Parthenocarpic Eggplant Line PCSS)

<Quantitative Determination of Indole Acetic Acid (IAA) Concentration and IAA Metabolite Concentration in Parthenocarpic Eggplant Line PCSS, by LC/MS/MS Analysis>

In order to quantitatively determine an IAA amount and an IAA metabolite amount in the parthenocarpic eggplant line PCSS, LC/MS/MS analysis was carried out on the line PCSS serving as an experimental material.

In a case where LC/MS/MS analysis is carried out on an auxin metabolite or the like while using *Arabidopsis* as a material, an extract is extracted from a plant body with the use of a sodium phosphate buffer. It is said that the auxin metabolite or the like can be analyzed while using a solution, in which the extract is purified by an OASIS HLB column (Nihon Waters K.K.), as a sample (Reference Literature: Novak et al., 2012, Plant Journal. 72: 523-536). However, in a case where an ovary of eggplant was used, it was highly difficult to carry out, with the use of LC/MS/MS, analysis on a sample obtained by the above purification method, due to influence of ion suppression by impurities. Under the circumstances, an eluate by the OASIS HLB was segregated into (i) a mixed fraction of an acidic substance and a neutral substance and (ii) a basic substance fraction by an OASIS MCX column (Nihon Waters K.K.). Further, the obtained mixed fraction of an acidic substance and a neutral substance was segregated into the acidic substance and the neutral substance by an OASIS WAX column (Nihon Waters K.K.), and samples thus obtained were subjected to LC/MS/MS analysis. By using the samples purified by the purification method, it was possible to carry out LC/MS/MS analysis on indole acetic acid (IAA) which was an active substance contained in each of the samples. Moreover, by this analyzing method, it was possible to carry out LC/MS/MS analysis on a small amount of a sample that was obtained from one ovary of eggplant. Meanwhile, an indole pyruvic acid (IPyA) which is a precursor of IAA was a highly unstable substance, and therefore an extract was derivatized by cysteamine, and analyzed after purification by the OASIS HLB. The purified substance thus obtained was analyzed by LC/MS/MS (mass spectrometer) (3200 QTRAP, AB SCIEX). Segregation by an HPLC of LC/MS/MS was carried out by a Shim-pack XR-ODS column (Shimadzu Corporation) and the segregated substance was ionized by ESI (electron spray ionization) and introduced to MS/MS. Then, detection of molecular ions and fragment ions generated in a MRM (Multiple Reaction Monitoring) mode was carried out.

Figure 9:
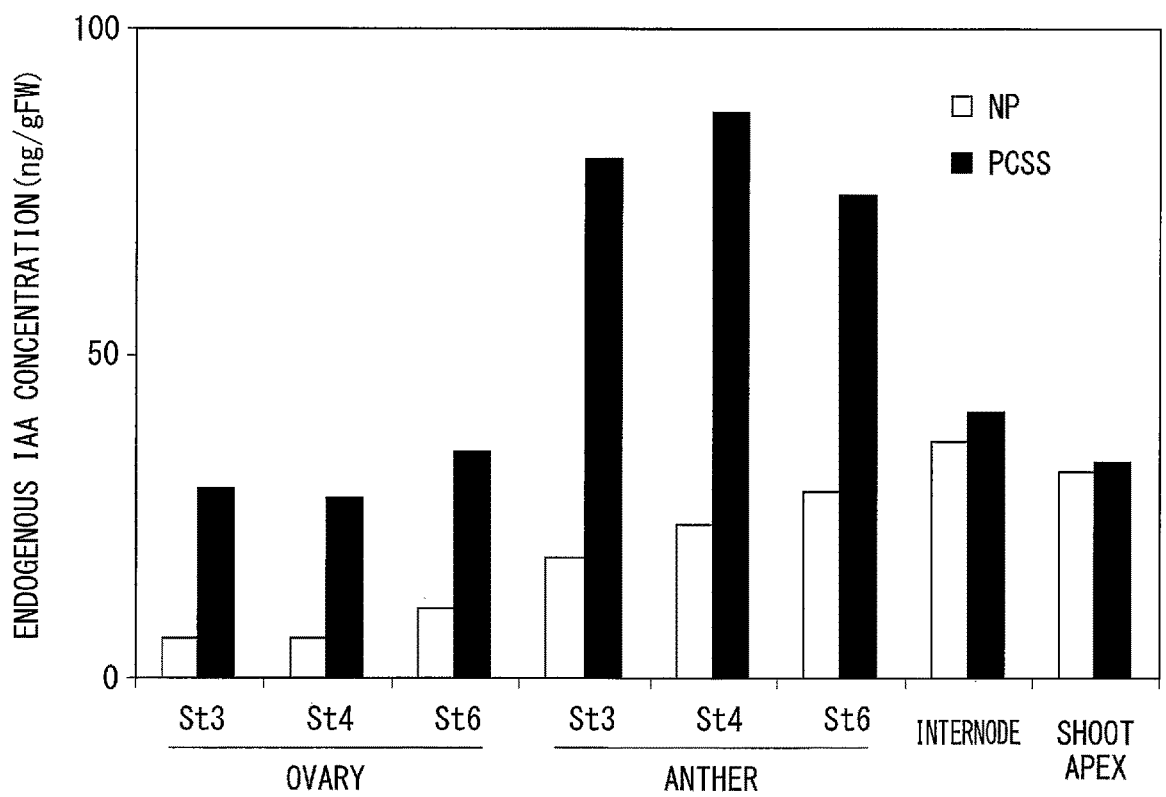
FIG. 9 is a view illustrating an endogenous IAA concentration in a parthenocarpic eggplant line PCSS, in Example 1 of the present invention.

With regard to ovaries and anthers of buds (of approximately 5 days before anthesis, before petal coloring and approximately 2 days before anthesis, at petal coloring) of the parthenocarpic eggplant line PCSS and an ovary, an anther, an internode, and a shoot apex of the line PCSS at anthesis, endogenous IAA concentrations were measured by carrying out quantitative analysis by the above described method. Moreover, for comparison, a selfed line NP of non-parthenocarpic eggplant was similarly measured as a control. The selfed line NP of the non-parthenocarpic eggplant was a non-parthenocarpic line bred by a crossing combination identical with that of the line PCSS. FIG. 9 shows measurement results. As shown in FIG. 9, no difference in endogenous IAA amount between the line PCSS and the line NP was seen at the shoot apex and the internode.

Meanwhile, in the ovary and the anther, endogenous IAA concentrations which were approximately 2.6 to 4.6 times higher than those of the line NP were observed in the line PCSS at all the measured developing stages (i.e., before petal coloring, at petal coloring, and at anthesis).

Figure 10:
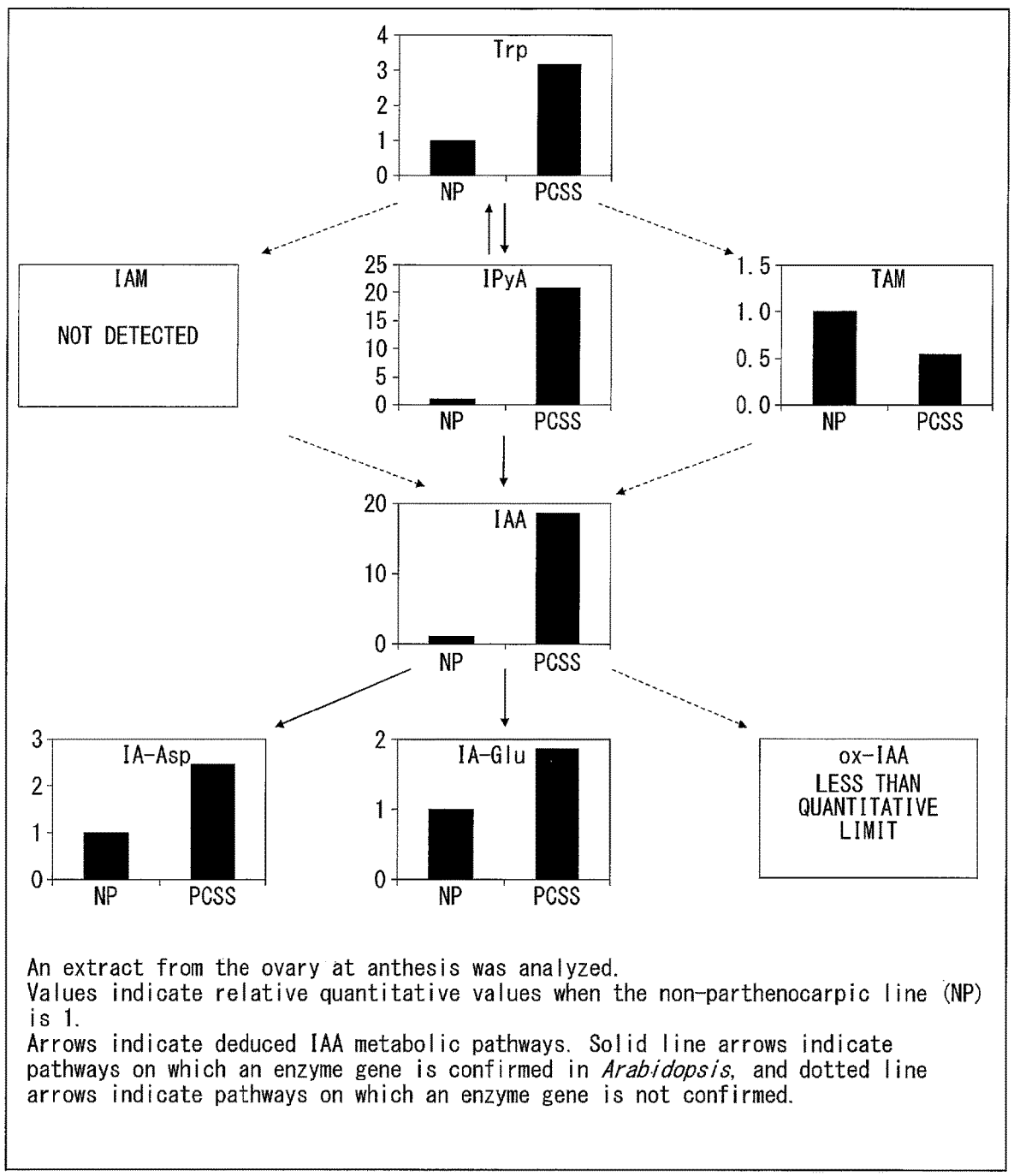
FIG. 10 is a view illustrating an intermediate product concentration in an endogenous IAA synthesis pathway or an IAA metabolite concentration in a parthenocarpic eggplant line PCSS, in Example 1 of the present invention.

Further, an ovary of the line PCSS at anthesis was analyzed in terms of IAA metabolite and the like by a similar method. FIG. 10 shows results of this. It was clarified that IPyA and IAA were accumulated in the line PCSS with a notably high concentration, as compared with the line NP. Meanwhile, the line PCSS and the line NP were not notably different from each other in terms of accumulation of IAM, TAM, oxIAA, IAAsp, and IAGlu each of which was an intermediate product in another IAA synthesis pathway or a metabolite of IAA.

<Quantitative Determination of Indole Acetic Acid (IAA) Concentration in Gene A Inhibited Transgenic Eggplant line 12012-1_Homozygote, by LC/MS/MS Analysis>

Figure 11:
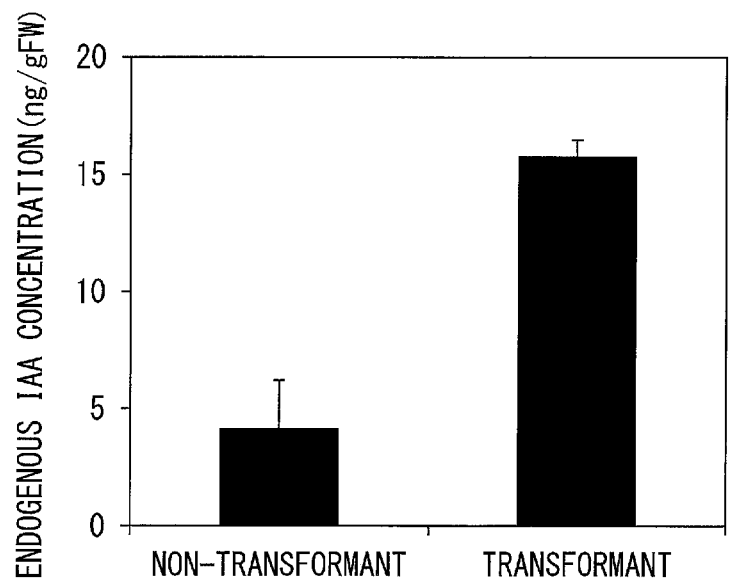
FIG. 11 is a view illustrating an endogenous IAA concentration in an eggplant transformant, in Example 1 of the present invention.

Next, IAA was extracted from an ovary of a gene A inhibited transgenic eggplant line 12012-1_homozygote, and quantitative analysis was carried out with a method similar to that in the case where the line PCSS was used. FIG. 11 shows results. As a result, as shown in FIG. 11, an endogenous IAA concentration, which was approximately 4 times on average higher than that of the non-transformant (cultivar "Nakateshinkuro"), was observed in an ovary of an eggplant transformant in which expression of the gene A was inhibited.

From the above results, it was suggested that the parthenocarpic gene A encoded an amino group transferase. Further, it was suggested that the amino group transferase was an amino group transferase that had an enzyme activity similar to that of VAS1 of *Arabidopsis* for synthesizing tryptophan while using IPyA as a ground substance. Further, it was strongly suggested that (i) the endogenous IAA concentration could be increased in a flower organ of a solanaceous product to a level at which practical parthenocarpy is induced, by inhibiting expression of the gene and (ii) consequently a solanaceous plant encompassing tomato and eggplant showed parthenocarpy.

(5. Measurement of Activity of Protein A Encoded by Gene A)

<Analysis of Function of Protein A Encoded by Gene A, with Use of Transgenic Protein Transiently Expressed in Wild Species of Tobacco>

A DNA fragment (SEQ ID NO: 69) made up of 24 bases was added ahead of a termination codon of a cDNA sequence of the gene A so that a reading frame would not be changed, and thus a chimeric gene was constructed from which a gene product is produced in which a Strep-tag II sequence, i.e., Trp-Ser-His-Pro-Gln-Phe-Glu-Lys (Reference Literature: Schmidt et al., 1996, J. Mol. Biol. 255: 753-766) is added to a C end of the protein A encoded by the gene A. An expression construct was produced by replacing this gene with a GUS gene of pUC198AA-CGN, and further a transformation binary vector was produced by introducing the expression construct into a binary vector pZK3BGFP. An *Agrobacterium* suspension retaining the vector was injected into the inside of a leaf tissue via stomata of an unfolded leaf of *Nicotiana benthamiana* (which is a wild species of tobacco) so that the gene was transiently expressed in the leaf of tobacco, and thus the transgenic protein A having the Streptag sequence at the C end was synthesized. On the third day from the injection treatment, a crude protein was extracted from the treated leaf with a phosphoric acid buffer, and the transgenic protein A was purified by chromatography with the use of Strep-Tactin Sepharose column (IBA GmbH). Moreover, as a control, a GUS gene was constructed in which a Strep-tag II sequence was added to a C end of an *E. coli*-derived GUS gene, and a transgenic GUS protein was purified with similar procedures.

Figure 12:
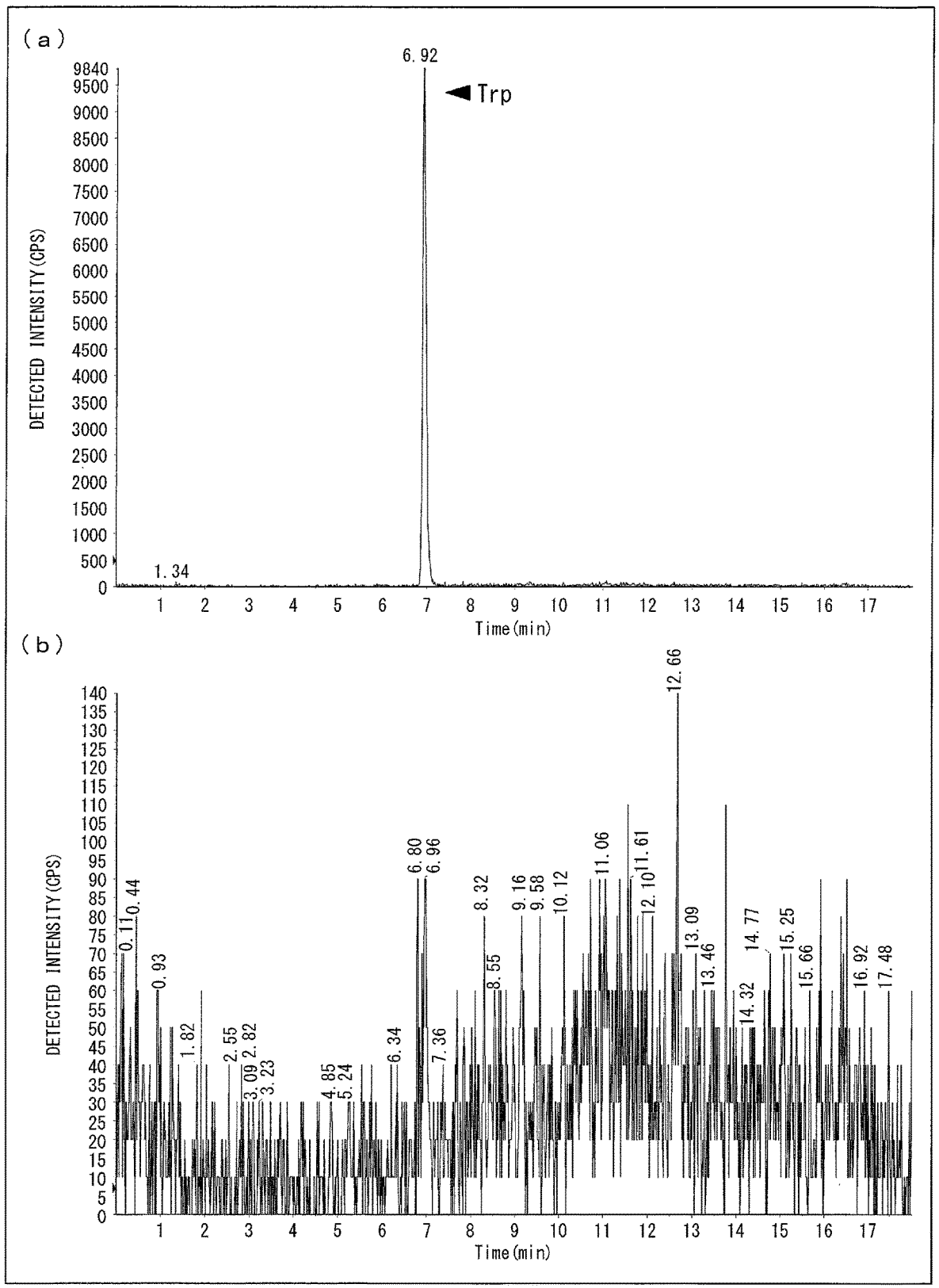
FIG. 12A and FIG. 12B present views illustrating amino group transferase activity, in Example 1 of the present invention.

To each of solutions of the respective proteins thus obtained (2 µg/µL), an amino acid mixed solution (Arg, Gln, Cys, Asp, Gly, Met, Phe, and Glu) (concentration of each amino acid in the solution: 5 mM), pyridoxal phosphate, and IPyA (500 µM) were added, and each of the mixtures was reacted in a 50 mM sodium phosphate buffer (pH 7.4) at 30° C. for 2 hours. Then, each of the reaction solutions was purified by an OASIS HLB column, and analyzed with the use of LC/MS/MS. Results are shown in FIG. 12. As shown in (a) of FIG. 12, tryptophan depending on the transgenic protein A was produced. Note that tryptophan was not detected in a case where the transgenic GUS protein was used (see (b) of FIG. 12). From this, it is clear that production of tryptophan from the leaf tissue of *N. benthamiana* (wild species of tobacco) from which the protein was extracted is not higher than a detection limit.

From the above results, it was confirmed that the protein A encoded by the gene A was an amino group transferase that catalyzes reaction to synthesize tryptophan by using IPyA and amino acid as substrates.

Example 2

Tomato-Derived Parthenocarpic Gene tA (1. Identification and Analysis of Tomato-Derived Parthenocarpy Responsible Gene tA)

<Preparation of cDNA Fragment of Tomato Homologue of Gene A of Eggplant>

Figure 13:
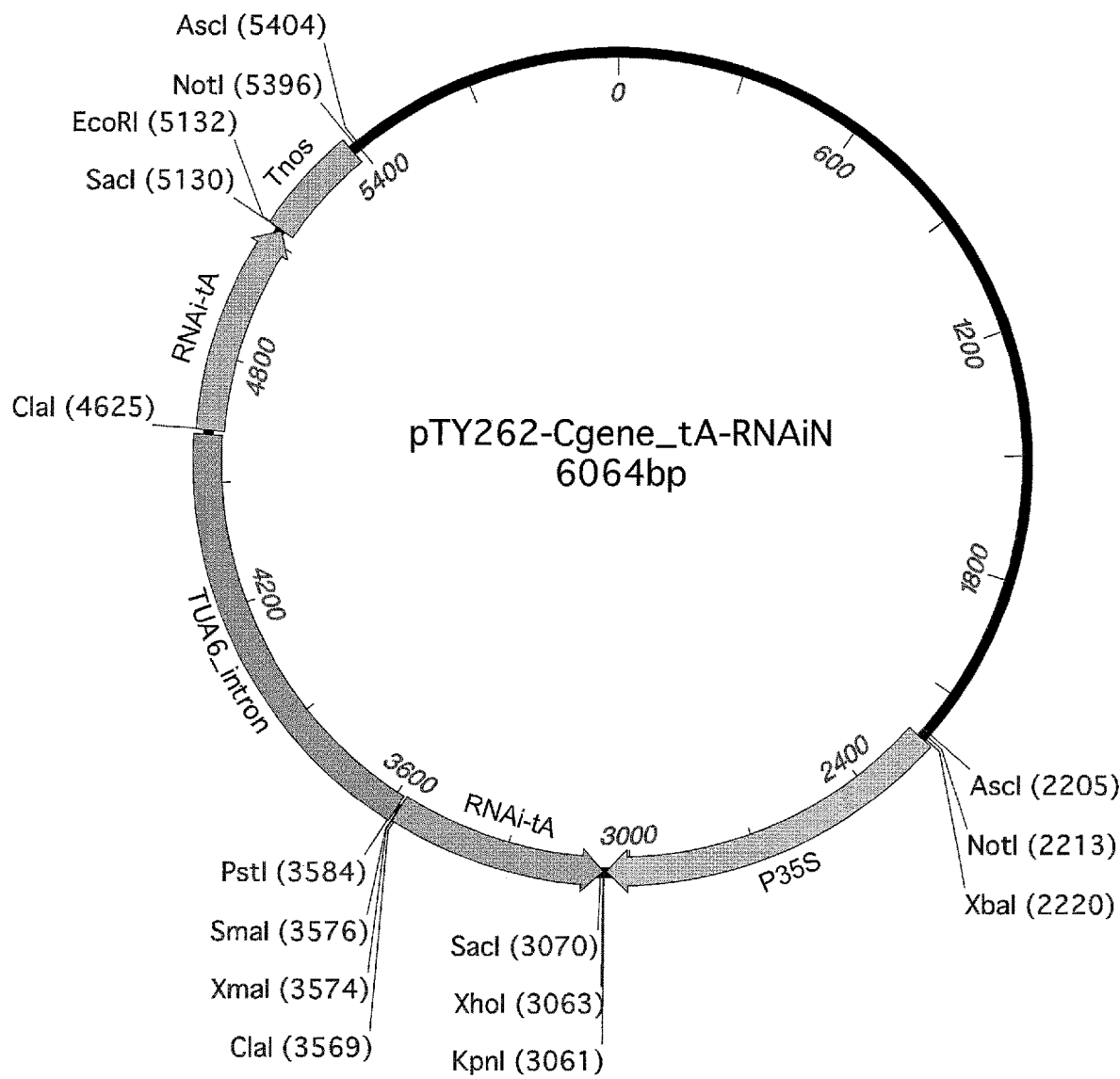
FIG. 13(a) is a view schematically illustrating a vector constructed during preparation of an RNAi induction vector, in Example 2 of the present invention.
FIG. 13(b) is a view schematically illustrating an RNAi induction vector, in Example 2 of the present invention.
FIG. 13(c) is a view schematically illustrating a vector having a promoter sequence of a gene tA, in Example 2 of the present invention.
FIG. 13(d) is a view schematically illustrating an RNAi induction vector, in Example 2 of the present invention.
Figure 13:
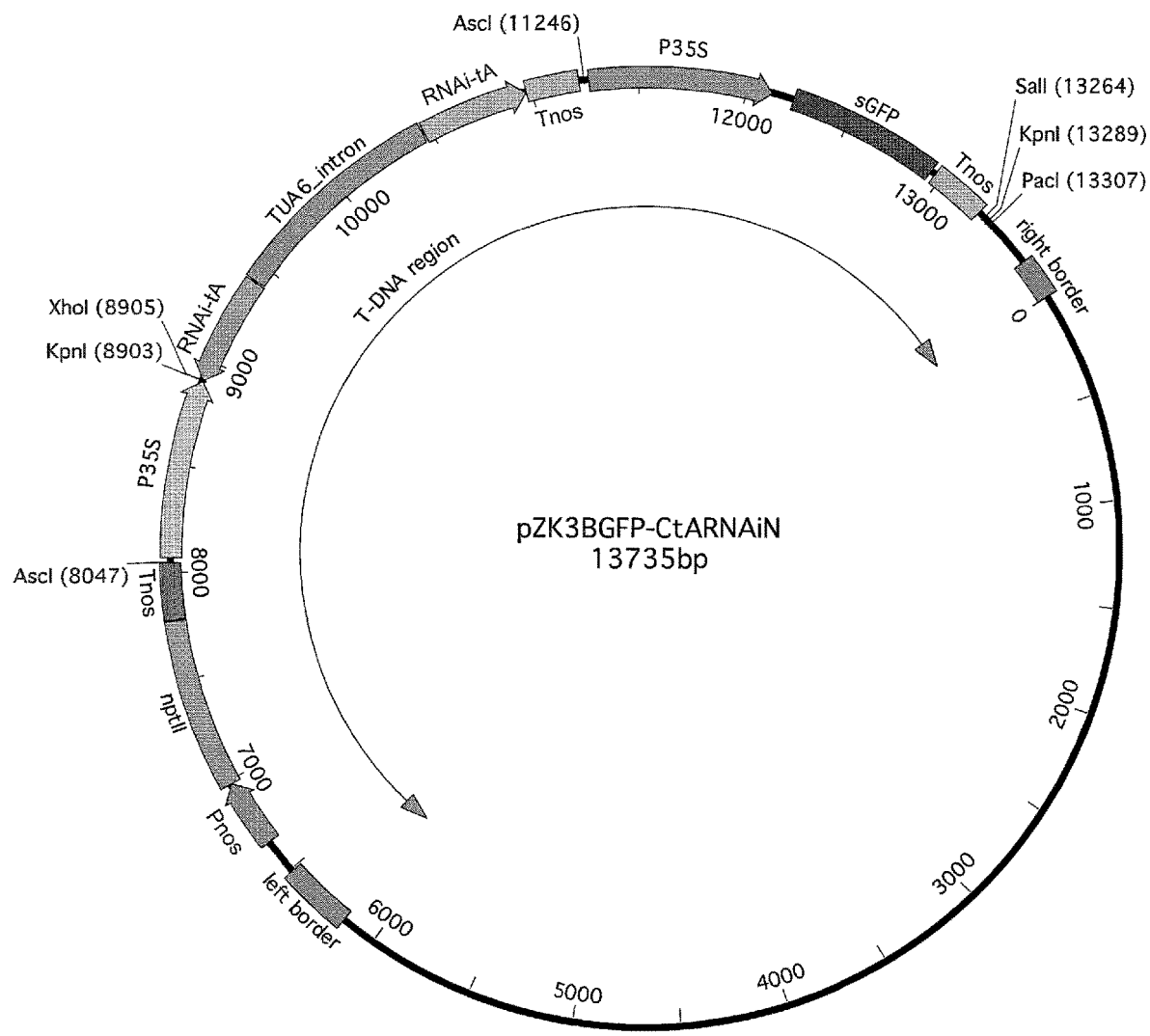
Figure 13:
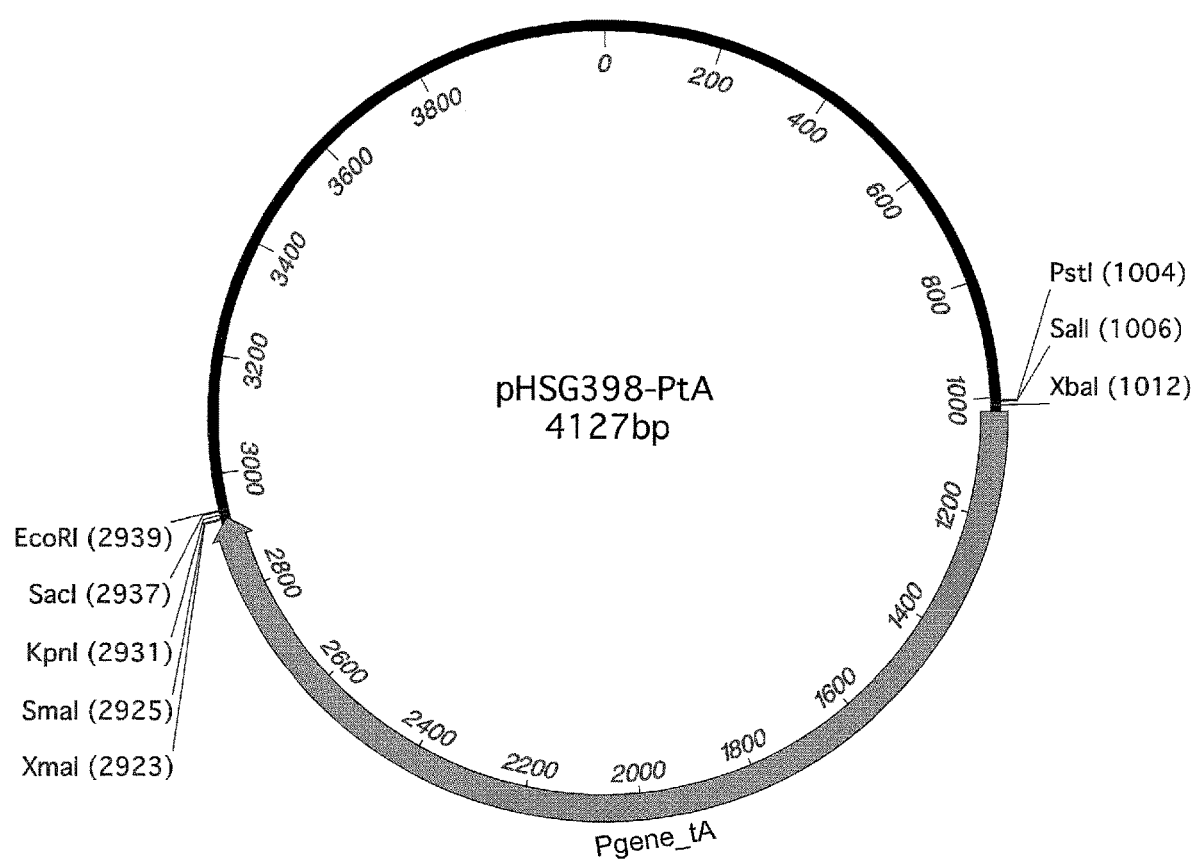
Figure 13:
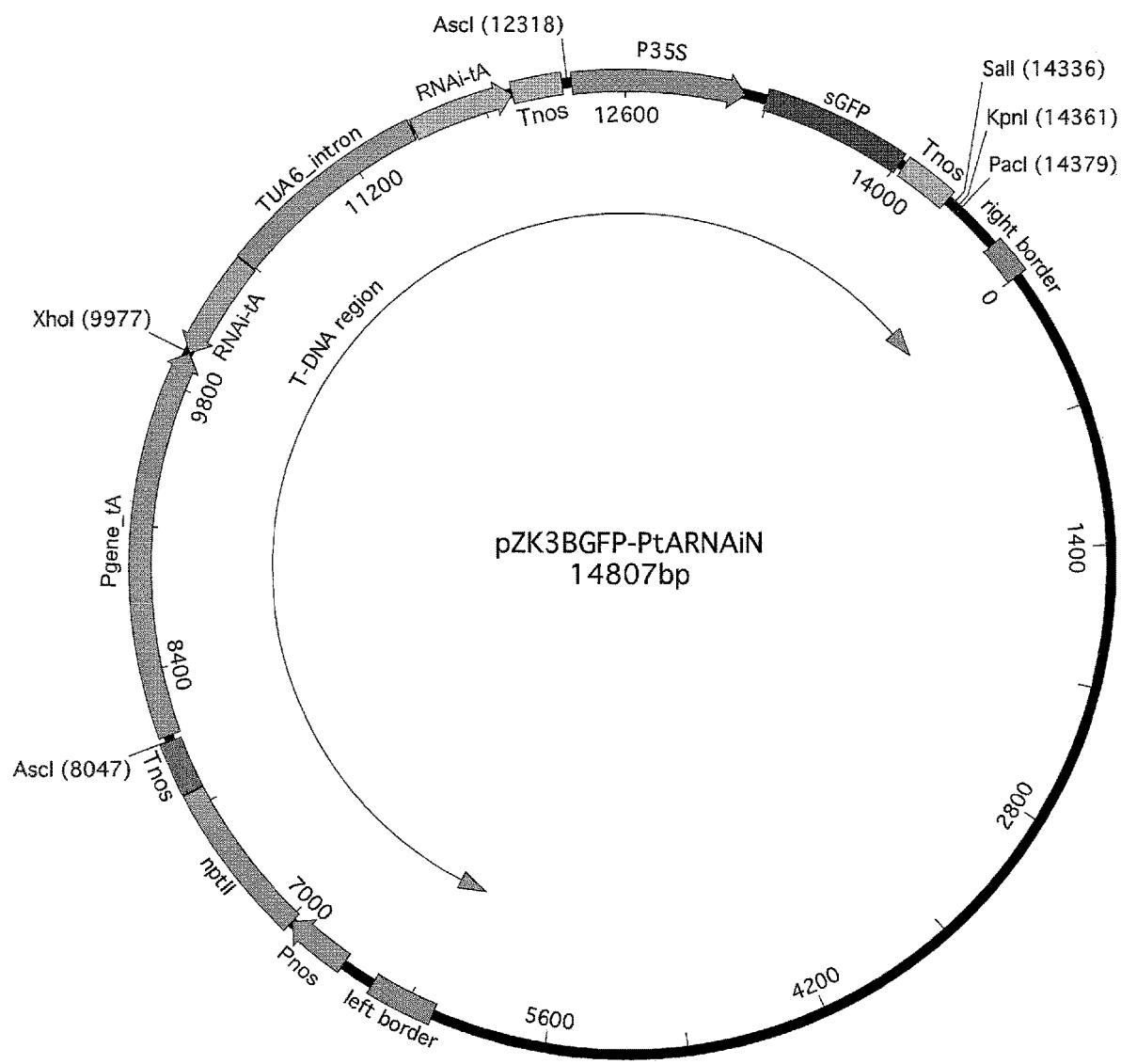

By carrying out BLASTP search in deduced amino acid sequence database (database name: ITAG2.30, web page http://www.solgenomics.net) of structural genes deduced from a genomic sequence of tomato (Reference Literature: The Tomato Genome Consortium 2012, Nature 485: 635-641) while setting a deduced amino acid sequence of the protein A as a query sequence, a tomato homologue gene tA was obtained which was deduced to encode a protein that has a sequence identity of 95% relative to the gene A. The tomato homologue gene tA had a base sequence that was the sequence represented by SEQ ID NO: 29 described in <Analysis of deduced amino acid sequence of gene A product and search for homologous sequence> above. Based on the base sequence, a pair of primers (SEQ ID NO: 59 and SEQ ID NO: 60) for amplifying a part of the base sequence was synthesized. From all RNAs extracted from a flower and a bud of a tomato cultivar "Shugyoku", cDNA was synthesized with the use of a transcriptor first strand cDNA synthesis kit (Roche Diagnostics K.K.) While using the cDNA as a template, PCR was carried out with the use of the pair of primers, and thus a DNA fragment of 523 bp represented by SEQ ID NO: 61 was obtained. In the fragment, (i) a recognition site for a restricted enzyme XmaI and a restricted enzyme ClaI are added to a 5' end of a cDNA-derived sequence of 496 bp and (ii) a recognition site for a restricted enzyme SacI and a restricted enzyme XhoI are added to a 3' end of the cDNA-derived sequence. The fragment was treated by ClaI and SacI and then introduced into pTY262, and the above described fragment was treated by XhoI and XmaI and then introduced into a plasmid of the pTY262. Thus, an RNAi-induction chimeric gene having an inverted repeat sequence structure was constructed. Absence of mutation of the base sequence of the introduced fragment was confirmed by sequencing, and thus a clone having a correct sequence was selected. A structure of this vector pTY262-Cgene_tA-RNAiN is illustrated in FIG. 13(*a*). The vector pTY262-Cgene_tA-RNAiN is further treated by AscI, and an expression cassette of a cut-out gene tA was inserted into an AscI site of pZK3BGFP. A structure of a binary vector pZK3BGFP-CtARNAiN thus obtained is illustrated in FIG. 13(*b*). Note that, in the schematic views of vectors in FIG. 13, the DNA fragment of 523 bp in the gene tA is indicated by "RNAi-tA".

<Isolation of Promoter of Tomato Homologue Gene tA>

With reference to a tomato genomic sequence, 1908 base pairs of a genomic fragment (SEQ ID NO: 62) including 1870 bp in a part upstream of a translation start site of the gene tA and 29 bp of a protein coding region downstream of the translation start site was amplified from a genomic DNA of the tomato cultivar "Shugyoku" with the use of a pair of primers represented by SEQ ID NO: 63 and SEQ ID NO: 64. KOD-plus-NEO (Toyobo Co., Ltd.) which is heat resisting DNA polymerase having a strong 3'-5' exonuclease activity was used in PCR reaction, and therefore both ends of the amplified fragment were flush ends. Moreover, the fragment had an XmaI recognition site derived from the primer (SEQ ID NO: 64) at the 3' end. A cloning vector pHSG398 (Takara Bio Inc.) was (i) treated by a restricted enzyme BamHI, (ii) made to have flush ends with the use of KOD DNA polymerase (Toyobo Co., Ltd.), (iii) mixed with the above fragment, (iv) treated by a restricted enzyme XmaI, and then (v) ligated with the use of T4 DNA ligase (Promega Corporation), and (vi) introduced into *E. coli*. Thus, a promoter region (hereinafter, referred to as "promoter tA") of the tomato homologue gene tA was cloned. Further, a clone pHSG398-PtA having no mutation was selected by sequencing. FIG. 13(*c*) illustrates a structure of the clone pHSG398-PtA. Note that, in the schematic views of vectors in FIG. 13, a region of the promoter tA is indicated by "Pgene_tA". Further, the pHSG398-PtA was treated by SmaI and XbaI and a promoter tA fragment was cut out. Then, an expression cassette in a structure of a plasmid pTY262-Pgene_tA-RNAiN, in which the cut out promoter tA fragment was replaced with a CaMV35S promoter of the pTY262-Cgene_tA-RNAiN, was inserted into an AscI site of pZK3BGFP. A structure of the binary vector pZK3BGFP-PtARNAiN thus obtained is illustrated in FIG. 13(*d*).

<Production of Tomato Transformant in which Expression of Gene to is Inhibited, by RNAi>

With the use of the binary vectors pZK3BGFP-PtARNAiN and pZK3BGFP-CtARNAiN constructed by the above procedures, a tomato transformant was produced with an *Agrobacterium* method. Specifically, with the use of the *Agrobacterium* method (Reference Literature: Sun et al., 2006, Plant Cell Physiol. 47: 426-431), a cotyledon of a tomato cultivar "Ailsa Craig" was infected with *Agrobacterium* having a binary vector, and cultured on a kanamycin-containing medium. Then, selection was carried out and thus a redifferentiated plant was obtained. Whether or not gene transfer of the redifferentiated plant succeeded was evaluated by fluorescence expression by a marker gene GFP and checking by PCR of a transgene, and a transgenic plant at the original generation of transformation was obtained.

<Study of Parthenocarpy of Tomato Transformant>

Figure 14:
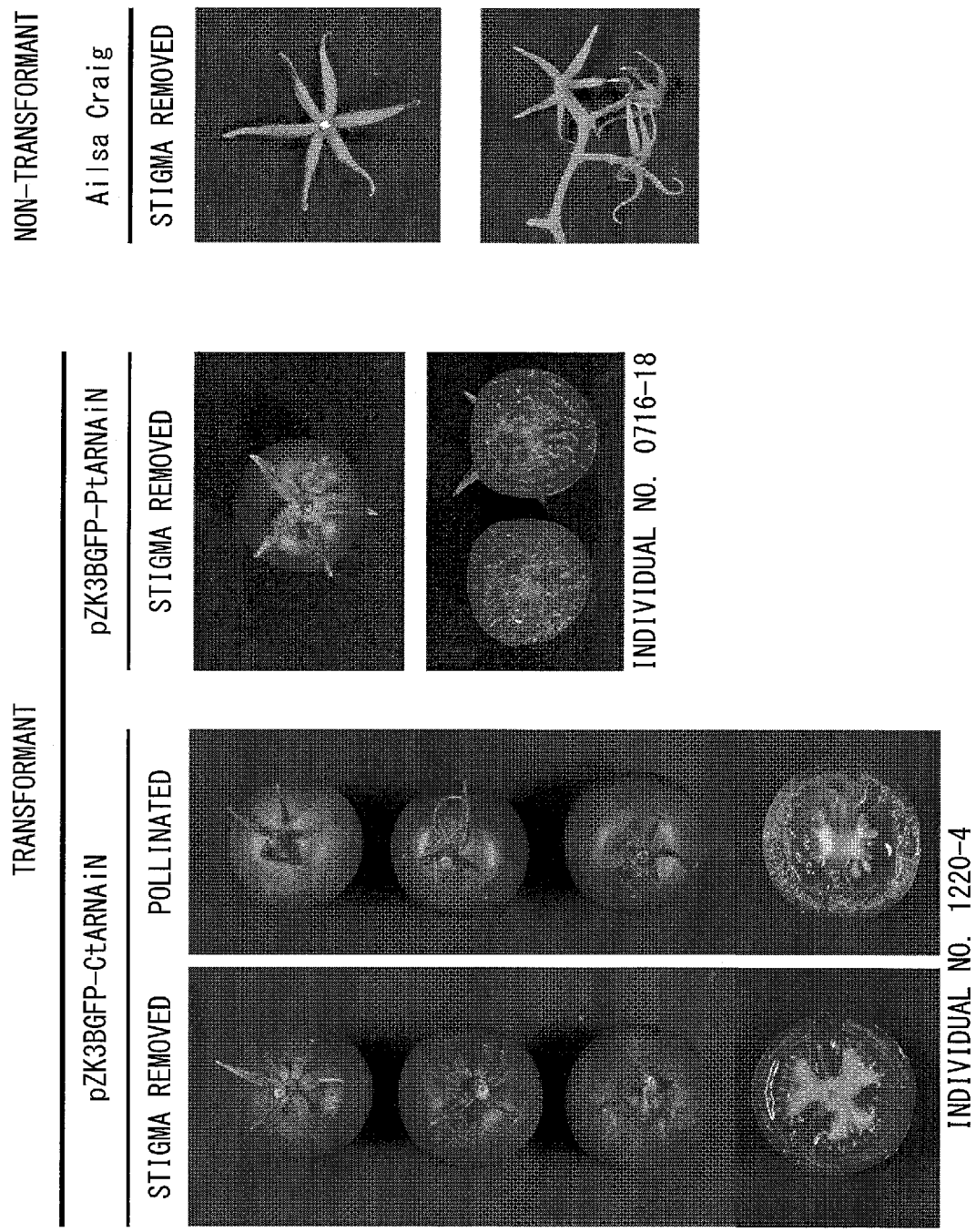
FIG. 14 is a view illustrating parthenocarpy of a tomato transformant, in Example 2 of the present invention.

An individual of the tomato transformant obtained by the above selection was cultivated, a stigma of the individual was removed before anthesis, and parthenocarpy of the individual was checked. Moreover, a non-transformant (control) of a tomato original cultivar "Ailsa Craig" was concurrently cultivated, and a stigma thereof was similarly removed. Thus, the non-transformant was used as a control. Further, with regard to the tomato transformant, an enlargement/maturation state of a fruit which had been subjected to normal open pollination was observed. FIG. 14 shows results of this. As shown in FIG. 14, an enlarged fruit was not formed at all from the tomato cultivar "Ailsa Craig" i.e., the non-transformant from which the stigma had been removed. On the other hand, with regard to the transformant (individual No. 1220-4) in which expression of the gene tA was inhibited by RNAi induction with the use of the CaMV35S promoter, the stigma-removed fruit was enlarged similarly to a fruit which had been subjected to open pollination and had formed seeds, and thus a ripe fruit having no seed was obtained. Moreover, also with regard to the case (individual No. 0716-18) where a gene tA promoter was used, the stigma-removed fruit was enlarged (i.e., grew) and thus became a ripe fruit. The above clarified that parthenocarpy can be given to tomato by artificially inducing inhibition of expression of the gene tA.

Figure 15:
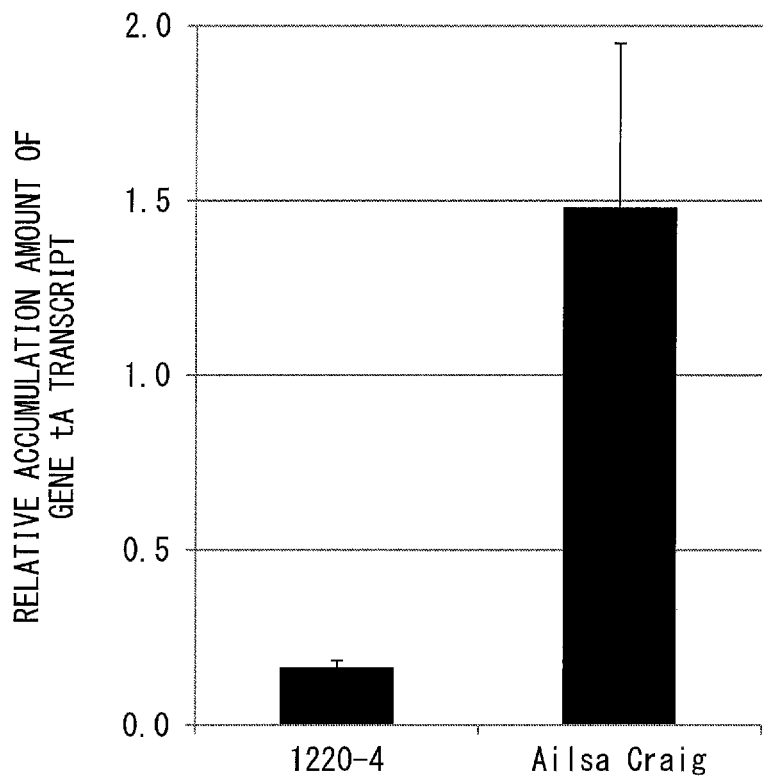
FIG. 15 is a view illustrating an accumulation amount of a transcript of a parthenocarpic gene to in a tomato transformant, in Example 2 of the present invention.

All RNAs were extracted from flower buds of the tomato transformant (individual No. 1220-4) and the non-transformant (control) of the original cultivar "Ailsa Craig" before anthesis, and cDNA was synthesized with the use of Superscript VILO cDNA synthesis kit (Life Technologies Corporation), while using all the RNAs as templates. While using the obtained cDNA as a template, an mRNA accumulation amount of the gene tA was measured by quantitative PCR with the use of, as primers, oligonucleotides represented by SEQ ID NO: 65 and SEQ ID NO: 66. In order to standardize quantitative values, quantitative determination of an internal standard gene was also carried out while similarly using the cDNA as a template. As the internal standard gene, a tomato gene Solyc04g049180.2.1 (data set name: ITAG2.30, website: http://solgenomics.net) was used. This gene is a gene which was found by the inventors to be constitutively expressed in tomato. Further, as the primers for amplifying the internal standard gene, primers represented by SEQ ID NO: 67 and SEQ ID NO: 68 were used. FIG. 15 shows results of this. As shown in FIG. 15, it was confirmed that, in the transformant, expression of the gene tA in the flower bud before anthesis was greatly inhibited, as compared with the non-transformant of the original cultivar Ailsa Craig.

<Quantitative Determination of Indole Acetic Acid (IAA) Concentration in Gene tA Inhibited Transgenic Tomato Line 1220-4, by LC/MS/MS Analysis>

Figure 16:
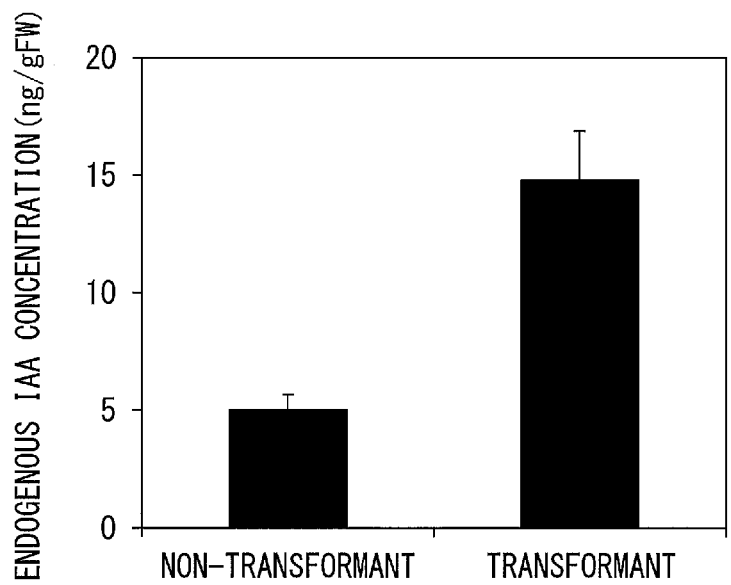
FIG. 16 is a view illustrating an endogenous IAA concentration in a tomato transformant, in Example 2 of the present invention.

Next, IAA was extracted from a flower bud of a gene tA inhibited transformant 1220-4 of tomato, and quantitative analysis was carried out. Note that extraction, purification, and analysis of IAA were carried out with methods similar to those in the case of eggplant in Example 1 above. FIG. 16 shows results of this. In the inhibited transformant, an endogenous IAA concentration which was approximately 3 times higher than that of the non-transformant (cultivar "Ailsa Craig") was observed.

From the above result, it was clarified that parthenocarpy was induced also in tomato by inhibiting expression of the tomato gene tA which is a homologue of the eggplant parthenocarpic gene A.

Example 3

Pepper-Derived Parthenocarpy Responsible Gene pA (1. Identification and Analysis of Pepper-Derived Parthenocarpy Responsible Gene pA)

<Production of Gene pA Function Deficient Mutant by EMS Treatment>

As described in <Analysis of deduced amino acid sequence of gene A product and search for homologous sequence> of Example 1 above, TC19330 (data set name: DFCI Pepper Gene Index ver. 4.0, Reference Literature: Quackenbuch et al. (2001) Nucl. Acid. Res. 29: 159-164, website http://compbio.dfci.harvard.edu/tgi/plant.html) was found as a pepper homologue gene (SEQ ID NO: 35) which has the highest sequence identity relative to the gene A. Hereinafter, this gene is referred to as "gene pA". Mutation induction treatment was carried out by immersing a seed (cultivar "Maor") of pepper (*Capsicum annuum*) in an aqueous solution of EMS (ethyl methane sulfonate) which is a generally used chemical mutagen, and thus artificial mutation of the gene pA was induced. Then, screening of the mutant was carried out. The screening was carried out with the key-point method (Reference Literature: Rigola et al., 2009, PLoS One 4: e4761.) In the Key Point method, seeds at the original generation of mutation induction treatment are shown and, with the use of a DNA sample extracted from a budded plant body, a sample in which genomic DNA from a plurality of samples were multidimensionally mixed was analyzed by a second generation sequencer so as to detect a mutation, and thus an individual having a mutation in a coding region of the gene pA is searched. As a result, a mutant 1 and a mutant 2 were found each of which had a so-called nonsense mutation (i.e., a termination codon with an unchanged reading frame was caused) in the coding region of the gene pA. As compared with a wild type sequence of SEQ ID NO: 35, 125th base in the mutant 1 was mutated from G to A, and 42nd codon was mutated from Trp-encoding TGG to a termination codon TAG. Moreover, in the mutant 2, 127th base was mutated from C to T, and 43rd codon was mutated from Gln-encoding CAA to a termination codon TAA. Therefore, in the mutant 1 and the mutant 2, mutation was caused in the gene pA which encodes a protein made of 394 amino acids represented by SEQ ID NO: 34, and it seemed that an incomplete protein was produced which was made of 41 amino acids or 42 amino acids on the N end side.

<Study of Parthenocarpy of Pepper Gene pA Function Deficient Mutant>

Figure 17:
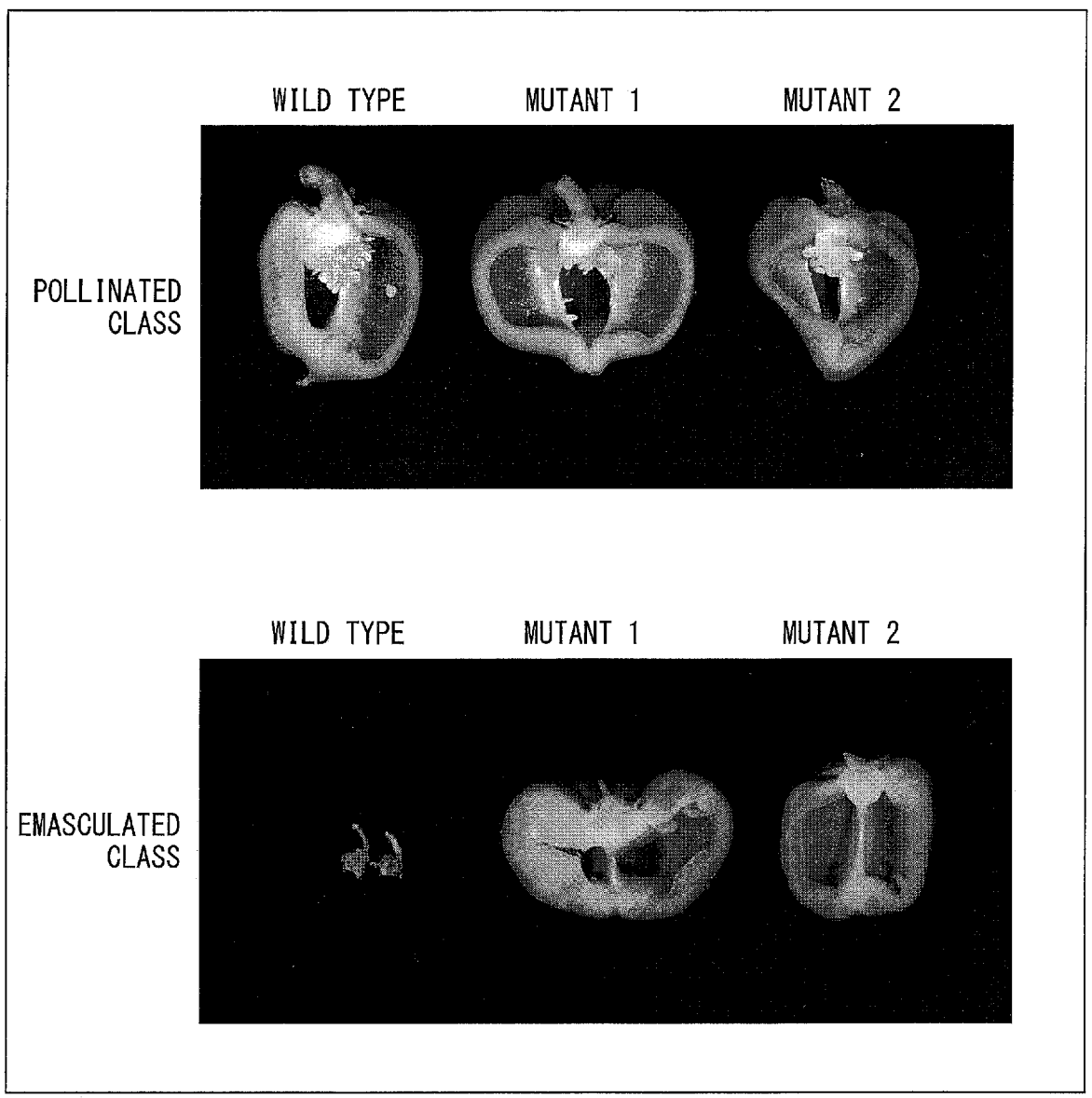
FIG. 17 is a view illustrating parthenocarpy of a pepper mutant, in Example 3 of the present invention.

Each of the mutant 1 and the mutant 2, i.e., obtained induced mutations at the original generation had the mutant gene as a heterozygote, and therefore seeds of their selfed second generations were obtained and analysis was carried out on the seeds thus obtained. In the selfed second generation, an individual showing a wild type homozygote in a mutation site and an individual showing a mutant type homozygote were cultivated. An anther of each of the individuals was removed before anthesis, and parthenocarpy of the individuals was checked. Concurrently, a gene pA function deficient mutant of pepper showing a mutant type homozygote in a mutation site and an individual showing a wild type homozygote, which mutant and individual had been subjected to normal open pollination, were also cultivated, and used as controls by carrying out similar treatment and observing a maturation state of a fruit. FIG. 17 shows results of this. As shown in FIG. 17, in the selfed second generation of the mutant 1 and the mutant 2, the individual which had the wild type homozygote and had been subjected to emasculation produced a fruit which was not enlarged at all, as with general pepper. On the other hand, each of the individuals, which had been obtained from the respective selfed second generations of the mutant 1 and the mutant 2 and had the mutant type homozygote, produced a fruit which was clearly observed to be enlarged even in the case where pollination had been prevented by emasculation.

Moreover, with regard to the individual having the mutant type homozygote, seeds were not formed at all in the enlarged fruit produced from the emasculated flower. On the other hand, with regard to the individuals having any of the wild type homozygote and the mutant type homozygote, enlarged fruits having normal seeds were produced from flowers which had been self-pollinated.

From this, it was confirmed that the enlarged fruit produced from the individual having the mutant homozygote was formed due to parthenocarpy.

From the above results, it was clarified that evident parthenocarpy was induced also in pepper by deficiency of the function of the pepper gene pA which is a homologue of the eggplant parthenocarpic gene A. Moreover, it was shown that the plant body showing parthenocarpy could be obtained by screening (i) an individual in which the gene A has a mutation or (ii) an individual in which a homologue gene of the gene A has a mutation.

(3. Quantitative Determination of Endogenous IAA Concentration of Pepper-Derived Gene pA Mutant)

Figure 18:
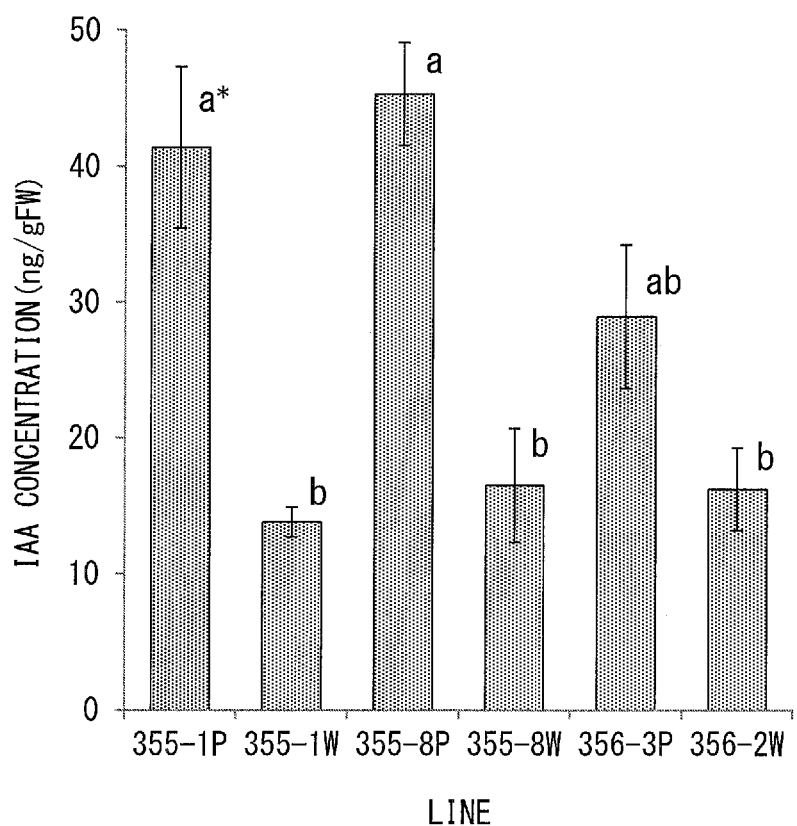
FIG. 18 is a view illustrating an endogenous IAA concentration in a pepper mutant, in Example 3 of the present invention.

From the selfed second generation of the pepper mutant 1, individuals 355-1P and 355-8P, and individuals 355-1W and 355-8W were selected and cultivated. Each of the individuals 355-1P and 355-8P showed parthenocarpy, and its nonsense mutation site found in the gene pA was a mutant type homozygote. Each of the individuals 355-1W and 355-8W did not show parthenocarpy, and its nonsense mutation site found in the gene pA was a wild type homozygote. Here, the individuals 355-1P and 355-1W were sib individuals derived from selfed first generation individuals of the same mutant 1, and the individuals 355-8P and 355-8W were sib individuals derived from selfed first generation individuals of the same mutant 1. Similarly, from the selfed second generation of the pepper mutant 2, an individual 356-3P and an individual 356-2W were selected and cultivated. The individual 356-3P showed parthenocarpy, and its nonsense mutation site found in the gene pA was a mutant type homozygote. The individual 356-2W did not show parthenocarpy, and its nonsense mutation site found in the gene pA was a wild type homozygote. Here, the individuals 356-3P and 356-2W were derived from different selfed first generation individuals of the mutant 2. Buds immediately before anthesis were picked from the respective individuals, and endogenous IAA concentrations in ovaries were measured. FIG. 18 shows results of this. As shown in FIG. 18, it was clarified that, in the gene pA mutant type individuals, endogenous IAA was accumulated at a notably higher concentration than in the wild type individuals. With regard to the mutant 1, the mutant type homozygous individuals (355-1P and 355-8P) showed increase in amount of endogenous IAA which was approximately three times greater than that of the respective wild type homozygotes (355-1W and 355-8W) which were sib individuals. With regard to the mutant 2, the mutant homozygote (356-3P) showed increase in amount of endogenous IAA which was approximately 1.8 times greater than that of the wild type homozygote (356-2W). From these, it was clarified that, even in a parthenocarpic line induced by a nonsense mutation of the pepper gene pA which was a homologue of the eggplant parthenocarpic gene A, the endogenous IAA content in the ovary was notably increased as with the case of eggplant, and the gene pA regulated parthenocarpy of pepper based on a physiological function identical with that of the eggplant gene A.

Example 4

Detailed Analysis of Eggplant Parthenocarpic Gene A (1. Promoter Analysis of Parthenocarpic Gene A with Use of GUS (β-glucuronidase) Gene)

Figure 6:
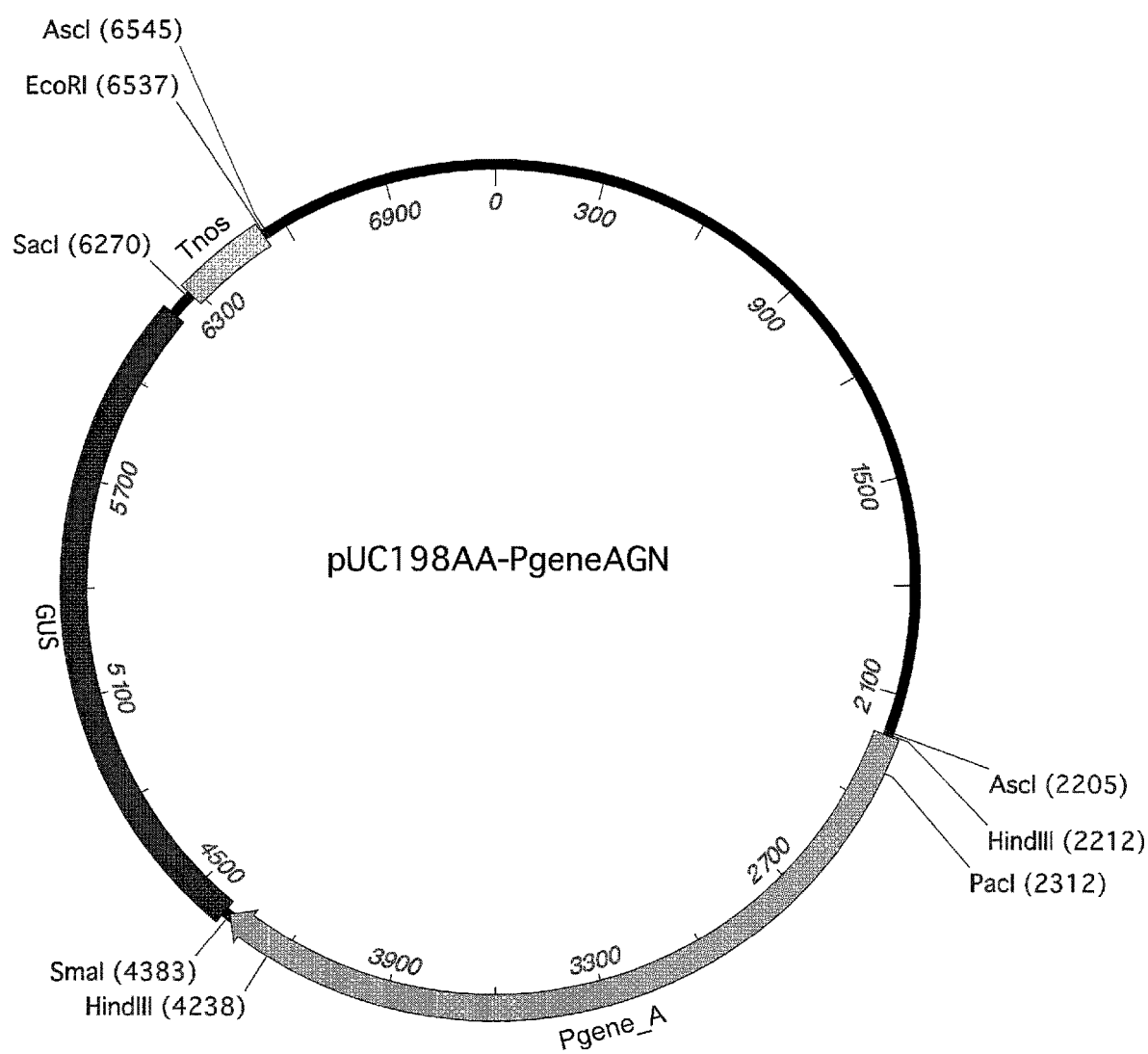
FIG. 6(a) is a view schematically illustrating a vector having a promoter sequence of a gene A, in Example 1 of the present invention.
FIG. 6(b) is a view schematically illustrating a vector constructed during preparation of an RNAi induction vector, in Example 1 of the present invention.
FIG. 6(c) is a view schematically illustrating a vector constructed during preparation of an RNAi induction vector, in Example 1 of the present invention.
FIG. 6(d) is a view schematically illustrating an RNAi induction vector in Example 1 of the present invention.
Figure 6:
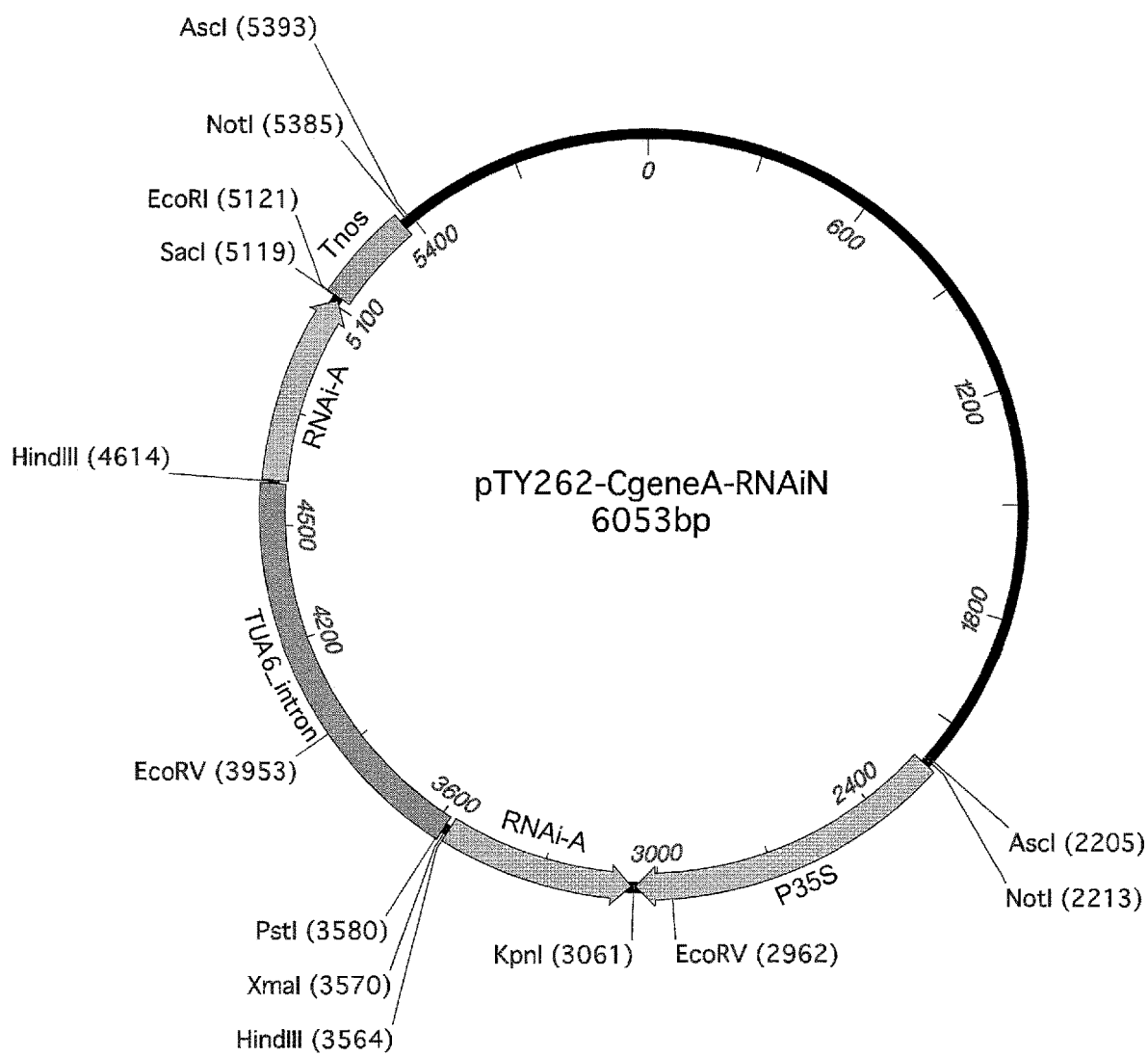
Figure 6:
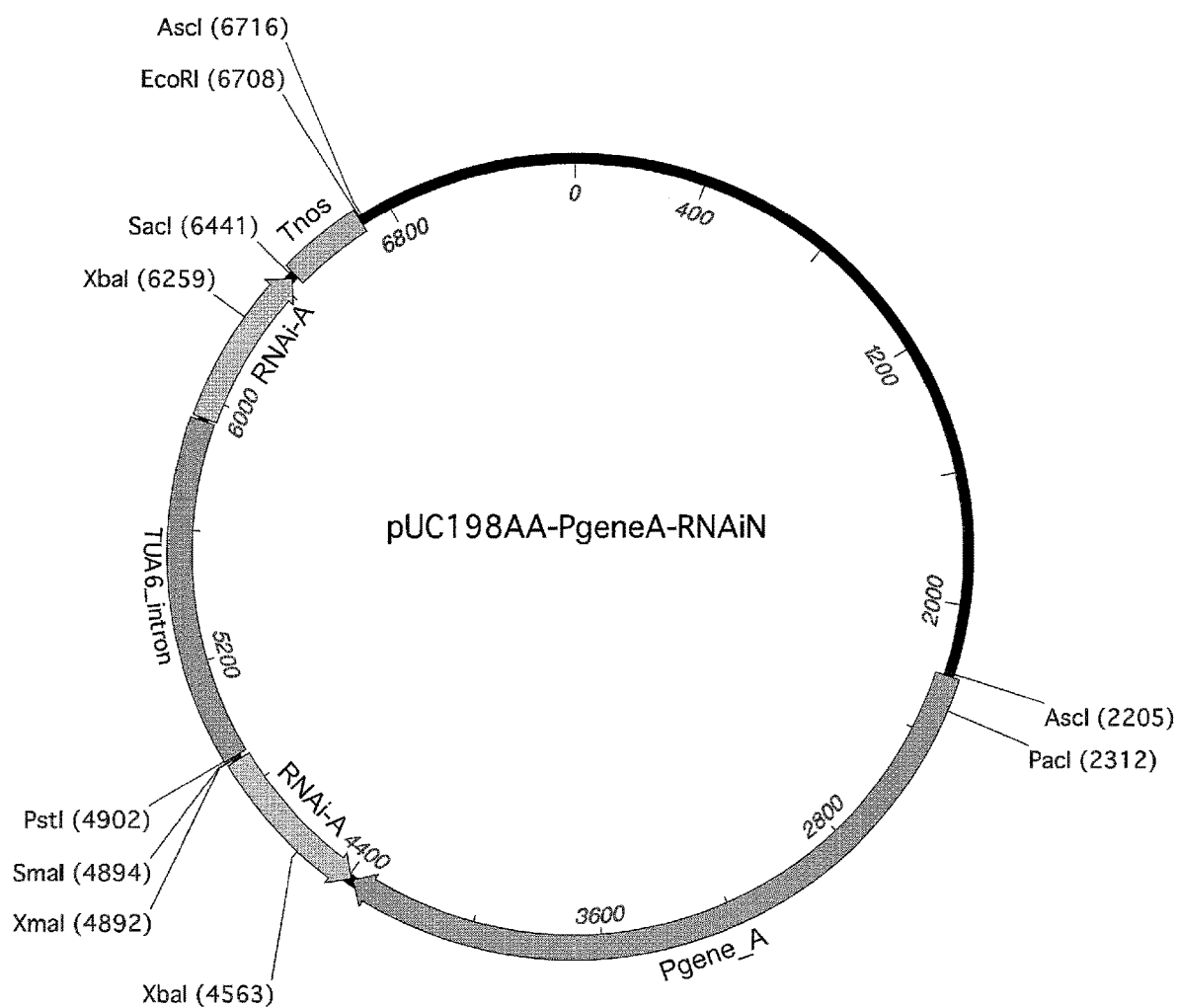
Figure 6:
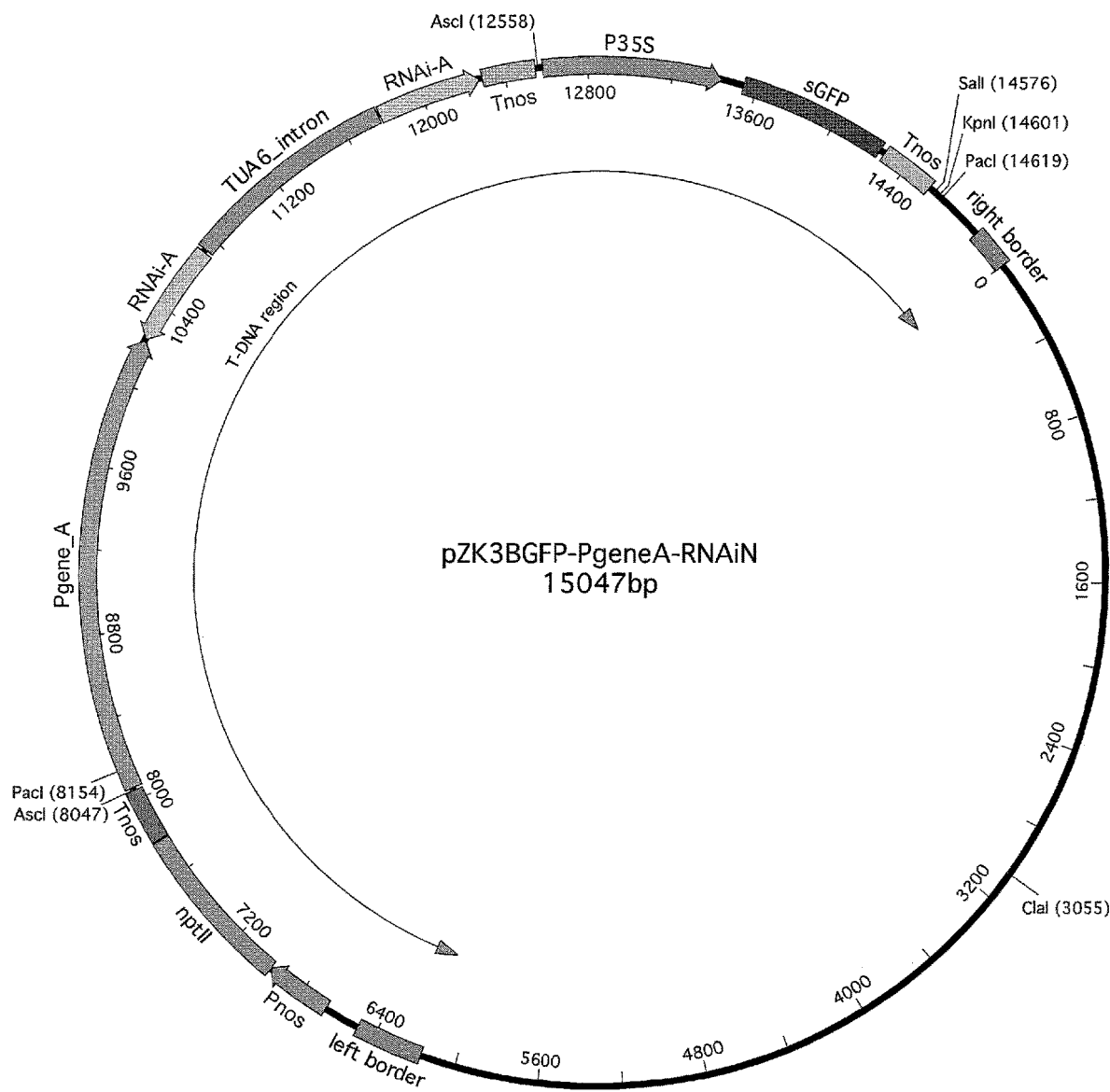
Figure 19:
FIG. 19 is a view illustrating promoter analysis of a parthenocarpic gene A with use of a GUS (β-glucuronidase) gene, in Example 4 of the present invention.

A binary vector pZK3BGFP-PgeneAGN was constructed by inserting an expression cassette PgeneAGN illustrated in FIG. 6(*a*) into an AscI recognition site of a binary vector pZK3BGFP, and the binary vector pZK3BGFP-PgeneAGN was then introduced into an eggplant cultivar "Nakateshinkuro" with the *Agrobacterium* method. Thus, a transgenic plant was obtained. Further, an individual having a transgene as a homozygote was selected from individuals in the selfed first generation of the transformant. A flower produced from the selected individual (12023-3_homozygote) of the eggplant transformant was picked 2 days before anthesis, and an activity of a reporter gene (GUS) was histochemically detected in accordance with a method of Kosugi et al. (Reference Literature: Kosugi et al. (1990) Plant Sci. 70: 133-40) while using X-Gluc as a ground substance. As a result, as shown in FIG. 19, an evident activity of GUS was seen in an entire ovary tissue, an anther, a style, and a petal base. Here, as an artificial application of auxin, auxin is known to induce enlargement of a fruit. Moreover, as above described, the gene A seems to have a function negatively affects biosynthesis of IAA. In consideration of these, the fact that the gene A is expressed in the entire ovary tissue strongly suggests that (i) the gene A has a function to inhibit enlargement of a fruit by keeping an IAA concentration low in the ovary tissue and (ii) deficiency of the function to inhibit enlargement of a fruit, which deficiency is due to a defect of the gene A, causes induction of parthenocarpy.

(2. Study of Parthenocarpy of Eggplant Transformant Produced Separately from Eggplant Transformant of Example 1)

Figure 20:
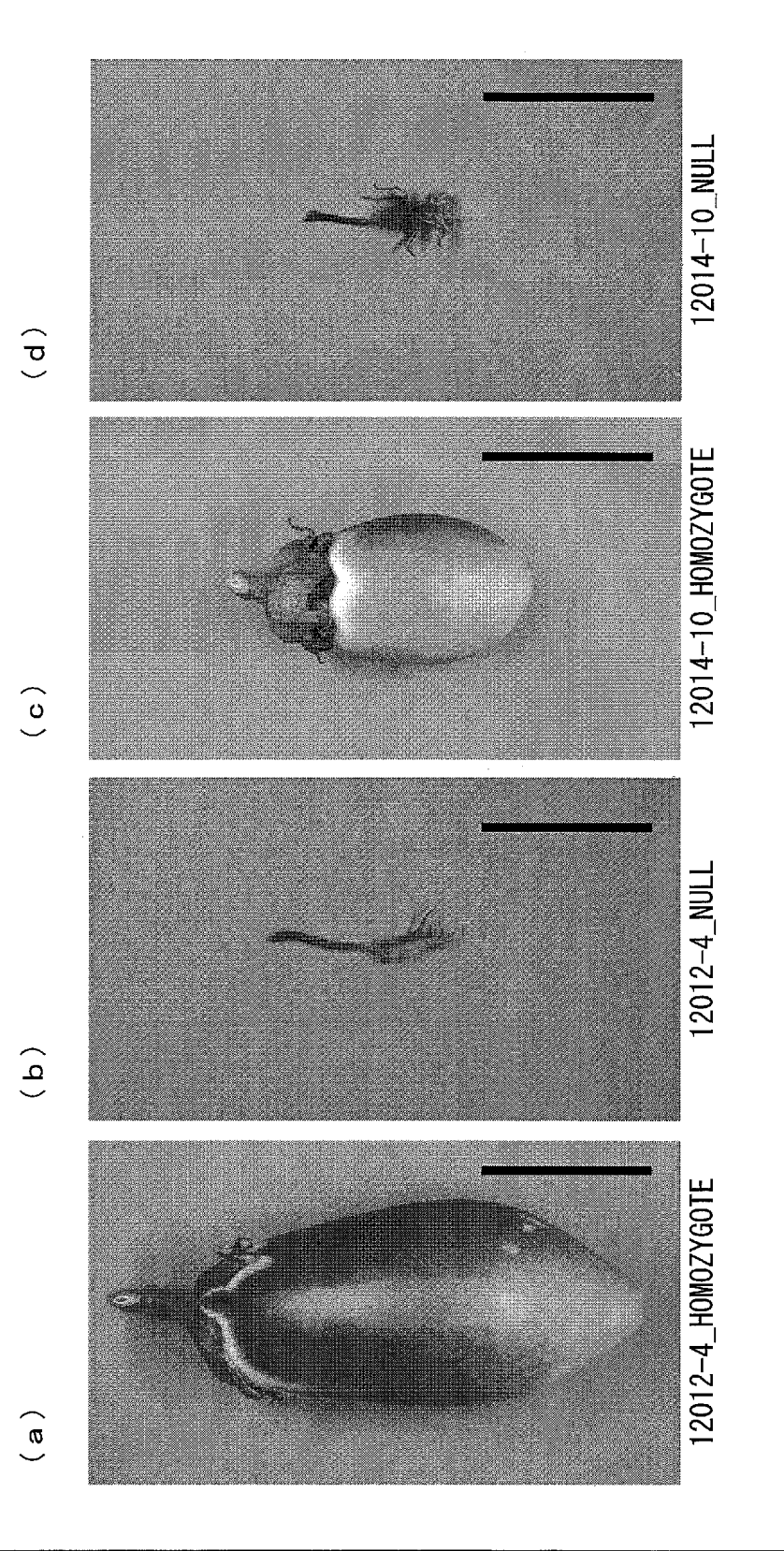
FIGS. 20A-D present views illustrating parthenocarpy of an eggplant transformant produced separately from the eggplant transformant of Example 1, in Example 4 of the present invention.

With a method similar to the method described in <Production of eggplant transformant by RNAi> of Example above, transformants 12012-4_homozygote and 12014-10_homozygote, in which expression of the gene A was inhibited, were newly produced and bred in an experimental system independent from the eggplant transformant (12012-1_homozygote) obtained in Example 1. Moreover, sib individuals 12012-4_null and 12014-10_null, each of which had lost a transgene by genetic segregation, were produced and bred. Parthenocarpy of these transformants was studied with a method similar to the method described in <Study of parthenocarpy of eggplant transformant> of Example 1 above. That is, all the transformants were (i) concurrently cultivated, (ii) treated in the same manner, (iii) observed in terms of enlargement/growth of fruits, and (iv) compared with each other. FIG. 20 shows results. As shown in (a) and (c) of FIG. 20, even in a case where pollination was prevented by removing a stigma before anthesis, fruits produced from the gene-transferred two individuals showed parthenocarpy, and seeds were not formed inside the fruits. On the other hand, as shown in (b) and (d) of FIG. 20, with regard to each of the two null lines 12012-4_null and 12014-10_null which had lost a transgene, no enlarged fruit was formed from a flower organ whose stigma had been removed before anthesis. From the above results, it was confirmed that evident parthenocarpy was induced in three different transformant lines which had been produced and bred by independent different transformation events, in addition to the results of the transformants in Example 1.

Figure 21:
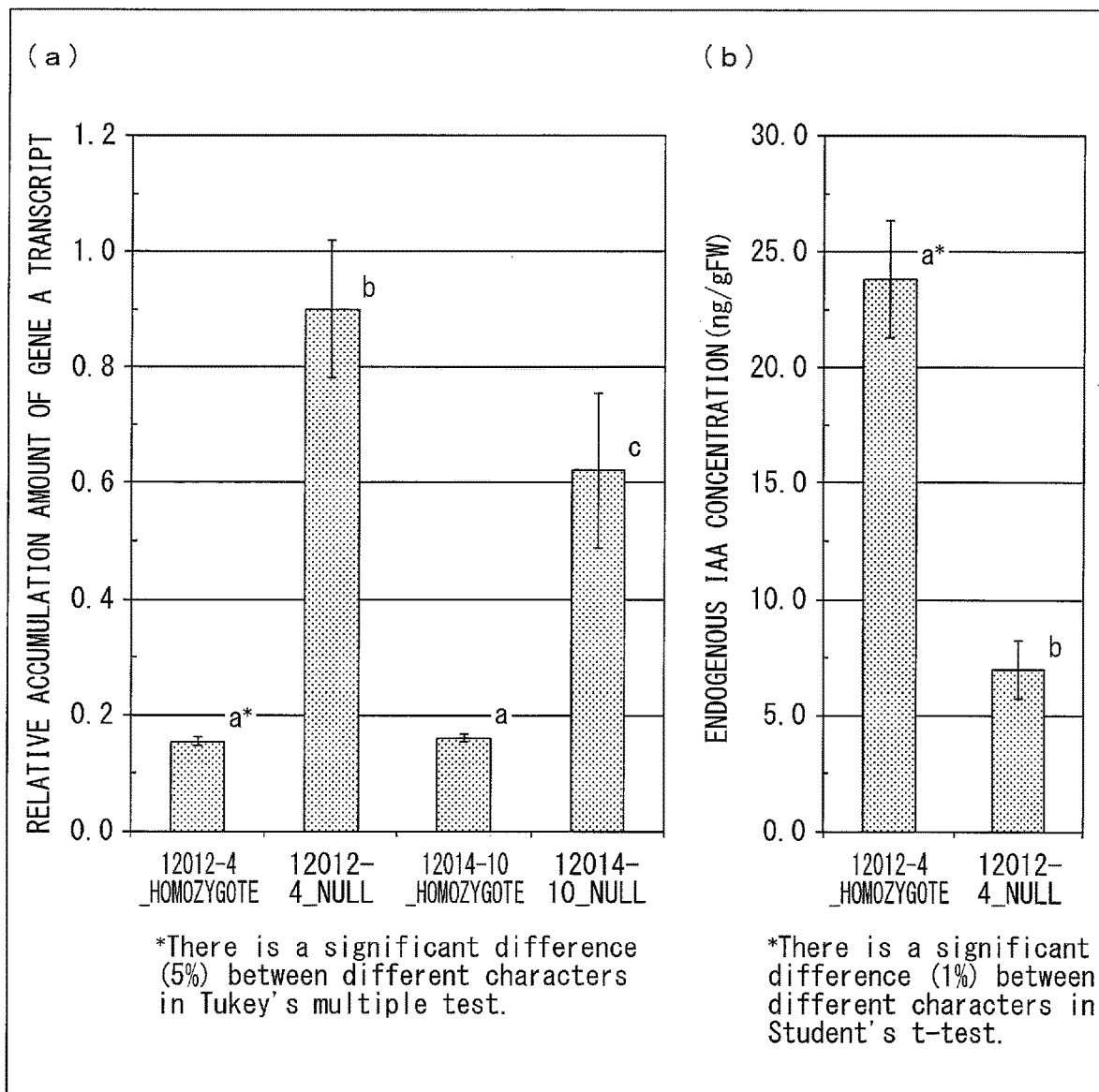
FIG. 21A and FIG. 21B present views illustrating an accumulation amount of a transcript of a parthenocarpic gene A and an endogenous IAA concentration in an eggplant transformant produced separately from the eggplant transformant of Example 1, in Example 4 of the present invention.

Moreover, with a method similar to the method described in <Study of parthenocarpy of eggplant transformant> in Example 1, an mRNA accumulation amount of the gene A was measured in each of two transformants 12012-4_homozygote and 12014-10_homozygote newly obtained in Example 4. (a) of FIG. 21 shows results. As shown in (a) of FIG. 21, in the transformants 1201-4_homozygote and 12014-10_homozygote each of which showed parthenocarpy, expression of the gene A in an ovary at anthesis was greatly inhibited, i.e., the expression of the gene A was approximately ¼ to ⅙ as compared with those in two null lines each of which had lost a transgene.

Further, in the transformant 12012-4_homozygote, an endogenous IAA amount in an ovary at anthesis was measured. The measurement was carried out with a method similar to the method described in (4. Quantitative determination of indole acetic acid (IAA) concentration and IAA metabolite concentration in parthenocarpic eggplant line PCSS) of Example 1. (b) of FIG. 21 showed results. As shown in (b) of FIG. 21, in the transformant 12012-4_homozygote which had a transgene as a homozygote and in which expression of the gene A was inhibited, notable increase in IAA concentration was confirmed which was more than three times of that in the sib line 12012-4_null which had lost a transgene and in which expression of the gene A was not inhibited. The above results further strongly suggested that parthenocarpy is induced in a solanaceous plant by inhibiting expression of a gene function of the parthenocarpic gene A.

(3. Complementation Test on Function of Gene A by Introducing Wild Type Gene A)

<Production of Parthenocarpic Eggplant Line "M3A">

From F5 generation of a line PCSS and a non-parthenocarpic eggplant line TN-45 which had been bred by procedures described in <Detailed mapping of parthenocarpy> of Example 1 and FIG. 3, P34F3_497_55_139 was selected, and its selfed progeny was named "line M3A". In the "line M3A", genotypes of 96 single nucleotide polymorphism markers (Reference Literature: Hirakawa et al. (2014) DNA Res. 21: 649-660) distributed in an entire genome were all homozygosis. Moreover, by PCR with the use of four primers represented by the respective SEQ ID NO: 49 through SEQ ID NO: 52 above, it was confirmed that the "line M3A" had, in homozygosis, a gene which was a mutant type of the gene A derived from the line PCSS (not illustrated). From above, the "line M3A" was determined to be a genetically pure line.

With the use of the "line M3A", an eggplant transformant was produced, and detailed functional analysis of the gene A was carried out as below.

<Production of Eggplant Transformant in Line M3A>

Figure 22:
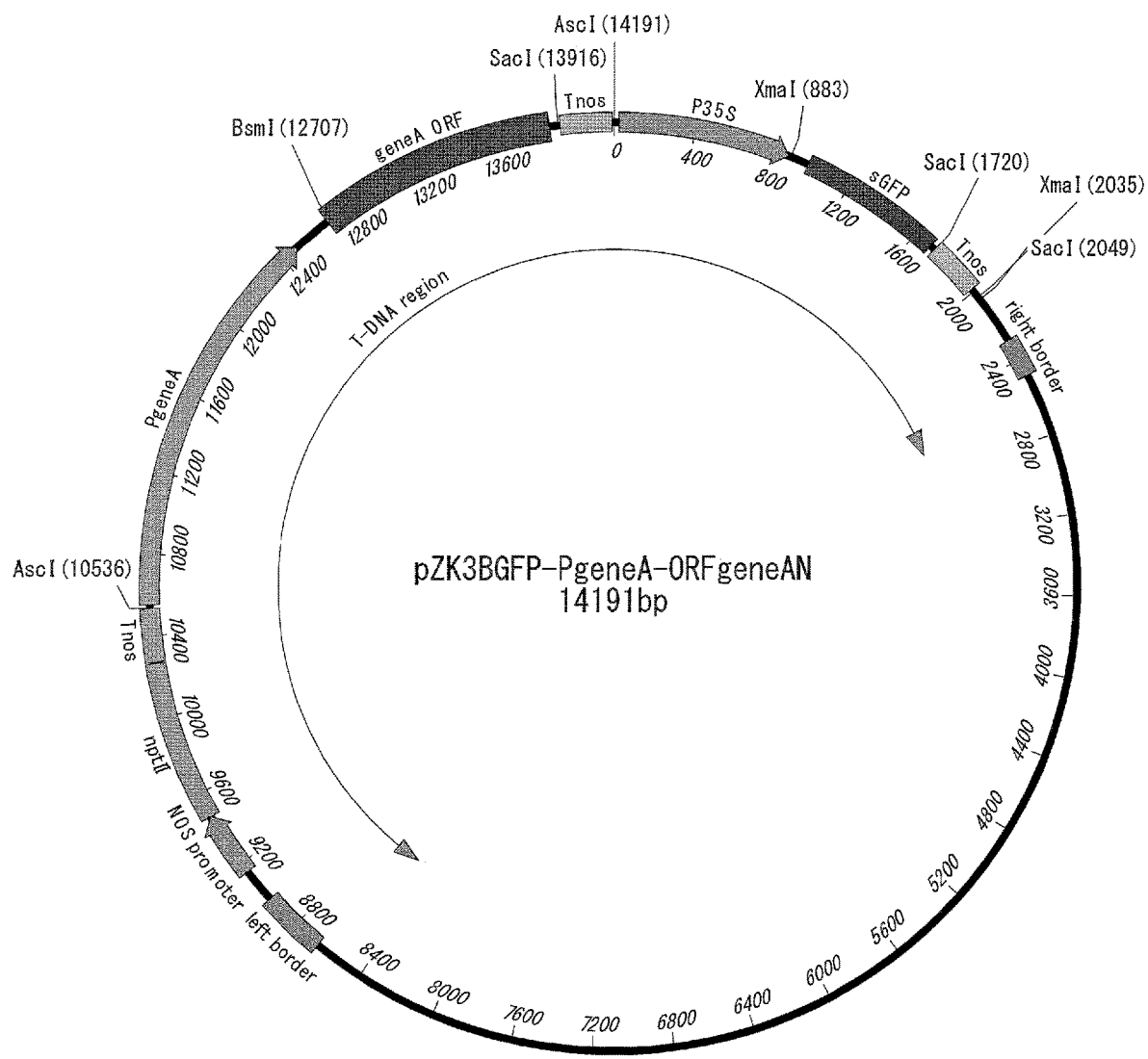
FIG. 22 is a view schematically illustrating a vector for preparing an eggplant transformant, in Example 4 of the present invention.

A sequence including a part of a promoter region, a first exon, and a first intron of the gene A in a genome of an eggplant cultivar "Nakateshinkuro" was amplified by carrying out PCR while using (i) primers represented by SEQ ID NO: 70 and SEQ ID NO: 71 and (ii) a genomic DNA of "Nakateshinkuro" as a template, and thus a fragment including 2313 base pairs represented by SEQ ID NO: 72 was obtained. This fragment had (i) a recognition site of a restricted enzyme XbaI at a part from 3rd base to 8th base from a 5' end and (ii) a recognition site of a restricted enzyme XmaI at a part from 3rd base to 8th base from a 3' end. Note that this fragment has a recognition site of a restricted enzyme BsmI on a first exon at 14th base downstream of a translation start site. The fragment was inserted into an XbaI-XmaI site of a plasmid vector pHSG398 (Takara Bio Inc.), and cloning was carried out. A base sequence of a clone thus obtained was confirmed so as to select a clone pHSG398-PgeneAexlint1 which (i) did not have a mutation derived from PCR amplification in the base sequence and (ii) had an intended base sequence. The clone pHSG398-PgeneAexlint1 was completely digested by a restricted enzyme XbaI and smoothed with the use of Blunting high kit (Toyobo Co., Ltd.), and further completely digested by XmaI. Thus, an intended cloned fragment was cut out. Meanwhile, pUC198AA-CGN described in <Isolation of promoter of gene A> of Example 1 was completely digested by a restricted enzyme HindIII and similarly smoothed, and further completely digested by XmaI. Thus, a CaMV35S promoter was cut out, and the fragment cut out from pHSG398-PgeneAexlint1 was inserted into the part from which the CaMV35S promoter had been cut out. A clone thus obtained was completely digested by BsmI and SacI, and a fragment was cut out which included (i) a part downstream of a BsmI recognition site of a first exon of the gene A, (ii) a part of a first intron, and (iii) a GUS gene derived from pUC198AA-CGN. Another fragment was prepared by digesting, by BsmI and SacI, a clone including an entire protein code of the gene A obtained with a method similar to the method described in <Analysis of expression level of gene A at each site of plant body in each developing stage> of Example 1, and this another fragment was inserted into the part from which the above fragment had been cut out. A clone obtained by the above method had an expression cassette of a wild type gene A (configured by (i) a cDNA sequence including an entire code of the gene A from a promoter region of the gene A via a translation start site and (ii) a NOS terminator sequence derived from pUC198-CGN). The expression cassette was cut out by a restricted enzyme AscI and inserted into an AscI recognition site of a binary vector pZK3BGFP, and thus a binary vector pZK3BGFP-PgeneA-ORFgeneAN was constructed. A structure of the binary vector pZK3BGFP-PgeneA-ORFgeneAN is shown in FIG. 22. This binary vector was introduced into the "line M3A" with a method similar to the method described in <Production of eggplant transformant by RNAi> of Example 1, and thus a transformation individual 13011-3 was produced. Further, from a selfed first generation of the transformation individual 13011-3, an individual 13011-3_homozygote having a transgene A as a homozygote and an individual 13011-3_null which had lost a transgene A by genetic segregation were selected.

<Study of Parthenocarpy of Transformant of Line M3A>

Figure 23:
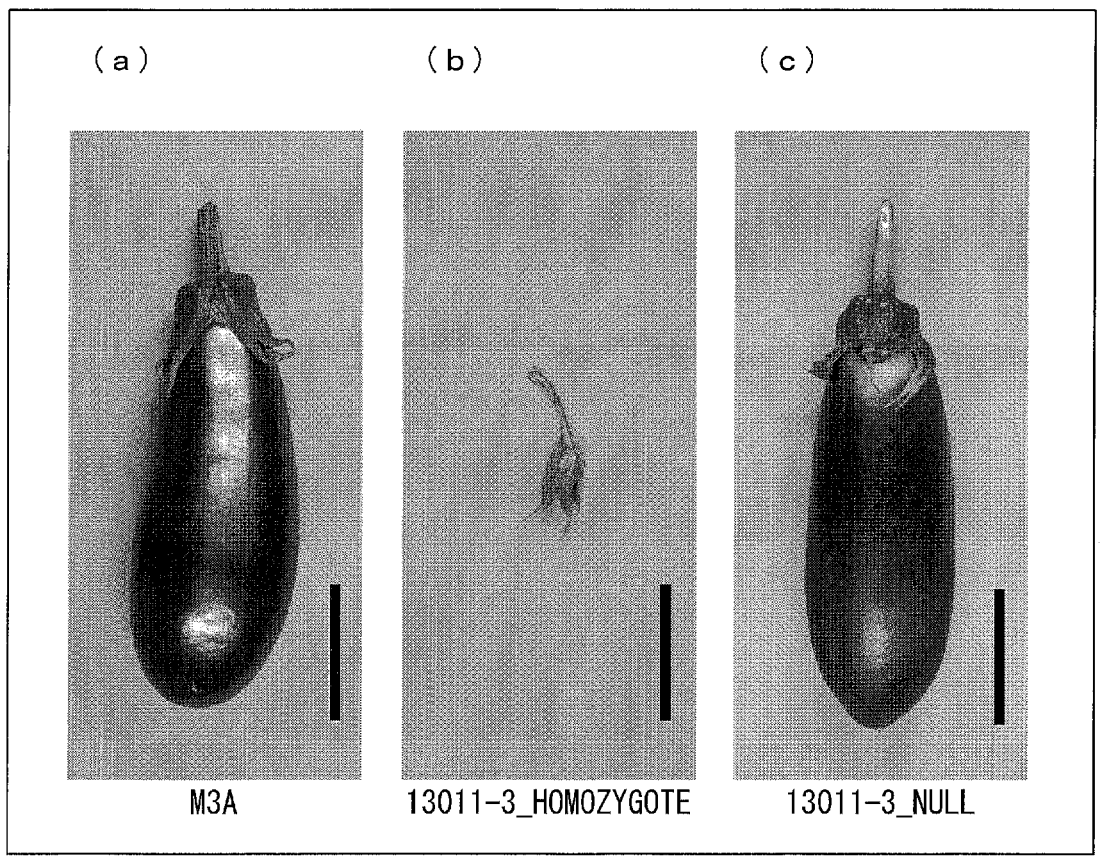
FIGS. 23A-C present views illustrating parthenocarpy of an eggplant transformant in a line "M3A", in Example 4 of the present invention.

The individuals obtained by the above selection were cultivated concurrently with the original line "M3A" which was a non-transformant serving as a control. With a method similar to the method described in <Study of parthenocarpy of eggplant transformant> of Example 1, pollination was prevented by removing a stigma of a flower before anthesis, and parthenocarpy was evaluated by observing enlargement of the fruit after that. FIG. 23 shows results. As shown in (a) of FIG. 23, the original line M3A which was the non-transformant showed evident parthenocarpy whereas, as shown in (b) of FIG. 23, fruit enlargement of the individual 13011-3_homozygote was notably inhibited by the removal of stigma before anthesis, and parthenocarpy which the original line M3A had was lost. Meanwhile, as shown in (c) of FIG. 23, the individual 13011-3_null which had lost a transgene showed evident parthenocarpy, as with the line M3A which was an original line. Moreover, it was confirmed that the observed fruit enlargement was caused by parthenocarpy, from the fact that no seeds were formed inside the fruits.

<Quantitative Determination of Endogenous Indole Acetic Acid (IAA) Amount in Transformant of Line M3A>

Figure 24:
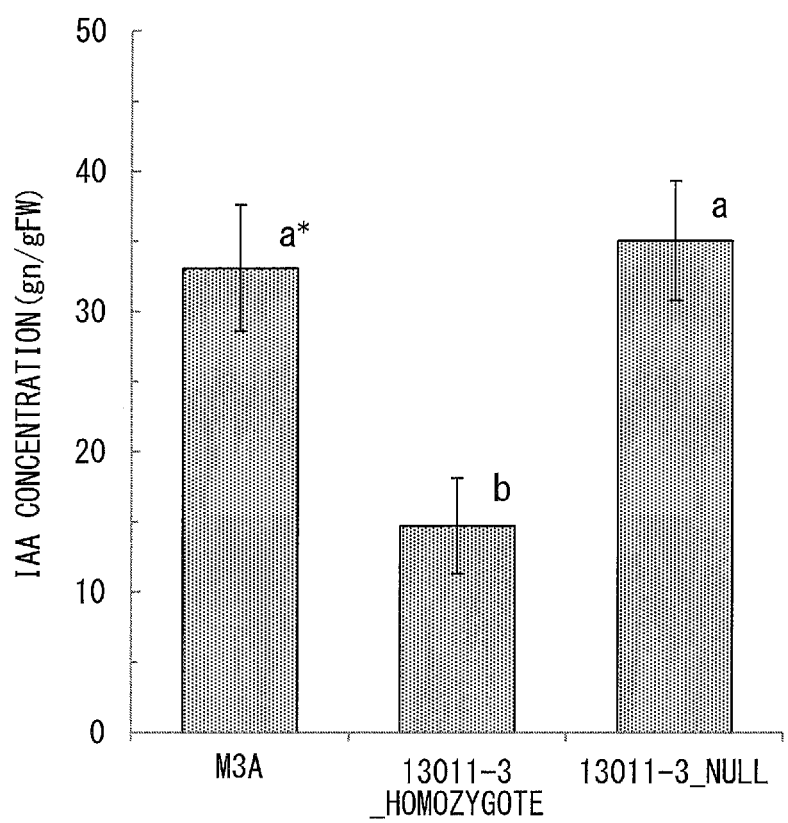
FIG. 24 is a view illustrating endogenous IAA concentration in an eggplant transformant in a line "M3A", in Example 4 of the present invention.

In order to quantitatively determine an endogenous IAA amount in a transformant of the line M3A, an endogenous IAA concentration in an ovary approximately two days before anthesis was measured. The measurement was carried out with a method similar to the method described in (4. Quantitative determination of indole acetic acid (IAA) concentration and IAA metabolite concentration in parthenocarpic eggplant line PCSS) of Example 1. FIG. 24 shows results. As shown in FIG. 24, notable decrease in endogenous IAA concentration was observed in the individual 13011-3_homozygote, as compared with the original line M3A. Moreover, it was clarified in the individual 13011-3_null, which had lost a transgene, that the endogenous IAA concentration was restored to a concentration substantially equal to that of the line M3A.

From the above results, it was clarified that (i) non-parthenocarpy similar to that of a wild type was restored and (ii) a high endogenous IAA concentration which is characteristically seen in an ovary of a parthenocarpic line was notably decreased because parthenocarpy of the line M3A was lost by expressing a wild type normal gene A by a gene A promoter. As such, parthenocarpy derived from the line PCSS was lost and a trait of the wild type was restored by expression of the wild type gene A, and this further clearly showed that deficiency of the function of the gene A was the cause of parthenocarpy of the line PCSS.

(4. Detailed Test of Eggplant Parthenocarpy with Use of Near-Isogenic Line)

<Measurement of Fruit Weight with Use of Near-Isogenic Line>

Figure 25:
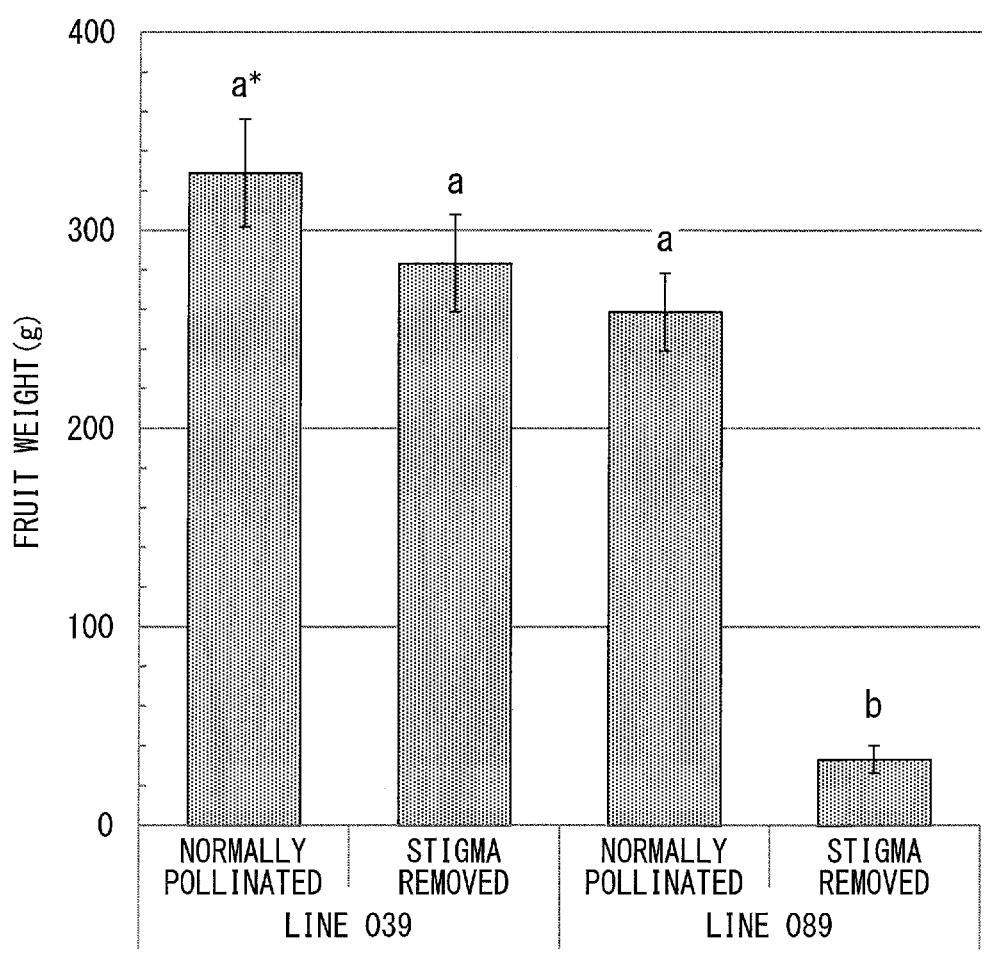
FIG. 25 is a view illustrating weights of a fruit produced from a normally pollinated flower and a fruit produced from a flower whose pollination has been prevented by removing its stigma in near-isogenic lines, in Example 4 of the present invention.

Individuals P43F3_316_7_31_F_E10_10 and P43F3_316_7_31_F_E10_04 in F8 generation which were bred by the procedures described in <Detailed mapping of parthenocarpy> of Example 1 and FIG. 3 were two individuals among sib individuals obtained by selfing of a single F7 generation individual P43F3_316_7_31_F_E10. With regard to the sib individuals, genotypes of 96 single nucleotide polymorphism markers distributed over an entire genome were checked as with the method described in <Production of parthenocarpic eggplant line "M3A"> in Example 4, and a "line 039" and a "line 089", in each of which all checked marker gene loci were fixed in an allelic genotype identical with that of the other line, were bred. Further, the line 039 had, as a homozygote, a mutant type of the gene A derived from the line PCSS, and the line 089 had, as a homozygote, a wild type of the gene A derived from the line TN-43. Therefore, both the lines seemed to be near-isogenic lines in which only the gene A was the mutant type or the wild type and the other genomic regions ware fixed to substantially identical genomic backgrounds. The line 039 and the line 089 were concurrently cultivated, and each of the line 039 and the line 089 was subjected to normal open pollination and stigma removal before anthesis. Fruits were harvested 30 days after anthesis, and weights of the fruits were measured. FIG. 25 shows results. As illustrated in FIG. 25, in the line 039 having a mutant type gene A identical with that of the line PCSS, normally enlarged fruits having weights of approximately 300 g were produced from both a flower which had been normally pollinated and a flower whose pollination had been prevented by removing the stigma. On the other hand, in the line 089, a normally enlarged fruit having a weight (approximately 300 g) equivalent to those of the line 039 was produced from a flower which had been normally pollinated but, from a flower whose pollination had been prevented by removing the stigma, only a fruit which was defectively enlarged and had a weight of 50 g or less was produced, and a normally enlarged fruit was not produced at all. Here, as above described, the line 089 was a near-isogenic line of the line 039, i.e., the line 089 had a genomic background identical with that of the line 039 but the gene A was not a mutant type but was a wild type. From the above results, it was shown that expression of parthenocarpy was controlled by only a difference between having a mutant type gene A as a homozygote and having a wild type gene A as a homozygote, and was not influenced by other genetic factors. Further, it was clearly shown that, in the case of having the mutant type gene A as a homozygote, a normally enlarged fruit having a weight equivalent to that in the case of normal pollination was produced even though pollination had been prevented.

(5. Measurement of Activity of Gene A Protein Expressed by *E. coli*)

<Construction of Vector for Expressing Gene A by *E. coli*>

Figure 26:
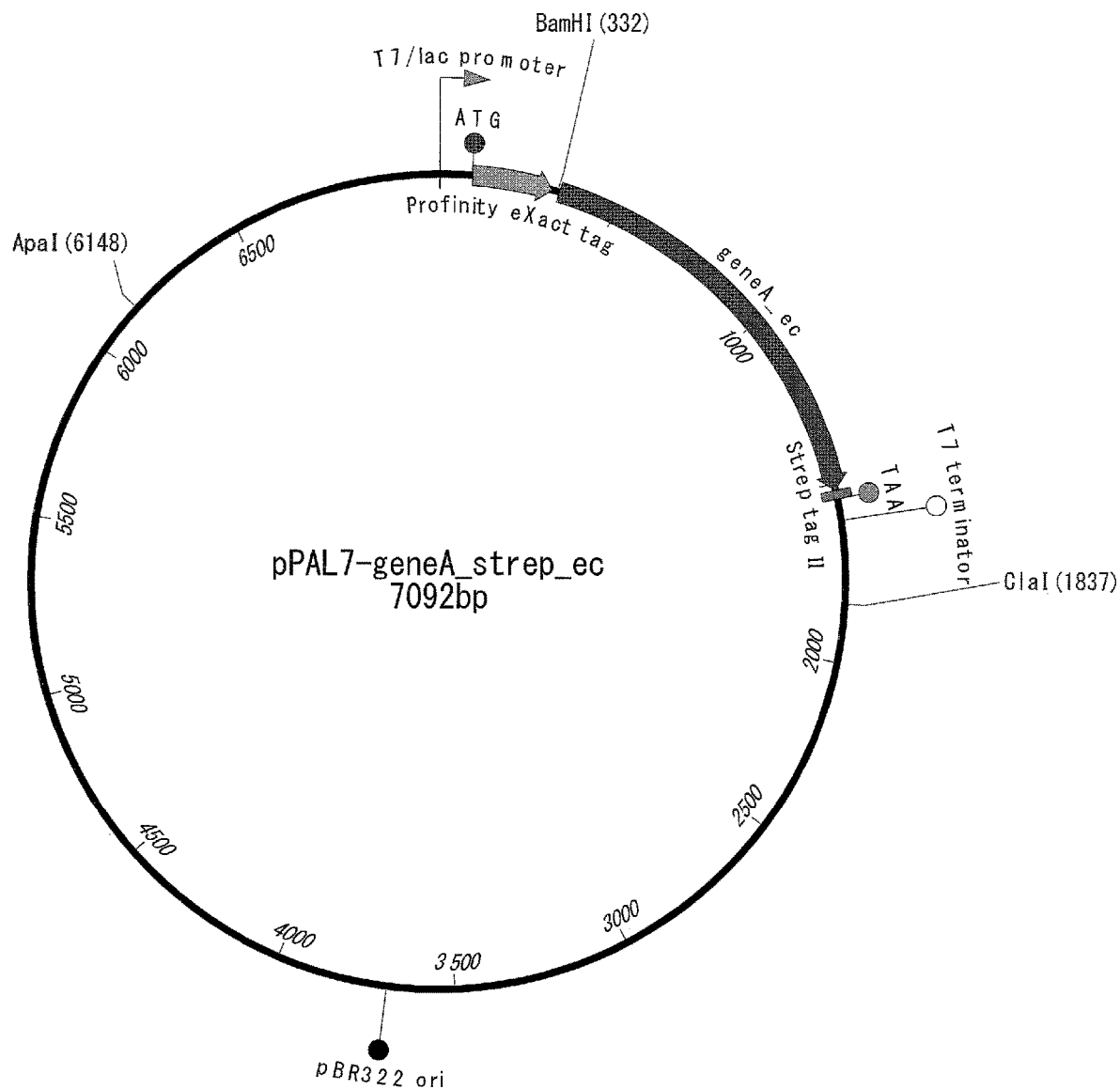
FIG. 26 is a view schematically illustrating an *E. coli* expression vector of a gene A, in Example 4 of the present invention.

SEQ ID NO: 3 represents 1,185 bases from nucleotide number 82 to nucleotide number 1266 in a cDNA sequence of the gene A, and the 1,185 bases include a code sequence of a gene A product represented by SEQ ID NO: 1 and a termination codon. A sequence (SEQ ID NO: 69) including 24 bases for encoding a Strep-tagII sequence was inserted ahead of the termination codon of the sequence of the 1,185 bases while maintaining a reading frame as with the method described in (5. Measurement of activity of protein A encoded by gene A) <Analysis of function of protein A encoded by gene A, with use of transgenic protein> of Example 1, and thus sequence data (SEQ ID NO: 73) was prepared. The sequence in the sequence data (i.e., input sequence data) was converted by the use of an optimization program "GENEius" (Eurofins Genomics K.K.) so as to have a codon usage that was optimal for expressing the gene A by *E. coli*. A DNA sequence thus converted is represented by SEQ ID NO: 74. A deduced amino acid sequence encoded by the sequence of SEQ ID NO: 74 is identical with a sequence in which the Strep-tagII sequence is added to the C end of the deduced amino acid sequence of the gene A product represented by SEQ ID NO: 1. Further, for cloning operation, a sequence of 16 bp represented by SEQ ID NO: 75 was added to a 5' end of a sequence represented by SEQ ID NO: 74, and a sequence of 17 bp represented by SEQ ID NO: 76 was added to a 3' end of the sequence represented by SEQ ID NO: 74. Thus, a DNA fragment whose full length was 1,242 bp was synthesized by outsourcing (Eurofins Genomics K.K.). The DNA fragment (SEQ ID NO: 77) was mixed with an *E. coli* expression vector pPAL7 (Bio-Rad Laboratories, Inc.), which had been treated by restricted enzymes BamHI and NotI, so that the DNA fragment (SEQ ID NO: 77) was inserted into the *E. coli* expression vector pPAL7 by In-Fusion cloning (Clontech Laboratories, Inc.) utilizing homology of ends of both the fragments. FIG. 26 shows a structure of a recombinant vector pPAL7-geneA_s-trep_ec thus obtained. In a cell of *E. coli* into which the vector has been introduced, expression of a downstream gene is induced by a T7/lac promoter, and a gene A product (protein A) is produced which has a Profinity eXact tag at its N end and a Strep-tag II tag at its C end.

<Expression of Protein A in *E. coli*>

Figure 27:
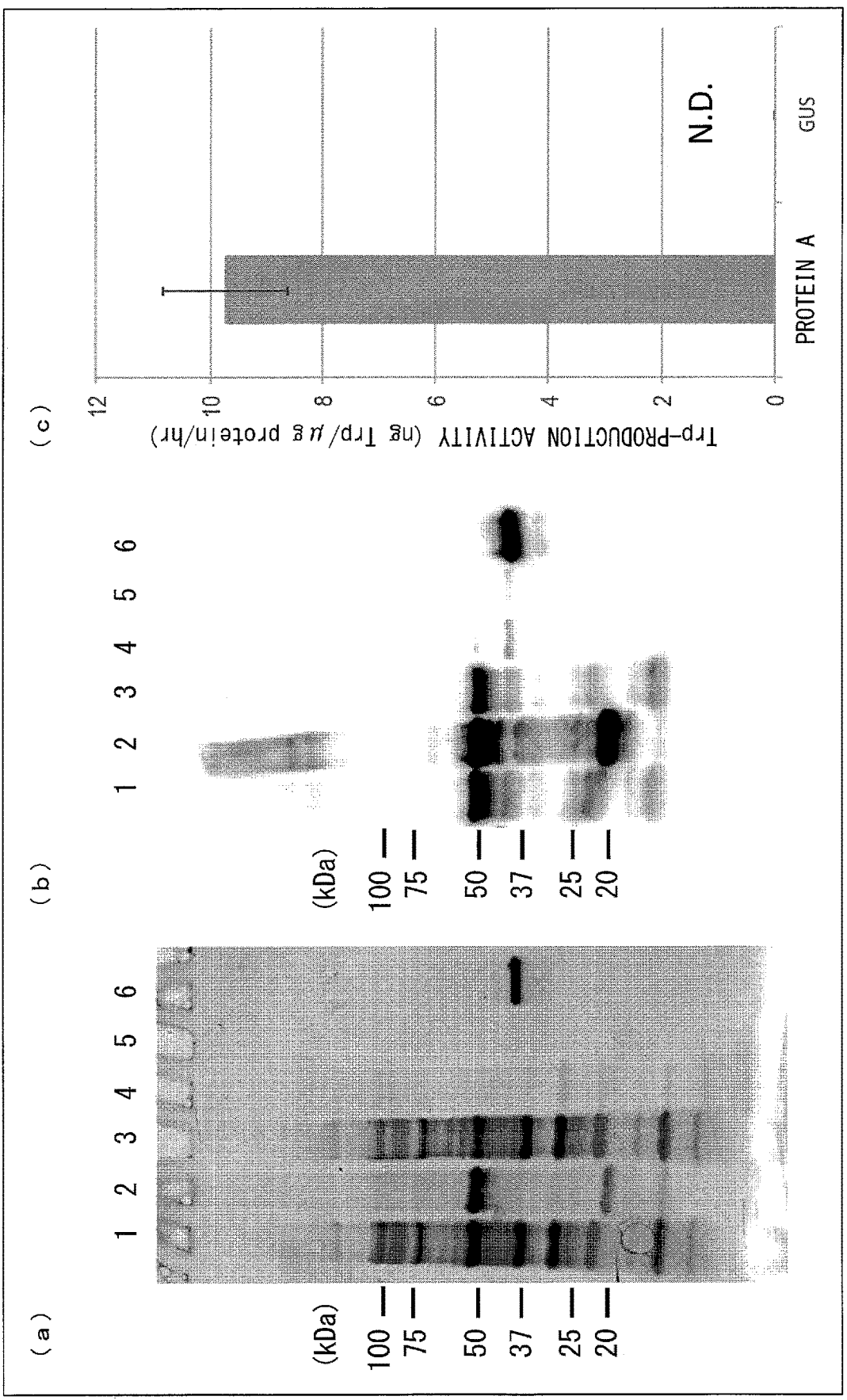
FIGS. 27A-C present views illustrating (i) a result of carrying out electrophoresis on purified protein of a protein A which has been expressed by *E. coli* and (ii) amino group transferase activity of the *E. coli* expression protein A, in Example 4 of the present invention.

The vector obtained with the above method was transformed into an *E. coli* BL21 (DE3) strain, and an obtained clone was cultured at 20° C. for 16 hours in an LB medium containing 0.3 mM of IPTG. After that, harvest was carried out, and a crude protein was extracted with the use of a B-PER protein extracting solution (Thermo Fisher Scientific Inc.). (a) and (b) of FIG. 27 show fractions during purification of a protein after extraction of the crude protein. (a) of FIG. 27 shows a result of electrophoresis carried out with the use of TGX Stain Free gel (Bio-Rad Laboratories, Inc.). (b) of FIG. 27 shows a result of Western blotting carried out, with the use of a Strep-tag II antibody, on a gel identical with the gel shown in (a) of FIG. 27. In the following descriptions, annotations on lane numbers are common to (a) of FIG. 27 and (b) of FIG. 27. First, the crude protein was segregated into an insoluble fraction and a soluble fraction. A lane 1 indicates a result of the soluble fraction in the extracted crude protein. A lane 2 indicates a result of the insoluble fraction. Next, the soluble fraction was passed through a Profinity eXact Mini Spin column (Bio-Rad Laboratories, Inc.) (column in which functional ligand is subtilisin protease), and then the column was washed twice with a wash buffer. A lane 3 indicates a result of a fraction which passed through the column without being bonded to the column. A lane 4 indicates a result of a column wash fraction of the first washing. A lane 5 indicates a result of a column wash fraction of the second washing. Next, by eluting the soluble fraction with the use of an eluate containing sodium fluoride, a Profinity eXact tag which was a prodomain of subtilisin protease was cut off, and a protein A which was an intended protein was eluted from the column. A lane 6 indicates a result of the eluted fraction containing the protein A. Here, the protein A thus obtained had, at its N end, a spacer sequence including 7 amino acid residues derived from pPAL7 and represented by SEQ ID NO: 78. As indicated by the lane 6 in (a) and (b) of FIG. 27, the obtained purified protein was detected as a substantially single band by both (i) fluorescence detection on all proteins by electrophoresis with the use of TGX Stain Free gel (Bio-Rad Laboratories, Inc.) ((a) of FIG. 27) and (ii) detection by transgenic-protein-specific Western blotting with the use of a Strep-tag II antibody ((b) of FIG. 27). From these, the obtained purified protein was confirmed to have been purified with high purity.

Moreover, as a control, a vector structure including an *E. coli*-derived GUS gene instead of the gene A was prepared. That is, as with the gene A, the *E. coli*-derived GUS gene was incorporated into pPAL7 so as to be expressed while a Profinity eXact tag is fused to its N end and a Strep-tag II tag is fused to its C end, and a transgenic protein was prepared with similar procedures. A GUS protein which was thus obtained and in which the Profinity eXact tag was cut off had, at the N end, a spacer sequence including 7 amino acid residues represented by SEQ ID NO: 78, as with the case of the protein A. The transgenic GUS protein obtained with the method was also confirmed, by gel electrophoresis and Western blotting, to have been purified with high purity (not illustrated), as with the case of the protein A.

<Measurement of Activity of *E. coli* Expression Protein A>

To solutions of the transgenic protein A and the transgenic GUS protein obtained above (each of which was 0.5 µg/µL), L-methionine (50 mM), pyridoxal phosphate, and IPyA (1 mM) were added and the mixture was reacted at 37° C. for one hour in 50 mM of a potassium phosphate buffer (pH 8.5). Then, the reaction solution was purified by an OASIS HLB column, and analyzed with the use of LC/MS/MS. As a result, as shown in (c) of FIG. 27, it was clarified that the transgenic protein A had an activity to produce 9.7 ng of tryptophan per hour for each microgram by transamination from methionine to IPyA. On the other hand, in the control experiment in which the transgenic GUS protein was used instead of the transgenic protein A, an activity to produce tryptophan was not higher than a detection limit (N.D.) This strongly suggests that (i) production of tryptophan is dependent on the transgenic protein A and (ii) the spacer sequence at the N end and the Strep-tag II sequence at the C end are irrelevant to tryptophan synthesis activity in which IPyA included in the transgenic protein A is used as a ground substance, i.e., the spacer sequence at the N end and the Strep-tag II sequence at the C end do not influence the tryptophan synthesis activity.

In addition to the results described in (5. Measurement of activity of protein A encoded by gene A) of Example 1, the above results further proved that the protein A encoded by the gene A was an amino group transferase and had an activity to synthesize tryptophan while using, as a ground substance, IPyA which was a precursor of IAA. Moreover, in this case, it was shown that the protein A could at least catalyze transamination from methionine to IPyA.

Based on the above results, the following conclusions can be obtained:

Parthenocarpy of the eggplant line PCSS is caused by deletion mutation of the gene A. The gene A is a gene for encoding amino group transferase that synthesizes tryptophan while using, as a ground substance, IPyA which is a precursor of IAA. Here, the amino group transferase catalyzes reaction to synthesize tryptophan by transferring an amino group of amino acid into an indole pyruvic acid (IPyA). The gene A of the present invention can at least catalyze reaction to synthesize tryptophan by transferring an amino group of methionine into an indole pyruvic acid (IPyA). Further, expression is increased as an ovary of a bud before anthesis develops, and an amount of endogeny of IAA is notably increased due to deficiency of the function of the gene. From these, it seems that the gene A serves to inhibit the endogenous IAA content in the ovary to a certain amount or less. This deficiency of the function of the gene A causes increase in accumulation amount of IAA in the ovary around anthesis, and this increase in accumulation amount of IAA triggers parthenocarpy that is at a practical level in terms of agricultural production. The increase in endogenous IAA amount is not observed in a stem (internode) or at a shoot apex but is specifically observed in an ovary or an anther.

Further, as with eggplant, parthenocarpy can be induced in tomato by inhibiting, by RNAi induction, expression and a function of the tomato homologue gene tA that has 90% or higher of sequence identity of an amino acid sequence to the gene A. Moreover, as with eggplant and tomato, parthenocarpy can be induced in pepper by function deficient mutation caused by EMS treatment in the pepper homologue gene pA that has 90% or higher of sequence identity of an amino acid sequence to the gene A. Further, with regard to tomato and pepper, it has been found that, as with the case of eggplant, the amount of endogeny of IAA is notably increased by deficiency of the function of each of the tomato homologue gene tA and the pepper homologue gene pA. As such, it is concluded that the tomato gene tA and the pepper gene pA induce parthenocarpy by mechanisms similar to that of the eggplant gene A.

INDUSTRIAL APPLICABILITY

According to the present invention, it is possible to obtain a new cultivar plant having parthenocarpy. Moreover, the present invention can be used in fields such as agriculture and horticulture.

[Accession Number]

FERM BP-22257

The invention claimed is:

1. A method for producing a parthenocarpy-regulated plant comprising inhibiting in a plant
   (a) expression of a parthenocarpy regulatory gene encoding an amino acid group transferase polypeptide, wherein the parthenocarpy regulatory gene consists of a polynucleotide recited in any of (1) and (2):
      (1) a polynucleotide encoding a polypeptide having the amino acid sequence of SEQ ID NO: 1, and
      (2) a polynucleotide encoding a polypeptide having a sequence identity of 90% or higher relative to SEQ ID NO: 1,
   wherein the inhibition of (a) the expression of the parthenocarpy regulatory gene is carried out by (a1) introducing into the plant a polynucleotide that inhibits expression of the parthenocarpy regulatory gene or by (a2) disrupting the parthenocarpy regulatory gene,
   wherein the method further comprises selecting a plant having parthenocarpic fruit and wherein the plant is a solanaceous plant.

2. A parthenocarpy-regulated plant produced by the method recited in claim 1.

3. A plant in a progeny plant thereof, each of which is a parthenocarpic plant and in each of which
   expression of a parthenocarpy regulatory gene encoding an amino acid group transferase polypeptide is inhibited, wherein the parthenocarpy regulatory gene consists of a polynucleotide recited in any of (1) and (2):
   (1) a polynucleotide encoding a polypeptide having the amino acid sequence of SEQ ID NO: 1, and
   (2) a polynucleotide encoding a polypeptide having a sequence identity of 90% or higher relative to SEQ ID NO: 1,
   wherein the plant is a solanaceous plant.

4. The plant as set forth in claim 3 wherein:
   in the reaction to synthesize tryptophan by transferring an amino group of an amino acid to an indole pyruvic acid (IPyA), at least one amino acid whose amino group is to be transferred is methionine.

5. The plant and the progeny plant thereof as set forth in claim 3, wherein:
   the solanaceous plant is eggplant, tomato, or pepper.

6. The plant as set forth in claim 5, wherein said plant is a plant specified by the accession number of FARM BP-2257.

7. The plant as set forth in claim 3, wherein said plant is a plant body, a part of the plant body, or a seed of the plant body.

8. The method as set forth in claim 1, wherein the plant is eggplant.

9. The method as set forth in claim 1, wherein the sequence identity relative, to SEQ ID NO: 1 is 95% or higher.

10. The method as set forth in claim 1, wherein
    the plant is tomato, and the parthenocarpy regulatory gene is a gene of tomato.

11. The method as set forth in claim 1, wherein
    the plant is pepper, and
    the parthenocarpy regulatory gene is a gene of pepper.

12. The plant as set forth in claim 3, wherein the sequence identity relative to SEQ ID NO: 1 is 95% or higher.

13. The plant and the progeny plant recited in claim 3, wherein the solanaceous plant is eggplant, and the parthenocarpy regulatory gene is a gene of eggplant.

14. The plant and the progeny plant recited in claim 3, wherein and the solanaceous plant is tomato, and the parthenocarpy regulatory gene is a gene of tomato.

15. The plant and the progeny plant recited in claim 3, wherein the solanaceous plant is pepper, and the parthenocarpy regulatory gene is a gene of pepper.

* * * * *